United States Patent
Wertz et al.

(10) Patent No.: US 11,202,778 B2
(45) Date of Patent: Dec. 21, 2021

(54) AMORPHOUS SOLID DISPERSIONS OF DASATINIB AND USES THEREOF

(71) Applicant: Nanocopoeia, LLC, New Brighton, MN (US)

(72) Inventors: Christian F. Wertz, Saint Louis Park, MN (US); Tzehaw Chen, Saint Louis Park, MN (US)

(73) Assignee: Nanocopoeia, LLC, New Brighton, MN (US)

( * ) Notice: Subject to any disclaimer, the term of this patent is extended or adjusted under 35 U.S.C. 154(b) by 0 days.

(21) Appl. No.: 17/206,823

(22) Filed: Mar. 19, 2021

(65) Prior Publication Data
US 2021/0236489 A1 Aug. 5, 2021

Related U.S. Application Data

(63) Continuation of application No. PCT/US2021/014742, filed on Jan. 22, 2021.
(Continued)

(51) Int. Cl.
*A61K 31/506* (2006.01)
*A61K 9/00* (2006.01)
(Continued)

(52) U.S. Cl.
CPC .......... *A61K 31/506* (2013.01); *A61K 9/0053* (2013.01); *A61K 9/10* (2013.01);
(Continued)

(58) Field of Classification Search
CPC .................................. A61K 47/32; A61K 9/10
See application file for complete search history.

(56) References Cited

U.S. PATENT DOCUMENTS

| | | |
|---|---|---|
| 6,350,786 B1 | 2/2002 | Albano et al. |
| 6,596,746 B1 | 7/2003 | Das et al. |

(Continued)

FOREIGN PATENT DOCUMENTS

| | | |
|---|---|---|
| DK | 2802314 T3 | 1/2021 |
| JP | 2019-70000 | 5/2019 |

(Continued)

OTHER PUBLICATIONS

Budha et al., "Drug Absorption Interactions Between Oral Targeted Anticancer Agents and PPIs: Is pH-Dependent Solubility the Achilles Heel of Targeted Therapy?", Clinical Pharmacology & Therapeutics, vol. 92, No. 2, Aug. 2012, pp. 203-213.
(Continued)

*Primary Examiner* — Savitha M Rao
*Assistant Examiner* — Gregg Polansky
(74) *Attorney, Agent, or Firm* — Mueting Raasch Group

(57) ABSTRACT

Amorphous solid dispersions and pharmaceutical compositions of the protein kinase inhibitor dasatinib. The pharmaceutical compositions may be used in methods of treating a proliferative disorder such as cancer, or in methods of delivering dasatinib to patients without regard to whether the patient is concurrently administered a gastric acid-reducing agent, or without regard to whether the patient has an elevated gastric pH. The compositions may be particularly suitable for patients afflicted by achlorhydria or hypochlorhydria, or *Helicobacter pylori* infection.

30 Claims, 13 Drawing Sheets

Related U.S. Application Data

(60) Provisional application No. 63/018,182, filed on Apr. 30, 2020, provisional application No. 62/965,650, filed on Jan. 24, 2020.

(51) Int. Cl.

| | | |
|---|---|---|
| *A61K 9/10* | (2006.01) | |
| *A61K 31/341* | (2006.01) | |
| *A61K 31/4164* | (2006.01) | |
| *A61K 31/426* | (2006.01) | |
| *A61K 31/4439* | (2006.01) | |
| *A61K 47/32* | (2006.01) | |
| *A61K 47/14* | (2017.01) | |

(52) U.S. Cl.
CPC ........ *A61K 31/341* (2013.01); *A61K 31/4164* (2013.01); *A61K 31/426* (2013.01); *A61K 31/4439* (2013.01); *A61K 47/14* (2013.01); *A61K 47/32* (2013.01)

(56) References Cited

U.S. PATENT DOCUMENTS

| | | | |
|---|---|---|---|
| 6,746,869 B2 | 6/2004 | Pui et al. | |
| 6,764,720 B2 | 7/2004 | Pui et al. | |
| 7,125,875 B2 | 10/2006 | Das et al. | |
| 7,153,856 B2 | 12/2006 | Barrish et al. | |
| 7,279,322 B2 | 10/2007 | Pui et al. | |
| 7,491,725 B2 | 2/2009 | Lajeunesse et al. | |
| 7,498,063 B2 | 3/2009 | Pui et al. | |
| 7,951,428 B2 | 5/2011 | Hoerr et al. | |
| 7,972,661 B2 | 7/2011 | Pui et al. | |
| 8,557,995 B2 | 10/2013 | Miller et al. | |
| 8,680,103 B2 | 3/2014 | Lajeunesse et al. | |
| 8,703,196 B2 | 4/2014 | Babcock et al. | |
| 8,841,303 B2 | 9/2014 | Breitenbach et al. | |
| 8,883,209 B2 | 11/2014 | Babcock et al. | |
| 8,940,800 B2 | 1/2015 | Babcock et al. | |
| 8,974,827 B2 | 3/2015 | Bloom et al. | |
| 8,992,471 B2 | 3/2015 | Dugas et al. | |
| 8,992,603 B2 | 3/2015 | Dugas et al. | |
| 9,040,816 B2 | 5/2015 | Gupta | |
| 9,050,611 B2 | 6/2015 | Pui et al. | |
| 9,108,217 B2 | 8/2015 | Hoerr et al. | |
| 9,211,261 B2 | 12/2015 | Appel et al. | |
| 9,248,217 B2 | 2/2016 | Hoerr et al. | |
| 9,249,134 B2 | 2/2016 | Dwivedi et al. | |
| 9,456,992 B2 | 10/2016 | Brisander et al. | |
| 9,642,694 B2 | 5/2017 | Hoerr et al. | |
| 9,827,230 B2 | 11/2017 | Brisander et al. | |
| 9,833,442 B2 | 12/2017 | Brisander et al. | |
| 9,833,443 B2 | 12/2017 | Brisander et al. | |
| 9,884,857 B2 | 2/2018 | Hafner et al. | |
| 10,143,683 B2 | 12/2018 | Brisander et al. | |
| 10,252,289 B2 | 4/2019 | Hoerr et al. | |
| 10,314,829 B2 | 6/2019 | Brisander et al. | |
| 10,314,830 B2 | 6/2019 | Brisander et al. | |
| 10,555,937 B2 | 2/2020 | Brisander et al. | |
| 10,561,643 B2 | 2/2020 | Brisander et al. | |
| 10,561,644 B2 | 2/2020 | Brisander et al. | |
| 10,561,645 B2 | 2/2020 | Brisander et al. | |
| 10,562,048 B2 | 2/2020 | Chen et al. | |
| 10,772,877 B2 | 9/2020 | Brisander et al. | |
| 10,821,375 B2 | 11/2020 | Fonseca et al. | |
| 2009/0203709 A1 | 8/2009 | Steinberg et al. | |
| 2010/0143459 A1 | 6/2010 | Liepold et al. | |
| 2010/0266692 A1 | 10/2010 | Bloom et al. | |
| 2011/0229627 A1 | 9/2011 | Hoerr et al. | |
| 2011/0287096 A1* | 11/2011 | Gorukanti ............ | A61K 31/506 424/461 |
| 2013/0096116 A1 | 4/2013 | Dalziel et al. | |
| 2013/0323403 A1 | 12/2013 | Hoerr et al. | |
| 2015/0110871 A1 | 4/2015 | Wong | |
| 2015/0190253 A1 | 7/2015 | Dugas et al. | |
| 2016/0175881 A1 | 6/2016 | Lasch et al. | |
| 2016/0235677 A1 | 8/2016 | Hoerr et al. | |
| 2017/0209372 A1 | 7/2017 | Temtem et al. | |
| 2019/0193109 A1 | 6/2019 | Hoerr et al. | |
| 2019/0270735 A1 | 9/2019 | Rao et al. | |
| 2020/0113903 A1 | 4/2020 | Liu et al. | |
| 2020/0179963 A1 | 6/2020 | Chen et al. | |
| 2020/0188400 A1 | 6/2020 | Liu et al. | |

FOREIGN PATENT DOCUMENTS

| | | |
|---|---|---|
| WO | 2005077945 A3 | 8/2005 |
| WO | 2007035874 A1 | 3/2007 |
| WO | 2009053854 A3 | 4/2009 |
| WO | 2010081443 A2 | 7/2010 |
| WO | 2012035074 A1 | 3/2012 |
| WO | 2015181573 A1 | 12/2015 |
| WO | 2017108605 A1 | 6/2017 |
| WO | 2019010092 | 1/2019 |

OTHER PUBLICATIONS

Chen et al., "P-Glycoprotein and Breast Cancer Resistance Protein Influence Brain Distribution of Dasatinib", The Journal of Pharmacology and Experimental Therapeutics, vol. 330, No. 3, pp. 956-963. (2009).

Chu et al., "Gastric Acid Suppression is Associated with Decreased Erlotinib Efficacy in Non-Small-Cell Lung Cancer", Clinical Lung Cancer, vol. 16, No. 1, pp. 33-39. (2015).

Jesson et al., "Carbon Dioxide-Mediated Generation of Hybrid Nanoparticles for Improved Bioavailability of Protein Kinase Inhibitors", Pharm Res (2014) 31:694-705.

Karagianni et al., "Co-Amorphous Solid Dispersions for Solubility and Absorption Improvement of Drugs: Composition, Preparation, Characterization and Formulations for Oral Delivery", Pharmaceutics 2018, 10, 98.

Haouala et al., "Drug Interactions with the Tyrosine Kinase Inhibitors Imatinib, Dasatinib, and Nilotinib", Blood, Feb. 24, 2011, vol. 117, No. 8.

Sridhar et al., "Electrosprayed Nanoparticles for Drug Delivery and Pharmaceutical Applications", Biomatter 3:3, e24281, Jul./Aug./Sep. 2013.

Huang et al., "Fundamental Aspects of Solid Dispersion Technology for Poorly Soluble Drugs", Acta Pharmaceutica Sinica B 2014; 4(1):18-25.

Furmanski et al., "Contribution of Abcc4-Mediated Gastric Transport to the Absorption and Efficacy of Dasatinib", Clin Cancer Res; 19(16) Aug. 15, 2013.

Ha et al., "Does Gastric Acid Suppression Affect Sunitinib Efficacy in Patients with Advanced or Metastatic Renal Cell Dancer?", J Oncol Pharm Practice,, 2015, vol. 21(3), 194-200.

Gala et al., "Harnessing the Therapeutic Potential of Anticancer Drugs Through Amorphous Solid Dispersions", BB—Reviews on Cancer 1873 (2020) 188319.

Herbrink, Maikel, Thesis of Pharmaceutics of Oral Anticancer Agents and Stimulants, Feb. 2, 1990, pp. 1-315.

Hoshino-Yoshino et al., "Bridging from Preclinical to Clinical Studies for Tyrosine Kinase Inhibitors Based on Pharmacokinetics/Pharmacodynamics and Toxicokinetics/Toxicdynamics", Drug Metab. Pharmacokinet. 26(6):612-620(2011).

Mitra et al., "Impaired Drug Absorption Due to High Stomach pH: A Review of Strategies for Mitigation of Such Effect to Enable Pharmaceutical Product Development", Molecular Pharmaceutics, 2013, 10, 3970-3979.

Herbrink, et al., "Inherent Formulation Issues of Kinase Inhibitors", Journal of Controlled Release, 239 (2016) 118-127.

Kamath, et al., "Preclinical Pharmacokinetics and in Vitro Metabolism of Dasatinib (BMS-354825): A Potent Oral Multi-Targeted Kinase Inhibitor against SRC and BCR-ABL", Cancer Chemother Pharmacol (2008) 61:365-376.

Lubach et al., "Investigation of the Rat Model for Preclinical Evaluation of pH-Dependent Oral Absorption in Humans", Molecular Pharmaceutics, 2013, 10, 3997-4004.

(56) References Cited

OTHER PUBLICATIONS

Luo et al., "Dasatinib (BMS-354825) Pharmacokinetics and Pharmacodynamic Biomarkers in Animal Models Predict Optimal Clinical Exposure", Clin Cancer Res 2006; 12(23) Dec. 1, 2006.
Matsuoka et al., "H2-Receptor Antagonist Influences Dasatinib Pharmacokinetics in a Patient with Philiadelphia-Positive Acute Lymphoblastic Leukemia", Cancer Chemother Pharmacol (2012) 70:351-352.
Segal et al., "Oral Chemotherapy Food and Drug Interactions: A Comprehensive Review of the Literature", Journal of Oncology Practice, vol. 10, Issue 4, 2014, pp. 255-268.
Tran et al., "Overview of the Manufacturing Methods of Solid Dispersion Technology for Improving the Solubility of Poorly Water-Soluble Drugs and Application to Anticancer Drugs", Pharmaceutics 2019, 11, 132.
Pang et al., "Pharmacokinetics and Absorption of the Anticancer Agents Dasatinib and GDC-0941 Under Various Gastric Conditions in Dogs-Reversing the Effect of Elevated Gastric pH with Betaine HCI", Mol. Pharmeutics 2013, 10, 4024-4031.
Nguyen et al., "Pharmaceutical Applications of Electrospraying", Journal of Pharmeutical Sciences 105 (2016) 2601-2620.
Koutake et al., "Influence of Proton Pump Inhibitors and H2-Receptor Antagonists on the Efficacy and Safety of Dasatinib in Chronic Myeloid Leukemia Patients", International Journal of Hematology (2020) 111:826-832.
Zhang et al., "Processing Impacton Performance of Solid Dispersions", Pharmaceutics 2018, 10, 142.
Sane et al., "Development and Evaluation of a Novel Microemulsion Formulation of Elacridar to Improve its Bioavailability", J Pharm Sci., 2013; 102(4); 1343-1354.
Smelick et al., "Prevalence of Acid-Reducing Agents (ARA) in Cancer Populations and ARA Drug-Drug Interaction Potential for Molecular Targeted Agents in Clinical Development", Mol. Pharmeceutics 2013, 10, 4055-4062.
Takahashi et al., "Influence of H2-Receptor Antagonists and Proton Inhibitors on Dasatinib Pharmacokinetics in Japanese Leukemia Patients", Cancer Chemother Pharmacol (2012) 69:999-1004.
Tsume et al., "In Vitro Dissolution Methodology, Mini-Gastrointestinal Simulator (mGIS), Predicts Better in Vivo Dissolution of a Weak Base Drug, Dasatinib", European Journal of Pharmaceutical Sciences 76 (2015) 203-212.
Van Leeuwen et al., "Drug-Drug Interactions with Tyrosine-Kinase Inhibitors: A Clinical Perspective", Review, www.thelancet.com/oncology, vol. 15, Jul. 2014. e315-326.
Willemsen et al., "Effect of Food and Acid-Reducing Agents on the Absorption of Oral Targeted Therapies in Solid Tumors", Drug Discovery Today, vol. 21, No. 6, Jun. 2016. 962-976.
Yago et al., "Gastric Re-Acidification with Betaine HCI in Healthy Volunteers with Rabeprazole-Induced Hypochlorhydria", Mol. Pharm., Mar. 8, 2014. 4032-4037.
Yago et al., "The Use of Betaine HCI to Enhance Dasatinib Absorption in Healthy Volunteers with Rabeprazole-Induced Hypochlorhydria", The AAPS Journal, vol. 16, No. 6, Nov. 2014. 1358-1365.
Zhang et al., "pH-Dependent Drug-Drug Interactions for Weak Base Drugs: Potential Implications for New Drug Development", Nature, vol. 96, No. 2, Aug. 2014. 266-277.
Gurunath et al., "Amorphous Solid Dispersion Method for Improving Oral Bioavailability of Poorly Water-Soluble Drugs", Journal of Pharmacy Research 6 (2013) 476-480.
Sprycel-Dasatinib Tablet, E.R. Squibb & Sons, LLC, Highlights of Prescribing Information, 2018. 50 pages.
Press Release, Xspray Pharma Announces Positive Clinical Data for its Lead Product Candidate HyNap-Dasa, Sep. 9, 2018.
Press Release, XSpray Pharma's HyNap-Dasa Shows Formal Bioequivalanece, Oct. 10, 2018.
Press Release, XSpray First Batch of HyNap-Dasa Tablets Manufactured on Commercial Scale According to GMP, Dec. 19, 2019.
Press Release, XSpray Stability Studies Initiated with XSpray's HyNap-Dasa Tablets, Feb. 11, 2020.
Press Release, XSpray Pharma Initiates Pivotal Registration Studies with HyNap-Dasa for the Market Approval Application in the United States, May 29, 2020.
Press Release, XSpray First Study Group Has Been Dosed in XSpray Pharma's Ongoing Pivotal Registration Studies with HyNap-Dasa, Jul. 3, 2020.
Press Release, XSpray Announces Preliminary Results from the First Study for Its Lead Product Candidate HyNap-Dasa, Aug. 12, 2020.
Press Release, XSpray Announces Positive Stability Data on HyNap-Dasa Tablets, Aug. 31, 2020.
Press Release, XSpray Announces Positive Preliminary Results from the Study for its Lead Product Candidate HyNap-Dasa, Sep. 25, 2020.
Press Release, XSpray Pharma has decided to Await the Result of Two Ongoing Clinical Studies Before Submitting its ANDA Application, Dec. 11, 2020.
Press Release, XSpray Pharma Reports Positive Results from a Study with Dasatinib During Omeprazole Treatment, Dec. 30, 2020.
Press Release, XSpray Pharma Announces Results from Additional Bioequivalence Study and Provides Update Regarding Upcoming Regulatory Applications for ANDA and 505(b)(2), Jan. 14, 2021.
Press Release, XSpray Pharmas Study with Modified Formulation of HyNap-Dasa Has Now Started, Jan. 22, 2021.
Press Release, XSpray, Both Groups in the Two Ongoing Bioequivalence Studies with XSpray Pharma's Product Candidate HyNap-Dasa Have Been Dosed, Mar. 5, 2021.
U.S. Appl. No. 17/238,869, filed Apr. 23, 2021. Amorphous Nilotinib Microparticles and Uses Thereof.
PCT International Search Report and Written Opinion for PCT/US2021/014742 dated Apr. 7, 2021 (12 pages).
U.S. Appl. No. 17/328,548, filed May 24, 2021. Orally Disintegrating Tablet Comprising Amorphous Solid Dispersion of Nilotinib.

* cited by examiner ized to the user for the treatment of cancer in adult or pediatric patients.

AMORPHOUS SOLID DISPERSIONS OF DASATINIB AND USES THEREOF

REFERENCE TO RELATED APPLICATIONS

The present application is a continuation application of International Application No. PCT/US2021/014742, filed Jan. 22, 2021, which claims the benefit of U.S. Provisional App. No. 62/965,650 (filed Jan. 24, 2020) and U.S. Provisional App. No. 63/018,182 (filed Apr. 30, 2020); the entire disclosures of which are hereby incorporated by reference.

BACKGROUND

Protein kinase inhibitors (PKIs) have been studied for their potential use in treating various disorders of cellular proliferation, including cancer. The potential for PKIs as a treatment is based on the role that protein kinases are known to play in regulating many cellular pathways, including those involved in signal transduction. Dysregulation of protein kinases has been implicated in the development and progression of many cancers, which suggests that PKIs may be useful as a treatment for disorders or diseases such as cancer that are caused by uncontrolled overexpression or upregulation of protein kinases.

One such PKI is dasatinib, which is currently marketed as an immediate-release formulation for oral administration under the brand name SPRYCEL. SPRYCEL is a pharmaceutical formulation of crystalline dasatinib monohydrate. SPRYCEL is indicated for the treatment of (a) adult patients with newly diagnosed Philadelphia chromosome-positive (Ph+) chronic myeloid leukemia (CML) in chronic phase; (b) adult patients with chronic, accelerated, or myeloid or lymphoid blast phase Ph+ CML with resistance or intolerance to prior therapy including imatinib; (c) adult patients with Philadelphia chromosome-positive acute lymphoblastic leukemia (Ph+ ALL) with resistance or intolerance to prior therapy; (d) pediatric patients one year of age and older with Ph+ CML in chronic phase; and (e) pediatric patients one year of age and older with newly diagnosed Ph+ ALL in combination with chemotherapy.

Presently, oral dosage of SPRYCEL is known to be affected by co-administration with other drugs. For example, oral bioavailability of SPRYCEL is strongly affected when co-administered with gastric acid-reducing agents such as $H_2$ antagonists (e.g., famotidine), proton pump inhibitors (e.g., omeprazole), or antacids. In particular, the prescribing information for SPRYCEL states that "[t]he coadministration of SPRYCEL with a gastric acid reducing agent may decrease the concentrations of dasatinib" and that "[d]ecreased dasatinib concentrations may reduce efficacy."

The aqueous solubility of dasatinib is pH-dependent. As a result, upon administration the exposure (expressed as area-under-the-curve, or "AUC") achieved by oral dosage of SPRYCEL can be reduced significantly when $H_2$ antagonists or proton pump inhibitors are used concomitantly by the patient. Per the SPRYCEL prescribing information, the administration of a single dose of SPRYCEL 10 hours following administration of famotidine (an $H_2$ antagonist) reduced the mean AUC of dasatinib by 61%; and the administration of a single 100 mg dose of SPRYCEL 22 hours following a 40 mg dose of omeprazole (a proton pump inhibitor) at steady state reduced the mean AUC of dasatinib by 43%.

As a result of these clinical findings, the prescribing information for SPRYCEL warns, "[d]o not administer $H_2$ antagonists or proton pump inhibitors with SPRYCEL." The prescribing information further suggests that antacids (such as aluminum hydroxide/magnesium hydroxide) can be considered in place of $H_2$ antagonists or proton pump inhibitors, but simultaneous administration of SPRYCEL with antacids is to be avoided; administration of an antacid should be at least 2 hours before and 2 hours after the prescribed dose of SPRYCEL.

These restrictions on how patients can treat indigestion or excess gastric acidity while treated with SPRYCEL are burdensome, especially in light of how often such symptoms can occur within the patient population. Further, poor adherence to the prescribing information's warnings about taking gastric acid-reducing agents while being treated with SPRYCEL can be detrimental to the patient. Thus, there remains a need in the art for a dasatinib treatment that does not require a patient to avoid co-administration of a gastric acid-reducing agent.

As yet another shortcoming of the currently available dasatinib product, it is known that there is considerable inter- and intra-patient variability in pharmacokinetic parameters with SPRYCEL. The high variability may be due to several factors, including differences in absorption, metabolism, elimination, or other variables. However, in some cases it is possible to reduce the variability of drug products by improving the formulation by which they are administered.

SUMMARY OF DISCLOSURE

An aspect of the disclosure relates to an amorphous solid dispersion ("ASD") comprising dasatinib. The present disclosure also relates pharmaceutical compositions comprising the ASDs, and to methods of treatment involving the administration of the pharmaceutical compositions.

In some embodiments, the ASD or pharmaceutical composition is administered without regard to whether the patient or subject is administered a gastric acid-reducing agent. In some embodiments of the methods of the disclosure, the ASD or pharmaceutical composition is administered to the patient or subject with a gastric acid-reducing agent. The gastric acid-reducing agent may be selected from an $H_2$ antagonist, a proton pump inhibitor, or an antacid.

In some embodiments, the ASD or pharmaceutical composition is administered without regard to whether the patient or subject has elevated gastric pH. In some embodiments, the ASD or pharmaceutical composition is administered to a patient or subject with an elevated gastric pH. In some embodiments, the condition by which the patient's gastric pH is elevated is achlorhydria or hypochlorhydria. In some embodiments, the condition by which the patient's gastric pH is elevated is infection by *Helicobacter pylori*.

A further aspect of the disclosure relates to treatment regimens for treating a proliferative disorder in a patient in need thereof.

Additional aspects of the disclosure relate to a kit for sale to a user, the kit comprising a pharmaceutical composition and a package insert. In some embodiments, the package insert informs the user that the pharmaceutical composition can be co-administered with a gastric acid-reducing agent. In some embodiments, the package insert does not comprise a warning that the pharmaceutical composition should not be co-administered with $H_2$ antagonists or proton pump inhibitors. In some embodiments, the package insert informs the user that the pharmaceutical composition can be suitably administered if the user has chronically elevated gastric pH. In some embodiments, the package insert informs the user that the pharmaceutical composition can be suitably administered if the user has been diagnosed with or is afflicted by achlorhydria or hypochlorhydria. In some embodiments, the package insert informs the user that the pharmaceutical composition can be suitably administered if the user has been diagnosed with or is afflicted by *Helicobacter pylori* infection.

In other aspects, the disclosure provides amorphous solid dispersions having a high drug load of dasatinib, in the range from 70% to 95%. The amorphous solid dispersions of the disclosure are surprisingly stable at these high drug loads.

In still another aspect, the present disclosure provides a pharmaceutical composition that may achieve a reduced inter-subject variability and/or within-subject variability, as compared to the variabilities observed for SPRYCEL.

DETAILED DESCRIPTION

Figure 1:
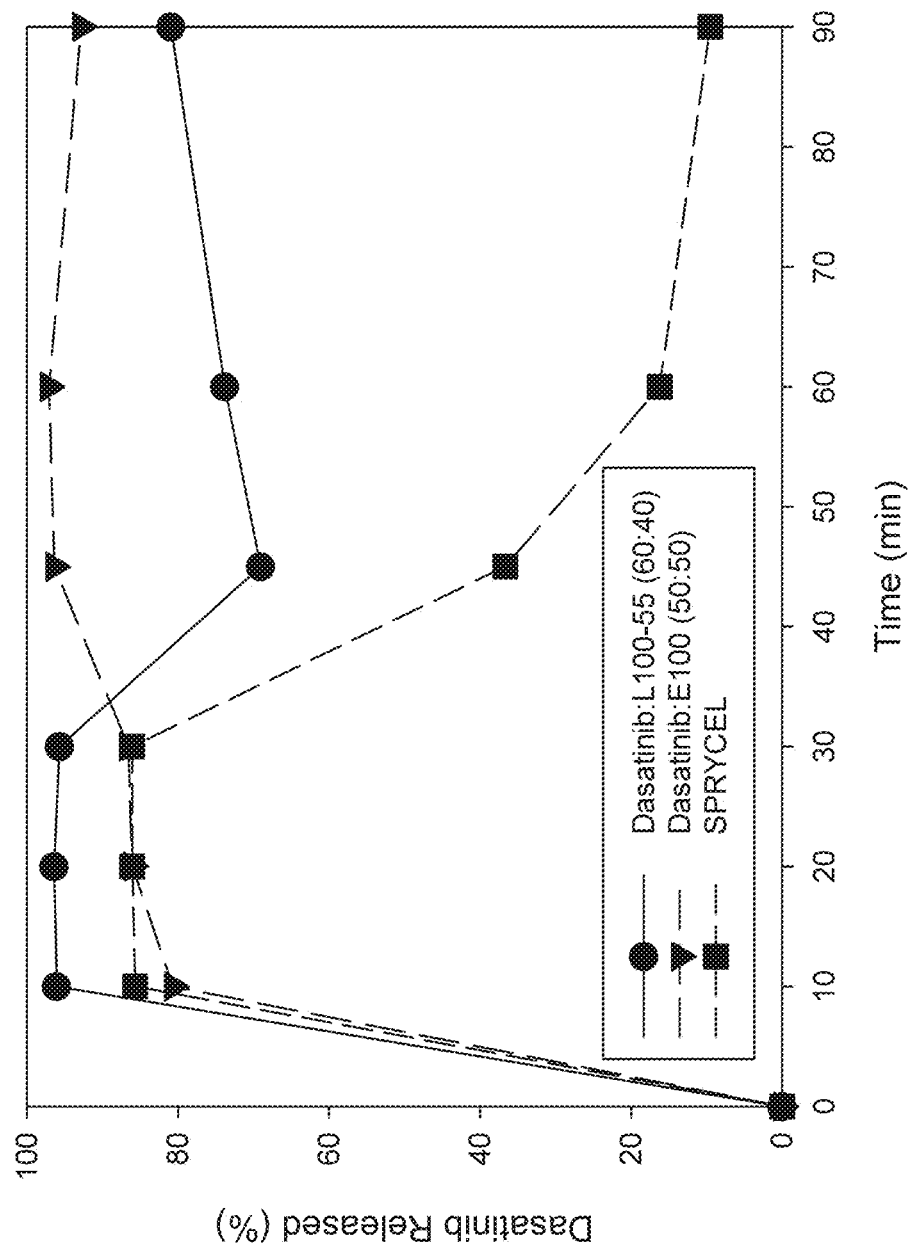
FIG. 1 shows in vitro dissolution profiles of dasatinib dissolved in Fasted State Simulated Gastric Fluid (FaSSGF) (pH 1.6) transitioned to Fasted State Simulated Intestinal Fluid (FaSSIF) (pH 6.4) at t=30 min, for an ASD of dasatinib and EUDRAGIT L100-55 at a w/w ratio (Dasatinib:EUDRAGIT L100-55) of 60:40, for an ASD of dasatinib and EUDRAGIT E100 at a w/w ratio (Dasatinib:EUDRAGIT E100) of 50:50, and for SPRYCEL, as described in Example 3. Each data point represents the mean of three replicates.

The present disclosure relates to dasatinib ASDs, pharmaceutical compositions of dasatinib ASDs, and methods of use involving administration of the dasatinib ASDs or pharmaceutical compositions. The dasatinib ASDs and the pharmaceutical compositions of the present disclosure may provide particular advantages over standard commercial, immediate-release compositions of dasatinib, such as SPRYCEL. For instance, as described herein, the prescribing information for SPRYCEL warns to avoid co-administration with certain gastric acid-reducing agents, because such co-administration can negatively impact blood concentrations of dasatinib, resulting in a possible reduction in efficacy. In contrast, co-administration of the ASDs and pharmaceutical compositions of the disclosure with a gastric acid-reducing agent surprisingly exhibits no such negative effect. As another advantage, pharmaceutical compositions of the disclosure may achieve a reduced inter-subject and/or intra-subject variability, as compared to the variability observed for SPRYCEL.

Thus, dasatinib ASDs and pharmaceutical compositions of the present disclosure offer an advantageous presentation of dasatinib as compared to the currently available commercial immediate-release product.

Dasatinib

Dasatinib is a tyrosine kinase inhibitor. The chemical name for dasatinib is N-(2-chloro-6-methylphenyl)-2-[[6-[4-(2-hydroxyethyl)-1-piperazinyl]-2-methyl-4-pyrimidinyl]amino]-5-thiazolecarboxamide.

Dasatinib has a molecular formula of $C_{22}H_{26}ClN_7O_2S$ and is represented by the following structure:

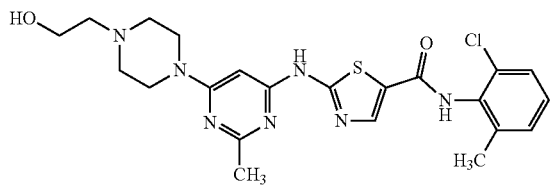 [SMILES: Cc1nc(Nc2ncc(C(=O)Nc3c(C)cccc3Cl)s2)cc(N2CCN(CCO)CC2)n1]

The molecular weight of dasatinib is 488.01 g/mol, while the molecular weight of dasatinib monohydrate is 506.02 g/mol.

SPRYCEL is a commercially available pharmaceutical formulation of crystalline dasatinib monohydrate, marketed in the United States under New Drug Application 21-986. SPRYCEL is currently available as immediate-release tablets containing 20 mg, 50 mg, 70 mg, 80 mg, 100 mg, or 140 mg dasatinib.

Dasatinib in crystalline forms is categorized as a Biopharmaceutical Classification System ("BCS") Class II (low solubility/high permeability) compound. Dasatinib is known to exhibit pH-dependent aqueous solubility. Based on internal experimentation, the aqueous solubility at pH 2 is approximately 1.4 mg/mL and drops rapidly with increasing pH; at pH 6.2, the solubility is less than 1 µg/mL. A preparation of dasatinib in a form that is intended to enhance its solubility could increase its bioavailability. One approach for enhancing solubility is to produce an amorphous solid dispersion.

Amorphous Solid Dispersions of Dasatinib

One aspect of the present disclosure relates to amorphous solid dispersions ("ASDs") comprising dasatinib and one or more polymers. A pharmaceutically suitable amorphous solid dispersion generally comprises a pharmaceutically active ingredient, such as dasatinib, dispersed in a pharmacologically inert carrier, such as a polymer. One aim of a pharmaceutically suitable amorphous solid dispersion is to improve the bioavailability of the pharmaceutically active ingredient. This improvement can occur, for example, because of enhanced surface area, improved wettability or dispersibility, increased dissolution rate, or other factors.

In general, it is favorable if the pharmaceutically active ingredient is dispersed in the polymer to form what has been termed in the art as a "glass solution." However, other forms of dispersion, such as those termed as "solid solution" or "glass suspension," may also be suitable. The precise characterization of the solid dispersion is not important, provided that the amorphous solid dispersion is capable of providing desired characteristics and performance.

In the ASDs of the disclosure, the dasatinib may be as a free base or as a salt such as a hydrochloride. In some embodiments, the dasatinib is as a free base and is anhydrous. Such forms of dasatinib and processes of preparing dasatinib are disclosed, for example, in WO 2005/077945, WO 2007/035874, WO 2009/053854, and WO 2015/181573. In the description of the amorphous solid dispersions and pharmaceutical compositions below, and in the claims, any reference to "dasatinib" refers broadly to dasatinib free base, salts of dasatinib, anhydrous dasatinib (or salts thereof), hydrates or solvates of dasatinib, and hydrates or solvates of dasatinib salts as suitable alternatives, unless specified.

The one or more polymers, which should be pharmacologically inert, should be suitable to provide structure and stability to the ASD. By "pharmacologically inert," it is meant that the material does not initiate a pharmacological response or an adverse reaction when introduced to a relevant biological system (such as the gastrointestinal tract).

In some embodiments, the ASD comprises dasatinib and one or more polymers. In certain embodiments, the ASD consists of dasatinib and the one or more polymers. In certain other embodiments, the ASD consists essentially of dasatinib and the one or more polymers.

Polymers that can be used in the ASDs of the present disclosure may include, but are not limited to, those described below. The term "polymer" includes, but is not limited to, organic homopolymers, copolymers (such as for example, block, graft, random, and terpolymers, etc.), and blends and modifications thereof. The term "copolymer" refers to polymers containing two or more different monomeric units or segments, and includes terpolymers, tetrapolymers, etc.

Polymers that can be used in the ASDs of the present disclosure may include ionizable or non-ionizable polymers, or a combination thereof.

In some embodiments, the one or more polymers may be non-ionizable polymers. In certain embodiments, the ASD consists of dasatinib and one or more non-ionizable polymers. In certain other embodiments, the ASD consists essentially of dasatinib and one or more non-ionizable polymers.

In some embodiments, the one or more polymers may be ionizable polymers. In certain embodiments, the ASD consists of dasatinib and one or more ionizable polymers. In certain other embodiments, the ASD consists essentially of dasatinib and one or more ionizable polymers.

In yet other embodiments, a combination of ionizable and non-ionizable polymers may be used. In certain embodiments, the ASD consists of dasatinib and a combination of one or more non-ionizable polymers and one or more ionizable polymers. In certain other embodiments, the ASD consists essentially of dasatinib and a combination of one or more non-ionizable polymers and one or more ionizable polymers.

Polymers that can be used in the ASDs of the present disclosure may include polymers that exhibit pH-dependent solubility, or polymers that are generally insensitive to pH, or a combination thereof.

In some embodiments, the one or more polymers may exhibit pH-dependent solubility. In certain embodiments, the ASD consists of dasatinib and one or more polymers that exhibits pH-dependent solubility. In certain other embodiments, the ASD consists essentially of dasatinib and one or more polymers that exhibits pH-dependent solubility.

In other embodiments, the one or more polymers may be generally insensitive to pH. In certain embodiments, the ASD consists of dasatinib and one or more polymers generally insensitive to pH. In certain other embodiments, the ASD consists essentially of dasatinib and one or more polymers generally insensitive to pH.

In yet other embodiments, a combination of polymers may include one or more polymers exhibiting pH-dependent solubility and one or more polymers generally insensitive to pH. In certain embodiments, the ASD consists of dasatinib and a combination of one or more polymers exhibiting pH-dependent solubility and one or more polymers generally insensitive to pH. In certain other embodiments, the ASD consists essentially of dasatinib and a combination of one or more polymers exhibiting pH-dependent solubility and one or more polymers generally insensitive to pH.

Non-ionizable polymers. Suitable non-ionizable polymers may include: polysaccharides and polysaccharide derivatives (including cellulose ethers and non-ionizable cellulose esters); polymers or copolymers of N-vinylpyrrolidone and/or vinyl acetate; polymers of ethylene oxide; homopolymers or copolymers of lactic acid and/or glycolic acid; maleic anhydride copolymers; polyvinyl caprolactam-polyvinyl acetate-polyethylene glycol graft copolymer; and poloxamers.

Suitable non-ionizable polysaccharides and polysaccharide derivatives may include cellulose ethers and non-ionizable cellulose esters. Examples of suitable cellulose ethers include methylcellulose ("MC"; e.g., METHOCEL A15 LV, METHOCEL A4M), ethylcellulose ("EC"; e.g., ETHOCEL), hypromellose or hydroxypropyl methylcellulose ("HPMC"; e.g., METHOCEL E3, METHOCEL E5, METHOCEL E6, METHOCEL E15, AFFINISOL HPMC HME), hydroxyethyl cellulose ("HEC"; e.g., NATROSOL 250 Pharm), and hydroxypropyl cellulose ("HPC"; e.g., HPC EF, HPC LF, HPC JF, HPC L, KLUCEL).

Examples of non-ionizable cellulose esters that may be suitable include cellulose acetate, cellulose propionate, cellulose butyrate, and cellulose acetate butyrate.

Examples of suitable polymers or copolymers of N-vinylpyrrolidone and/or vinyl acetate include polyvinylpyrrolidone ("PVP"; e.g., PVP K25, PVP K90, VIVAPHARM PVP), crospovidone or crosslinked polyvinylpyrrolidone (e.g., KOLLIDON CL, VIVAPHARM PVPP), copovidone or vinylpyrrolidone/vinyl acetate copolymer ("PVP/VA"; e.g., KOLLIDON VA 64, VIVAPHARM PVP/VA 64), and polyvinyl alcohol ("PVA"; e.g., VIVAPHARM PVA).

Examples of suitable polymers of ethylene oxide include polyethylene glycol ("PEG"; e.g., KOLLISOLV PEG 8000) and poly(ethylene oxide) ("PEO"; e.g., POLYOX).

Examples of suitable homopolymers or copolymers of lactic acid and/or glycolic acid include polylactide or poly(lactic acid) ("PLA"), polyglycolide or poly(glycolic acid) ("PGA"), and poly(lactic-co-glycolic acid) ("PLGA").

Non-ionizable maleic anhydride copolymers such as poly(methyl vinyl ether/maleic anhydride) ("PVM/MA") may also be suitable. Non-ionizable poloxamers (e.g., PLURONIC, KOLLIPHOR) may also be suitable.

A polyvinyl caprolactam-polyvinyl acetate-polyethylene glycol graft copolymer (e.g., SOLUPLUS) may also be a suitable non-ionizable polymer.

Ionizable polymers. Suitable ionizable polymers may be considered "anionic" or "cationic" polymers. Anionic and cationic polymers often exhibit pH-dependent solubility.

Anionic polymers often include carboxylate (such as acetate), phthalate, succinate, or acrylate functionalities. Anionic polymers are generally insoluble at low pH and more soluble at higher pH. Suitable anionic polymers may include anionic polysaccharides and polysaccharide derivatives (such as ionizable cellulose esters), copolymers of methacrylic acid and/or alkyl acrylate, and derivatized vinyl acetate polymers, for example.

An example of an ionizable polysaccharide that may be suitable is xanthan gum. Examples of suitable ionizable cellulose esters may include carboxymethylcellulose ("CMC"; carboxymethylcellulose sodium), hypromellose acetate succinate, or hydroxypropyl methylcellulose acetate succinate ("HPMC-AS"; e.g., AFFINISOL HPMC-AS, AQUASOLVE, AQOAT), hydroxypropyl methylcellulose phthalate ("HPMC-P"; e.g., HP-50, HP-55), and cellulose acetate phthalate ("CAP"; e.g., EASTMAN C-A-P).

Suitable copolymers of methacrylic acid and/or alkyl methacrylate may include methacrylic acid/methyl methacrylate copolymer (e.g., EUDRAGIT L100) and methacrylic acid/ethyl acrylate copolymer (e.g., EUDRAGIT L100-55, KOLLICOAT MAE).

An example of a derivatized vinyl acetate polymer that may be suitable is polyvinyl acetate phthalate (PVA-P; PHTHALAVIN).

Cationic polymers often include amine functionalities. Cationic polymers are generally soluble at low pH and less soluble at higher pH. Suitable cationic polymers may include cationic polysaccharides and polysaccharide derivatives, and amine-functionalized copolymers of methacrylic acid and/or alkyl acrylate, for example.

An example of a cationic polysaccharide that may be suitable is chitosan.

Suitable amine-functionalized copolymers of methacrylic acid and/or alkyl acrylate include, for example, dimethylaminoethyl methacrylate/butyl methacrylate/methyl methacrylate copolymer (e.g., EUDRAGIT E100) and aminoalkyl methacrylate copolymer such as poly(ethyl acrylate-co-methyl methacrylate-co-trimethylammonioethyl methacrylate chloride (e.g., EUDRAGIT RL100, EUDRAGIT RL PO, EUDRAGIT RS PO).

In some embodiments, the one or more polymers comprise polymers that are characterized by pH-dependent solubility. In some embodiments, the one or more polymers comprise an anionic polymer characterized by pH-dependent solubility. In some embodiments, the one or more polymers comprise a copolymer of methacrylic acid and/or alkyl methacrylate. In some embodiments, the one or more polymers comprise methacrylic acid/methyl methacrylate copolymer (e.g., EUDRAGIT L100) or methacrylic acid/ethyl acrylate copolymer (e.g., EUDRAGIT L100-55).

In some embodiments, the one or more polymers comprise methacrylic acid and ethyl acrylate copolymer. In certain embodiments, the polymer consists of methacrylic acid/ethyl acrylate copolymer. In certain embodiments, the polymer consists essentially of methacrylic acid/ethyl acrylate copolymer. In some embodiments, the ASD comprises dasatinib and methacrylic acid/ethyl acrylate copolymer. In certain embodiments, the ASD consists of dasatinib and methacrylic acid/ethyl acrylate copolymer. In certain other embodiments, the ASD consists essentially of dasatinib and methacrylic acid/ethyl acrylate copolymer. In certain embodiments, the ASD comprises anhydrous, free base dasatinib and methacrylic acid/ethyl acrylate copolymer. In certain embodiments, the ASD consists of anhydrous, free base dasatinib and methacrylic acid/ethyl acrylate copolymer. In certain embodiments, the ASD consists essentially of anhydrous, free base dasatinib and methacrylic acid/ethyl acrylate copolymer.

In any of the foregoing, the methacrylic acid/ethyl acrylate copolymer can be EUDRAGIT L100-55, for example. EUDRAGIT L100-55 is an anionic copolymer demonstrating pH-dependent aqueous solubility. Generally speaking, EUDRAGIT L100-55 is largely insoluble in an aqueous medium at pH of 5 or lower, and largely soluble in an aqueous medium at pH 5.5 or greater.

In other embodiments, the one or more polymers comprise a cationic polymer characterized by pH-dependent solubility. In certain embodiments, the one or more polymers comprise an amine-functionalized copolymer of methacrylic acid and/or alkyl acrylate characterized by pH-dependent solubility.

In some embodiments, the one or more polymers comprise dimethylaminoethyl methacrylate/butyl methacrylate/methyl methacrylate copolymer. In certain embodiments, the polymer consists of dimethylaminoethyl methacrylate/ butyl methacrylate/methyl methacrylate copolymer. In certain embodiments, the polymer consists essentially of dimethylaminoethyl methacrylate/butyl methacrylate/methyl methacrylate copolymer. In some embodiments, the ASD comprises dasatinib and dimethylaminoethyl methacrylate/ butyl methacrylate/methyl methacrylate copolymer. In certain embodiments, the ASD consists of dasatinib and dimethylaminoethyl methacrylate/butyl methacrylate/methyl methacrylate copolymer. In certain other embodiments, the ASD consists essentially of dasatinib and dimethylaminoethyl methacrylate/butyl methacrylate/methyl methacrylate copolymer. In certain embodiments, the ASD comprises anhydrous, free base dasatinib and dimethylaminoethyl methacrylate/butyl methacrylate/methyl methacrylate copolymer. In certain embodiments, the ASD consists of anhydrous, free base dasatinib and dimethylaminoethyl methacrylate/butyl methacrylate/methyl methacrylate copolymer. In certain embodiments, the ASD consists essentially of anhydrous, free base dasatinib and dimethylaminoethyl methacrylate/butyl methacrylate/methyl methacrylate copolymer.

In any of the foregoing, the dimethylaminoethyl methacrylate/butyl methacrylate/methyl methacrylate copolymer can be EUDRAGIT E100, for example. EUDRAGIT E100 is a cationic copolymer of dimethylaminoethyl methacrylate, butyl methacrylate, and methyl methacrylate in a 2:1:1:ratio, and demonstrates pH-dependent aqueous solubility. Generally speaking, EUDRAGIT E100 is largely soluble in an aqueous medium at pH of 5 or lower, and largely soluble in an aqueous medium at pH 5.5 or greater.

In some embodiments, the one or more polymers comprise polymers that are generally insensitive to pH. In some embodiments, the one or more polymers may be non-ionizable polymers characterized that are generally insensitive to pH. In certain embodiments, the one or more polymers may include non-ionizable polysaccharides and polysaccharide derivatives. In yet other embodiments, the one or more polymers may include cellulose ethers and non-ionizable cellulose esters.

In some embodiments, the one or more polymers comprise a hydroxypropyl methylcellulose (also known as "hypromellose" or "HPMC"). In certain embodiments, the one or more polymers consists of one or more hydroxypropyl methylcellulose polymers. In certain embodiments, the one or more polymers consists essentially of one or more hydroxypropyl methylcellulose polymers. In some embodiments, the ASD comprises dasatinib and one or more hydroxypropyl methylcellulose polymers. In certain embodiments, the ASD consists of dasatinib and one or more hydroxypropyl methylcellulose polymers. In certain other embodiments, the ASD consists essentially of dasatinib and one or more hydroxypropyl methylcellulose polymers. In certain embodiments, the ASD comprises anhydrous, free base dasatinib and one or more hydroxypropyl methylcellulose polymers. In certain embodiments, the ASD consists of anhydrous, free base dasatinib and one or more hydroxypropyl methylcellulose polymers. In certain embodiments, the ASD consists essentially of anhydrous, free base dasatinib and one or more hydroxypropyl methylcellulose polymers.

In any of the foregoing, the hydroxypropyl methylcellulose polymer can be a suitable METHOCEL, such as METHOCEL E3, METHOCEL E5, METHOCEL E6, or METHOCEL E15, for example. These METHOCEL grades are non-ionizable water-soluble cellulose ethers, characterized by a methoxyl substitution of 28 to 30%, and a hydroxypropoxyl substitution of 7 to 12%. These grades are characterized by a low solution viscosity (as determined at 20° C. for a 2% solution in water, according to manufacturer's specifications), where the grade number indicates the midpoint of the viscosity range (e.g., METHOCEL E3 is characterized a viscosity of 2.4-3.6 mPa·s; METHOCEL E5 is characterized a viscosity of 4.0-6.0 mPa·s). These grades are considered low molecular-weight HPMC products, having a number average molecular weight (Mn) of about 20 kDa or lower.

While all these grades are suitable for use in the ASDs of the disclosure, METHOCEL E5 has been demonstrated to be particularly suitable. A combination or mixture of grades of hydroxypropyl methylcellulose may also be employed.

In some embodiments, the one or more polymers comprise a low molecular-weight hydroxypropyl methylcellulose. In certain embodiments, the one or more polymers consists of a low molecular-weight hydroxypropyl methylcellulose. In certain embodiments, the one or more polymers consists essentially of a low molecular-weight hydroxypropyl methylcellulose. In any of the foregoing, METHOCEL E5 may be particularly suitable.

In some embodiments, the one or more polymers comprise a low molecular-weight hydroxypropyl methylcellulose characterized by a solution viscosity of 4.0-6.0 mPa·s. In certain embodiments, the one or more polymers consists of a low molecular-weight hydroxypropyl methylcellulose characterized by a solution viscosity of 4.0-6.0 mPa·s. In certain embodiments, the one or more polymers consists essentially of a low molecular-weight hydroxypropyl methylcellulose characterized by a solution viscosity of 4.0-6.0 mPa·s. In any of the foregoing, METHOCEL E5 may be particularly suitable.

In some embodiments of the ASD, the one or more polymers does not comprise a polyvinyl caprolactam-polyvinyl acetate-polyethylene glycol graft co-polymer (e.g., SOLUPLUS). In some embodiments, the ASD is substantially free from a polyvinyl caprolactam-polyvinyl acetate-polyethylene glycol graft co-polymer. In some embodiments, the ASD is essentially free from a polyvinyl caprolactam-polyvinyl acetate-polyethylene glycol graft co-polymer. In some embodiments, the ASD is free from a polyvinyl caprolactam-polyvinyl acetate-polyethylene glycol graft co-polymer. In yet other embodiments, the ASD comprises dasatinib and one or more polymers, with the proviso that the one or more polymer is not a polyvinyl caprolactam-polyvinyl acetate-polyethylene glycol graft co-polymer.

As used herein, the phrase "substantially free from" means that the stated component represents not more than 10% of the ASD, based on weight. The phrase "essentially free from" means that the stated component represents not more than 5% of the ASD, based on weight. The term "free from" means that the stated component represents not more than 2% of the ASD, based on weight.

In some embodiments of the ASD, the one or more polymers does not comprise a polymer or copolymer of N-vinylpyrrolidone. In some embodiments, the ASD is free from a polymer or copolymer of N-vinylpyrrolidone. In yet other embodiments, the ASD comprises dasatinib and one or more polymers, with the proviso that the one or more polymer is not a polymer or copolymer of N-vinylpyrrolidone. In the foregoing, the polymer or copolymer of N-vinylpyrrolidone can be polyvinylpyrrolidone, crospovidone or crosslinked polyvinylpyrrolidone, copovidone or vinylpyrrolidone/vinyl acetate copolymer.

In some embodiments of the ASD, the one or more polymers does not comprise a polyvinylpyrrolidone. In some embodiments, the ASD is free from a polyvinylpyrrolidone. In yet other embodiments, the ASD comprises dasatinib and one or more polymers, with the proviso that the one or more polymers is not a polyvinylpyrrolidone.

In some embodiments of the ASD, the one or more polymers does not comprise a vinylpyrrolidone/vinyl acetate copolymer. In some embodiments, the ASD is free from a vinylpyrrolidone/vinyl acetate copolymer. In yet other embodiments, the ASD comprises dasatinib and one or more polymers, with the proviso that the one or more polymers is not a vinylpyrrolidone/vinyl acetate copolymer.

In the ASDs described in the disclosure, the amount of dasatinib as compared to the amount of the one or more polymers may vary. For example, dasatinib and the one or more polymers may be present in a w/w ratio (dasatinib: polymer) of 30:70 to 95:5. In some embodiments, dasatinib and the one or more polymers may be present in a w/w ratio of 40:60 to 90:10. In other embodiments, dasatinib and the one or more polymers may be present in a w/w ratio of 40:60 to 70:30. In some embodiments, dasatinib and the one or more polymers may be present in a ratio of 70:30 to 95:5. In particular embodiments, the w/w ratio is 30:70, 35:65, 40:60, 45:55, 50:50, 55:45, 60:40, 65:35, 70:30, 75:25, 80:20, 85:15, 90:10, or 95:5.

While amorphous solid dispersions may exhibit enhanced solubility in a biorelevant fluid, the proportion of active ingredient in the amorphous solid dispersion in the particles is usually limited, due to stability issues. Generally, the active ingredient tends toward its more thermodynamically stable crystalline form, so stable amorphous solid dispersions having a high proportion of active ingredient are uncommon. However, an amorphous solid dispersion having a higher proportion of active ingredient is desirable, because the apparent solubility may be enhanced (compared to an amorphous solid dispersion having a lower proportion). Another benefit of having a higher proportion of active ingredient in the amorphous solid dispersion is that an overall smaller dosage form can be achieved, due to the inclusion of a lesser amount of inactive ingredients. Accordingly, the disclosure further provides amorphous solid dispersions having a high drug load of dasatinib. In these embodiments, the dasatinib and the one or more polymers may be present in a ratio of 70:30 to 95:5. In particular embodiments, the w/w ratio is 70:30, 75:25, 80:20, 85:15, 90:10, or 95:5. Such embodiments were surprisingly found to have an unexpectedly high degree of chemical and physical stability.

In some embodiments, the ASDs consist of dasatinib and one or more polymers. In some embodiments, the ASDs consist essentially of dasatinib and one or more polymers. In other embodiments, the ASDs of the present disclosure may additionally comprise one or more other pharmaceutically acceptable functional components, such as one or more antioxidants, wetting agents, or solubilizers.

As used herein, the phrase "pharmaceutically acceptable" means that the component does not initiate a pharmacological response or an adverse reaction when introduced to a relevant biological system. By way of non-limiting example only, a substance found in the U.S. Food & Drug Administration's "Generally Recognized as Safe" ("GRAS") list, or a substance used in accordance with guidelines in its Inactive Ingredient Database, would be considered pharmaceutically acceptable. Similarly, a substance in a corresponding database or list maintained by a parallel regulatory body, such as the European Medicines Agency, would be considered pharmaceutically acceptable. In general, in the pharmaceutical compositions of the disclosure, it is desirable to employ only components that do not cause an unacceptable level of physical or chemical instability in the resulting composition.

Examples of antioxidants that that may be used in the ASDs of the present disclosure include, but are not limited to, acetylcysteine, ascorbyl palmitate, butylated hydroxyanisole ("BHA"), butylated hydroxytoluene ("BHT"), monothioglycerol, potassium nitrate, sodium ascorbate, sodium formaldehyde sulfoxylate, sodium metabisulfite, sodium bisulfite, vitamin E or a derivative thereof, propyl gallate, ethylenediaminetetraacetic acid ("EDTA") (e.g., disodium edetate), diethylenetriaminepentaacetic acid ("DTPA"), bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

In some embodiments, the one or more antioxidants comprise BHT. In some embodiments, the one or more antioxidants comprise propyl gallate. In some embodiments, the one or more antioxidants consist essentially of BHT. In some embodiments, the one or more antioxidants consist essentially of propyl gallate. In some embodiments, the one or more antioxidants consist of BHT. In some embodiments, the one or more antioxidants consist of propyl gallate.

The one or more antioxidants may be present in the ASDs in an amount of 0.001% to 2.0%, or 0.005% to 1.5%, or 0.01% to 1.0%, or 0.05% to 0.5%, by weight. Examples of the amount of the one or more antioxidants in the ASDs include 0.001%, or 0.003%, or 0.005%, or 0.008%, or 0.01%, or 0.015%, or 0.02%, or 0.025%, or 0.03%, or 0.035%, or 0.04%, or 0.05%, or 0.075%, or 0.1%, or 0.2%, or 0.25%, or 0.3%, or 0.4%, or 0.5%, or 0.75%, or 1.0%, or 1.5%, or 2.0%, by weight.

A variety of pharmaceutically acceptable wetting agents may be included. As a non-limiting example of a wetting agent, poloxamers, such as poloxamer 407 (e.g., PLURONIC F-127) or poloxamer 188 (e.g., PLURONIC F-68), may be suitable. Other known pharmaceutically acceptable wetting agents may be suitably employed. A wetting agent may be included in the ASD in an amount of 0.5% to 10%, or 1% to 8%, or 2% to 6%, by weight.

A variety of pharmaceutically acceptable solubilizers may be included. Non-limiting examples of suitable solubilizers include vitamin E TPGS (D-α-tocopherol polyethylene glycol succinate), SLS (sodium lauryl sulfate), and docusate sodium. Other known pharmaceutically acceptable solubilizers may be suitably employed. A solubilizer may be included in the ASD in an amount of 0.1% to 10%, or 0.25% to 5%, or 0.5 to 1%, by weight.

In some embodiments, the ASDs comprise dasatinib, one or more polymers, and one or more antioxidants. In some embodiments, the ASDs consist essentially of dasatinib, one or more polymers, and one or more antioxidants. In certain embodiments, the ASDs consist of dasatinib, one or more polymers, and one or more antioxidants.

In some embodiments, the ASDs comprise dasatinib, methacrylic acid/ethyl acrylate copolymer (such as EUDRAGIT L100-55), and propyl gallate. In certain embodiments, the ASDs consist essentially of dasatinib, a methacrylic acid and ethyl acrylate copolymer such as EUDRAGIT L100-55, and propyl gallate. In certain embodiments, the ASDs consist of dasatinib, methacrylic acid/ethyl acrylate copolymer (such as EUDRAGIT L100-55), and propyl gallate. In particular embodiments, the ASDs consist of dasatinib, methacrylic acid/ethyl acrylate copolymer (such as EUDRAGIT L100-55), and propyl gallate at a level of 0.1-0.5%, by weight of the ASD. In a particular embodiment, the ASD consists of an 80:20 ratio of dasatinib, methacrylic acid/ethyl acrylate copolymer (such as EUDRAGIT L100-55), and propyl gallate at a level of 0.1-0.5% by weight of the ASD.

In some embodiments, the ASDs comprise dasatinib, dimethylaminoethyl methacrylate/butyl methacrylate/methyl methacrylate copolymer (such as EUDRAGIT E100), and propyl gallate. In certain embodiments, the ASDs consist essentially of dasatinib, dimethylaminoethyl methacrylate/butyl methacrylate/methyl methacrylate copolymer (such as EUDRAGIT E100), and propyl gallate. In certain embodiments, the ASDs consist of dasatinib, dimethylaminoethyl methacrylate/butyl methacrylate/methyl methacrylate copolymer (such as EUDRAGIT E100), and propyl gallate. In particular embodiments, the ASDs consist of dasatinib, dimethylaminoethyl methacrylate/butyl methacrylate/methyl methacrylate copolymer (such as EUDRAGIT E100), and propyl gallate at a level of 0.1-0.5%, by weight of the ASD. In a particular embodiment, the ASD consists of a 60:40 ratio of dasatinib, dimethylaminoethyl methacrylate/butyl methacrylate/methyl methacrylate copolymer (such as EUDRAGIT E100), and propyl gallate at a level of 0.1-0.5% by weight of the ASD.

In some embodiments, the ASDs comprise dasatinib, hydroxypropyl methylcellulose (such as METHOCEL E3 or METHOCEL E5), and propyl gallate. In certain embodiments, the ASDs consist essentially of dasatinib, hydroxypropyl methylcellulose (such as METHOCEL E3 or METHOCEL E5), and propyl gallate. In certain embodiments, the ASDs consist of dasatinib, hydroxypropyl methylcellulose (such as METHOCEL E3 or METHOCEL E5), and propyl gallate. In particular embodiments, the ASDs consist of dasatinib, hydroxypropyl methylcellulose (such as METHOCEL E3 or METHOCEL E5), and propyl gallate at a level of 0.1-0.5%, by weight of the ASD. In a particular embodiment, the ASD consists of an 80:20 ratio of dasatinib, hydroxypropyl methylcellulose (such as METHOCEL E3 or METHOCEL E5), and propyl gallate at a level of 0.1-0.5% by weight of the ASD.

As used herein, the phrase "drug load" refers to the ratio (by weight %) of dasatinib in an ASD to the total solids weight of the ASD. By way of example, for an ASD consisting of dasatinib and a polymer, a 1:1 w/w ratio of dasatinib:polymer would represent a 50% drug load; a 4:1 w/w ratio of dasatinib:polymer would represent an 80% drug load, etc. As a second example, an ASD comprising 40% dasatinib by weight, 50% polymer by weight, and 10% by weight of other pharmaceutically acceptable functional components would have a drug load of 40%.

The drug load of dasatinib in the ASDs of the present disclosure may suitably range from 25% to 95%, or 30% to 90%, or 40% to 90%, or 40% to 70%. Examples of the drug load of dasatinib in the ASDs include 25%, or 30%, or 35%, 40%, or 45%, or 50%, or 55%, or 60%, or 65%, or 70%, or 75%, or 80%, or 85%, or 90%, or 95%.

In particular embodiments, the present disclosure provides amorphous solid dispersions having a high drug load of dasatinib, in the range from 70% to 95%. The amorphous solid dispersions of the disclosure are surprisingly stable at these high drug loads. The amorphous solid dispersions provide an enhanced apparent solubility in a biorelevant fluid, and therefore may provide an enhanced in vivo bioavailability. Another benefit of the high drug load amorphous solid dispersion is that an overall smaller dosage form may be possible, due to the inclusion of a lesser amount of inactive ingredients.

For the high drug load embodiments of the ASDs of the present disclosure, the drug load may suitably range from 70% to 95%, or 75% to 95%, or 80% to 90%. Examples of the drug load of dasatinib in the amorphous solid dispersions include 70%, or 75%, or 80%, or 85%, or 90%, or 95%.

The dasatinib ASDs may be in the form of particles. In some embodiments, the particles do not comprise a surfactant. In other embodiments, the particles do not comprise a wetting agent. In yet other embodiments, the particles do not comprise a solubilizer. In other embodiments, the particles comprise neither a surfactant nor a solubilizer. In other embodiments, the particles are free from surfactants, wetting agents, and solubilizers. In other embodiments, the particles consist of polymer and dasatinib, and no additional functional components.

Particles of the ASDs of the disclosure may generally comprise the shapes of spheroids. As measured by conventional light scattering or laser diffraction techniques, the diameter of the particles may generally range from about 0.05 μm to about 100 μm. The median diameter (D50 or Dv0.5) of the particle distribution may be in the range from 0.2 μm to 60 μm, or 0.5 μm to 50 μm, or 0.5 μm to 40 μm.

In some embodiments, the median diameter of the particle distribution may be from 1 μm to 40 μm, or from 2 μm to 25 μm, or from 3 μm to 20 μm. By way of example only, such particle size distributions can be achieved by known methods of spray drying.

In some embodiments, the median diameter of the particles may be from 0.1 μm to 10 μm, or from 0.2 μm to 5 μm, or from 0.5 μm to 2 μm. By way of example only, such particle size distributions can be achieved by methods involving electrospraying, discussed further below.

The dasatinib ASDs of the present disclosure may demonstrate a desirable level of physical and/or chemical stability, which can be assessed by different measures. Stability is generally assessed using conventional analytical techniques commonly known in pharmaceutical sciences.

Physical and chemical stability is generally assessed after storage under controlled, elevated environmental conditions ("accelerated conditions") over a specified period of time. The storage conditions may be one or more of 25° C./60% relative humidity ("RH"), or 25° C./protected, or 30° C./65% RH, or 40° C./75% RH, or 40° C./protected, or 50° C./80% RH. (As used herein in this context, "protected" means samples were sealed in foil pouches and placed in a controlled chamber for the storage period). The period of time may be one or more of 1 week, or 2 weeks, or 4 weeks or 1 month, or 2 months, or 3 months, or 4 months, or 6 months, or 9 months, or 12 months, or 15 months, or 18 months, or 21 months, or 24 months, or any period of time therebetween.

The dasatinib ASDs may demonstrate stability by having a particular assay value or a particular level of total related substances (e.g., impurities), as measured by high performance liquid chromatography ("HPLC"), after storage under accelerated conditions over a specified period of time. The assay value is generally presented as a percentage of the quantity of analyte (e.g., dasatinib) detected relative to the quantity expected, with 100% is a favorable result and large deviations from 100% are unfavorable. The total related substances is generally presented as a percentage relative to the total quantity of substances detected (i.e., analyte plus impurities), where near 0% is favorable and large deviations from 0% are unfavorable.

In some embodiments, the dasatinib ASDs may have an assay as measured by HPLC of at least 90%, or at least 93%, or at least 95%, or at least 97%, or at least 98%, or at least 99%. In some embodiments, the dasatinib ASDs may have a level of total related substances as measured by HPLC of no more than 3%, or no more than 2.5%, or no more than 2%, or no more than 1.5%, or no more than 1%, or no more than 0.9%, or no more than 0.8%, or no more than 0.7%, or no more than 0.6%, or no more than 0.5%.

In some embodiments, the dasatinib ASDs may have an assay as measured by HPLC of at least 90%, or at least 93%, or at least 95%, or at least 97%, or at least 98%, after storage at 25° C./60% RH for 1 month, or 2 months, or 3 months, or 6 months. In some embodiments, the dasatinib ASDs may have a level of total related substances as measured by HPLC of no more than 1.5%, or no more than 1%, or no more than 0.9%, or no more than 0.8%, or no more than 0.7%, or no more than 0.6%, or no more than 0.5%, after storage at 25° C./60% RH for 1 month, or 2 months, or 3 months, or 6 months.

In some embodiments, the dasatinib ASDs may have an assay as measured by HPLC of at least 85%, or at least 90%, or at least 93%, or at least 95%, or at least 96%, or at least 97%, or at least 98%, or at least 99%, after storage at 40° C./75% RH for 1 month, or 2 months, or 3 months, or 6 months. In some embodiments, the dasatinib ASDs may have a level of total related substances as measured by HPLC of no more than 2%, or no more than 1.5%, or no more than 1%, or no more than 0.9%, or no more than 0.8%, or no more than 0.7%, or no more than 0.6%, or no more than 0.5%, after storage at 40° C./75% RH for 1 month, or 2 months, or 3 months, or 6 months.

Stability may be also assessed by evaluating changes in glass transition temperature of the dasatinib ASDs under different storage conditions over time. Glass transition temperature can be evaluated by modulated DSC ("mDSC") using conventional techniques. In some embodiments, the ASD is characterized by a single glass transition, the transition observed in the range from 25° C. to 200° C., or more suitably from 40° C. to 150° C., by mDSC. In other embodiments, the ASD is characterized by more than one transition, the transitions observed in the range from 25° C. to 200° C., or more suitably from 40° C. to 150° C., by mDSC.

In some embodiments, the glass transition temperature as measured by mDSC does not change by more than 5° C., or more than 4° C., or no more than 3° C., after storage at 25° C./60% RH for 1 month, or 2 months, or 3 months, or 6 months. In some embodiments, the glass transition temperature as measured by mDSC does not change by more than 6° C., or more than 5° C., or more than 4° C., or more than 3° C., or more than 2° C., or no more than 1° C., after storage at 40° C./75% RH for 1 month, or 2 months, or 3 months, or 6 months.

Further, stability may be assessed by evaluating changes in crystallinity of the dasatinib ASDs under different storage conditions over time, such as by suitable conventional powder x-ray diffraction techniques (referred to herein as XRD). In the practice of the present disclosure, it is preferred (but not required) that the dasatinib ASD remains amorphous or essentially amorphous. In some embodiments, "amorphous" may be defined as having no detectable crystallinity as determined using methods known in the art, for instance, by using XRD. An example of using XRD to determine amorphicity is provided in Example 1.

In some embodiments, "amorphous" may be defined as having a percent crystallinity of no more than 5%, or no more than 4%, or no more than 3%, or no more than 2%, or no more than 1%, as determined by XRD. In some embodiments, "essentially amorphous" may be defined as having a percent crystallinity of no more than 8%, or no more than 7%, or no more than 6%, as measured by XRD.

The ASDs of the disclosure may be amorphous or essentially amorphous when analyzed promptly after preparation, i.e., at t=0. For these purposes, the phrase "promptly after preparation" means that the ASD is analyzed within a few days after preparation, and stored under protected conditions at ambient temperature and humidity after preparation and before analysis.

The ASDs may be amorphous or essentially amorphous after storage under various storage conditions (e.g., 25° C./60% RH, 25° C./protected, 40° C./75% RH, 40° C./protected, 50° C./80% RH, etc.) for a period of at least 1 week, or a period of at least 2 weeks, or a period of at least 3 weeks, or a period of at least 4 weeks or 1 month, or a period of at least 2 months, or a period of at least 3 months, or a period of at least 4 months, or a period of at least 5 months, or a period of at least 6 months, or a period of at least 7 months, or a period of at least 8 months, or a period of at least 9 months, or a period of at least 10 months, or a period of at least 11 months, or a period of at least 12 months or 1 year. In some embodiments, the ASDs of the disclosure may be amorphous or essentially amorphous under conditions of high temperature and humidity (e.g., 40° C./75% RH) for a period of at least 1 month, or a period of at least 2 months, or a period of at least 3 months, or a period of at least 6 months.

The dasatinib ASDs of the present disclosure can be characterized for water content, such as by using standard Karl Fischer coulometric titration methods. In some embodiments, the dasatinib ASDs may comprise a water content as assessed by Karl Fischer coulometric titration method of no more than 3%, or no more than 2.5%, or no more than 2%, or no more than 1.5%, or no more than 1%.

In some embodiments, the dasatinib ASDs may comprise a water content as assessed by Karl Fischer coulometric titration method of no more than 8%, or no more than 7%, or no more than 6%, or no more than 5%, or no more than 4.5%, or no more than 4%, or no more than 3.5%, or no more than 3%, or no more than 2.5%, or no more than 2%, or no more than 1.5%, or no more than 1%, after storage at 25° C./60% RH for 1 month, or 2 months, or 3 months, or 6 months. In some embodiments, the dasatinib ASDs may comprise a water content as assessed by Karl Fischer coulometric titration method of no more than 8%, or no more than 7%, or no more than 6%, or no more than 5%, or no more than 4.5%, or no more than 4%, or no more than 3.5%, or no more than 3%, or no more than 2.5%, or no more than 2%, after storage at 40° C./75% RH for 1 month, or 2 months, or 3 months, or 6 months.

Methods of Making Amorphous Solid Dispersions

The dasatinib ASDs of the present disclosure may be prepared by a variety of methods known in the art. Suitable methods generally include mixing, dissolving, or compounding the dasatinib and the one or more polymers and, if present, one or more other functional components (such as antioxidants, wetting agents, or solubilizers) to integrate the various components. In the practice of the various methods, the dasatinib may be introduced as dasatinib free base, or as a salt of dasatinib, or as a solvate or hydrate of dasatinib.

Suitable methods are generally known in the art, and include kneading, co-grinding, melting, melt extrusion, melt agglomeration, dropping, and the like. After the integration step, the material can be further processed by drying, grinding or crushing, sieving, etc.

In the practice of certain methods, dasatinib and the one or more polymers (and other functional components, if present) may be mixed or dissolved with one or more solvents to provide a liquid feedstock. Suitable solvents may include, but are not limited to, water; an alcohol, such as ethanol, methanol, propanol or isopropanol; an ether, such as ethyl ether or methyl tert-butyl ether; acetonitrile; tetrahydrofuran or methyl tetrahydrofuran; an acetate, such as methyl acetate or ethyl acetate; a ketone, such as acetone or 2-butanone (methyl ethyl ketone, or "MEK"); toluene; ethyl formate; 1,4-dioxane; dimethylsulfoxide; N-methyl 2-pyrrolidone; volatile halogenated solvents such as chloroform or dichloromethane; and combinations thereof. The mixing or dissolving of these contents may be by methods known in the art. For example, the contents may be mixed by manually mixing, or may be mixed with a mixing device continuously, periodically, or a combination thereof. Examples of mixing devices may include, but are not limited to, a magnetic stirrer, shaker, a paddle mixer, homogenizer, and any combination thereof.

After the dasatinib and the one or more polymers (and other functional components, if present) are mixed, the liquid feedstock may be formed into an ASD, such as through solvent evaporation, lyophilization, precipitation or co-precipitation, spray drying, electrospraying, supercritical fluid extraction, etc. These methods are known and commonly understood in the art.

In certain embodiments of the disclosure, the liquid feedstock may be formed into an ASD through electrospraying. Electrospraying, which has also been referred to as electrohydrodynamic atomization, has been used to produce amorphous solid dispersion particles on a micron or submicron scale from suitable liquid feedstocks.

In one suitable electrospraying technique, the liquid feedstock is emitted through one or more nozzles toward a substrate in the presence of an electric potential applied between the nozzles and the substrate. The liquid feedstock experiences electrical shear stress due to the applied potential. When the shear stress overcomes the surface tension of the liquid feedstock, droplets are emitted from the tips of the nozzles.

Conditions are controlled such that a cone jet of droplets is emitted at the tip of the nozzles. The droplets take on an electric charge and repel one another, which prevents their coagulation and promotes self-dispersion. The charged droplets accelerate toward the substrate as a result of the applied electric field.

During the short flight path, the solvent "flashes off" from the charged droplets. This fast evaporation creates a situation in which the charged droplets shrink in size but increase in charge density. At a critical limit, the droplets will break up into yet smaller droplets. An essentially monodisperse population of fine droplets is ultimately produced. The size of the droplets can range from sub-micron to several microns.

The essentially complete evaporation of solvent from the charged droplets results in the formation of relatively uniform particles of the non-volatile components from the liquid feedstock. The evaporation process occurs at a timescale that does not permit crystallization of the non-volatile components. Additionally, evaporative cooling associated with the extremely rapid solvent evaporation contributes a quenching effect to preserve the particles in an amorphous state. Furthermore, electrospray conditions can be selected and the system can be configured such that the amorphous particles contain little residual solvent.

In some embodiments of the disclosure, the liquid feedstock may be formed into an ASD using electrospray techniques and/or devices. Suitable methods and equipment are described, for example, in U.S. Pat. Nos. 6,746,869, 6,764,720, 7,279,322, 7,498,063, 7,951,428, 7,972,661, 8,992,603, 9,040,816, 9,050,611, 9,108,217, 9,642,694, 10,562,048, U.S. Patent Publication No. 2014-0158787, U.S. Patent Publication No. 2015-0190253, U.S. Patent Publication No. 2016-0038968, U.S. Patent Publication No. 2016-0175881, U.S. Patent Publication No. 2016-0235677, U.S. Patent Publication No. 2019-0193109, and U.S. Patent Publication No. 2020-0179963.

As noted above, by using an electrospray technique, the median diameter of the dasatinib ASD particle distribution may be from 0.1 µm to 10 µm, or from 0.2 µm to 5 µm, or from 0.5 µm to 2 µm. It should further be noted that the dasatinib in electrosprayed amorphous particles is generally not considered to be solvated. Even where the liquid feedstock may have been prepared using a solvate form of dasatinib (such as dasatinib monohydrate), the solvate is understood to flash off with the other solvents, and the electrosprayed amorphous particles comprise non-solvated dasatinib (such as anhydrous dasatinib).

In some embodiments, the electrospray technique may be performed at room temperature. In certain embodiments, no heated air is used. In other embodiments, the liquid feedstock is held at an elevated temperature during the electrospray process.

In some embodiments, the electrospray technique may be performed using one or more capillary nozzles. In certain embodiments, the electrospray technique does not use pneumatic nozzles such as nozzles that rely on kinetic energy; pressure nozzles; rotary nozzles or nozzles that rely on centrifugal energy; or ultrasonic nozzles such as nozzles that rely on acoustic energy. In some embodiments, the electrospray technique generates a yield of over 85%, or over 90%, or over 95%, or over 98%.

In other embodiments, the liquid feedstock may be formed into an ASD through spray drying. Generally speaking, spray drying involves the atomization of a liquid feedstock into very small droplets within a hot drying gas. The feedstock is pumped or otherwise propelled through a nozzle or other atomizing apparatus to form droplets within a drying chamber. Within the drying chamber, the droplets are exposed to an environment of the heated drying gas (usually flowing air or nitrogen), leading to flash drying of the droplets (by evaporative removal of solvent) and resultant production of solid particles. The dried particles are collected, generally at an output port in the drying chamber.

Various apparatus and methods of spray drying may be employed to form an ASD of the disclosure. In the practice of the present disclosure, the median diameter of the ASD particle distribution achieved by spray drying may be from 1 µm to 40 µm, or from 2 µm to 25 µm, or from 3 µm to 20 µm.

In some embodiments, the process for forming an ASD does not require a secondary drying step, i.e., a drying step that occurs after the particles are produced. In other embodiments, a secondary drying step is employed to further remove most or all of the residual solvents. The secondary drying step can be done under suitable conditions that allow for the removal of solvent but do not result in the recrystallization of the dasatinib. For example, a secondary drying step can be done below a glass transition temperature. A secondary drying step can also be done at reduced pressure. A combination of elevated temperature and reduced pressure can also be used for a secondary drying step.

Pharmaceutical Compositions

An aspect of the present disclosure relates to pharmaceutical compositions comprising dasatinib ASD. The pharmaceutical compositions of the present disclosure may be in a dosage form appropriate for oral administration. In some embodiments, the pharmaceutical compositions may be in the form of granules, or may be prepared as granules as an intermediate step to forming another oral dosage form, such as tablets, sprinkles, or pellets. In some embodiments, the pharmaceutical compositions may be in a solid dosage form for oral administration, such as a capsule, tablet, sprinkle, or pellet. The pharmaceutical composition may also be in the form of an aqueous or nonaqueous suspension or solution. Such compositions may be prepared using known excipients and known preparation methods.

The compositions may comprise a dasatinib ASD of the present disclosure and one or more pharmaceutically acceptable excipients, such as one or more solubilizers, one or more buffering agent(s), one or more pH-adjusting agents, one or more surfactants, one or more antioxidants, and/or one or more carriers. Pharmaceutical compositions in the form of solid oral dosage forms may also comprise one or more filling agents, one or more binding agents, one or more lubricants, one or more disintegrants, and/or other conventional excipients such as one or more glidants, for example.

The pharmaceutical compositions of the present disclosure may be prepared using methods known in the art. For example, the dasatinib ASD and the one or more pharmaceutically acceptable additives may be mixed by simple mixing, or may be mixed with a mixing device continuously, periodically, or a combination thereof. Examples of mixing devices may include, but are not limited to, a magnetic stirrer, shaker, a paddle mixer, homogenizer, and any combination thereof.

Solubilizers that may be used in the pharmaceutical compositions of the present disclosure include, but are not limited to, polyvinyl caprolactam-polyvinyl acetate-polyethylene glycol copolymer (SOLUPLUS), d-α-tocopherol acid polyethylene glycol (PEG) 1000 succinate (TPGS), PEG-40 hydrogenated castor oil (CREMOPHOR RH40), PEG-35 castor oil (CREMOPHOR EL), PEG-40 stearate (MYRJ 540), hard fat (such as GELUCIRE 33/01), polyoxylglycerides (such as GELUCIRE 44/14), stearoyl polyoxylglycerides (such as GELUCIRE 50/13), PEG-8 caprylic/capric glycerides (such as LABRASOL) and poloxamers (such as PLURONIC, KOLLIPHOR).

In some embodiments, the pharmaceutical compositions may comprise a dasatinib ASD and one or more pharmaceutically acceptable excipients, with the proviso that the pharmaceutically acceptable excipients do not comprise polyvinyl caprolactam-polyvinyl acetate-polyethylene glycol graft co-polymer (e.g., SOLUPLUS).

Buffering agents that that may be used in the pharmaceutical compositions of the present disclosure include, but are not limited to, triethylamine, meglumine, diethanolamine, ammonium acetate, arginine, lysine, histidine, a phosphate buffer (e.g., sodium phosphate tribasic, sodium phosphate dibasic, sodium phosphate monobasic, or o-phosphoric acid), sodium bicarbonate, a Britton-Robinson buffer, a Tris buffer (containing Tris(hydroxymethyl)-aminomethane), a HEPES buffer (containing N-(2-hydroxyethyl)piperazine-N'-(2-ethanesulfonic acid), acetate, a citrate buffer (e.g., citric acid, citric acid anhydrous, citrate monobasic, citrate dibasic, citrate tribasic, citrate salt), ascorbate, glycine, glutamate, lactate, malate, formate, sulfate, and mixtures thereof.

Further, pH-adjusting agents that that may be used in the pharmaceutical compositions of the present disclosure include pharmaceutically acceptable acids or bases. For example, acids may include, but are not limited to, one or more inorganic mineral acids such as hydrochloric, hydrobromic, sulfuric, phosphoric, nitric, and the like; or one or more organic acids such as acetic, succinic, tartaric, ascorbic, citric, glutamic, benzoic, methanesulfonic, ethanesulfonic, trifluoroacetic, and the like. The bases may be one or more inorganic bases or organic bases, including, but not limited to, alkaline carbonate, alkaline bicarbonate, alkaline earth metal carbonate, alkaline hydroxide, alkaline earth metal hydroxide, or amine. For example, the inorganic or organic base may be an alkaline hydroxide such as lithium hydroxide, potassium hydroxide, cesium hydroxide, sodium hydroxide, or the like; an alkaline carbonate such as calcium carbonate, sodium carbonate, or the like; or an alkaline bicarbonate such as sodium bicarbonate, or the like; the organic base may also be sodium acetate.

Surfactants that that may be used in the pharmaceutical compositions of the present disclosure may include, but are not limited to, sodium lauryl sulfate, docusate sodium, dioctyl sodium sulfosuccinate, dioctyl sodium sulfonate, benzalkonium chloride, benzethonium chloride, lauromacrogol 400, polyoxyl 40 stearate, polyoxyethylene hydrogenated castor oil (e.g., polyoxyethylene hydrogenated castor oil 10, 50, or 60), glycerol monostearate, polysorbate (e.g., polysorbate 40, 60, 65, or 80), sucrose fatty acid ester, methyl cellulose, polyalcohols and ethoxylated polyalcohols, thiols (e.g., mercaptans) and derivatives, poloxamers, polyethylene glycol-fatty acid esters (e.g., KOLLIPHOR RH40, KOLLIPHOR EL), lecithins, and mixtures thereof.

Antioxidants that that may be used in the pharmaceutical compositions of the present disclosure include, but are not limited to, acetylcysteine, ascorbyl palmitate, BHA, BHT, monothioglycerol, potassium nitrate, sodium ascorbate, sodium formaldehyde sulfoxylate, sodium metabisulfite, sodium bisulfate, vitamin E or a derivative thereof, propyl gallate, EDTA (e.g., disodium edetate), DTPA, bismuth sodium triglycollamate, or a combination thereof. Antioxidants may also comprise amino acids such as methionine, histidine, cysteine and those carrying a charged side chain, such as arginine, lysine, aspartic acid, and glutamic acid. Any stereoisomer (e.g., l-, d-, or a combination thereof) of any particular amino acid (e.g., methionine, histidine, arginine, lysine, isoleucine, aspartic acid, tryptophan, threonine and combinations thereof) or combinations of these stereoisomers, may be present so long as the amino acid is present either in its free base form or its salt form.

Carriers that that may be used in the pharmaceutical compositions of the present disclosure include, but are not limited to, water, salt solutions (e.g., Ringer's solution and the like), alcohols, oils, gelatins, and carbohydrates such as lactose, amylose or starch, fatty acid esters, methylcellulose, hydroxyethylcellulose, hydroxypropyl cellulose, polyvinyl pyrrolidine, and mixtures or solutions including any of the foregoing. The carrier may be used in combination with a buffering agent.

In some embodiments, the composition of the present disclosure may comprise a carrier at a pH of 5 to 9, or 6 to 8. In certain embodiments, the composition may comprise a carrier having a neutral pH. In certain embodiments, the pH of the carrier may be at or near physiological pH.

In some embodiments, the pharmaceutical compositions of the present disclosure may include other suitable pharmaceutical additives such tonicity-adjusting agents, preservatives, emulsifiers, sweeteners, flavoring agents, suspending agents, thickening agents, colors, viscosity regulators, stabilizers, and osmo-regulators.

Pharmaceutical compositions in solid form may comprise one or more filling agents, one or more binding agents, one or more lubricants, one or more disintegrants, and/or other conventional excipients such as one or more glidants, for example.

Suitable filling agents include acacia, calcium carbonate, calcium sulfate, calcium sulfate dihydrate, compressible sugar, dibasic calcium phosphate anhydrous (e.g., FUJICALIN, EMCOMPRESS), dibasic calcium phosphate dihydrate, tribasic calcium phosphate, monobasic sodium phosphate, dibasic sodium phosphate, lactose monohydrate, lactose anhydrous, magnesium oxide, magnesium carbonate, silicon dioxide, magnesium aluminum silicate, maltodextrin, mannitol, methyl cellulose, microcrystalline cellulose (e.g., AVICEL PH-101, AVICEL PH-102), powdered cellulose, starches, sorbitol, dextrose, dextrates, dextrin, sucrose, xylitol and mixtures thereof.

Suitable binding agents include various celluloses and cross-linked polyvinylpyrrolidone, microcrystalline cellulose (e.g., AVICEL PH-101, AVICEL PH-102, AVICEL PH-105), or silicified microcrystalline cellulose (e.g., PROSOLV SMCC), for example.

One or more lubricants may be included to reduce friction with and adherence to processing equipment during processing. Examples of suitable lubricants include, but are not limited to, magnesium stearate, calcium stearate, zinc stearate, stearic acid, stearyl alcohol, glyceryl monostearate, sodium stearyl fumarate, talc, glyceryl behenate, sodium benzoate, sodium lauryl sulfate, and the like. When included, the one or more lubricant is generally present in the range of 0.1% to 5%, by weight of the pharmaceutical composition. In some embodiments, the one or more lubricant is generally present in the range of 0.25% to 2%, by weight of the pharmaceutical composition. In certain embodiments, the lubricant is magnesium stearate.

Suitable disintegrants in the practice of the disclosure include natural, modified or pre-gelatinized starch, sodium starch glycolate, sodium carboxymethyl cellulose, calcium carboxymethyl cellulose, croscarmellose sodium, crospovidone, polyvinylpolypyrrolidone, and mixtures thereof.

Glidants are employed to improve flow properties of a powder or granule mixture prior to further processing (such as tablet compression, for example). Suitable glidants that may be employed in the compositions of the present disclosure include, but are not limited to, colloidal silica (e.g., hydrophobic colloidal silica, such as AEROSIL), silica gel, precipitated silica, and the like. When included, the one or more glidant is generally present in the range of 0.1% to 5%, by weight of the pharmaceutical composition. In some embodiments, the one or more glidant is generally present in the range of 0.25% to 2%, by weight of the pharmaceutical composition.

In some cases, a single excipient may provide more than one function. For example, microcrystalline cellulose (when present) can function as both a filling agent and a binding agent. Alternatively, such multi-functional excipients can be used in combination with other functional excipients. (For example, microcrystalline cellulose may be used with other filling agents and/or other binding agents.)

In some embodiments, the pharmaceutical compositions may be in the form of granules, or may be prepared as granules as an intermediate step to forming another oral dosage form, such as a tablet or pellet, or as a fill for a capsule. In some embodiments, granules may comprise one or more of the pharmaceutically acceptable excipients described above. In certain embodiments, the granules may comprise the ASD in an amount of 20%-70% by weight of the granule; one or more filling agents in an amount of 20% to 70% by weight of the granule; one or more disintegrants in an amount of 2%-10% by weight of the granule; and one or more lubricants in an amount of 0.2%-5% by weight of the granule. In particular embodiments, the granules may comprise the components as set forth in Table 1.

TABLE 1

Components of an exemplary granule formulation in accordance with particular embodiments of the disclosure.

| Component | % By Weight of the Granule |
| --- | --- |
| Dasatinib ASD | 30-70% |
| Dibasic Calcium Phosphate | 20-50% |
| Microcrystalline Cellulose | 5-20% |
| Croscarmellose Sodium | 2-10% |
| Hydrophobic Colloidal Silica | 0.2-5% (optional) |
| Magnesium stearate | 0.2-5% (optional) |

In some embodiments, the pharmaceutical compositions are in the form of a tablet. In certain embodiments, the tablet may comprise the ASD in an amount of 20%-60% by weight of the tablet; one or more filling agents in an amount of 40%-80% by weight of the tablet; one or more disintegrants in an amount of 1%-10% by weight of the tablet; and one or more lubricants in an amount of 0.25%-5% by weight of the tablet.

In particular embodiments, the amount of granule in the tablet may depend on the dasatinib drug load of the ASD that is used to prepare the granules. In other words, a greater amount of drug load in the ASD results in a greater amount of dasatinib in the granules, and therefore a smaller amount of granules is needed for the tablets. By way of examples only, Tables 2 and 3 list components of exemplary tablet formulations comprising granules that have ASD at drug loads of 60% and 80%, respectively.

TABLE 2

Components of an exemplary tablet formulation comprising granules of dasatinib ASD particles (60% drug load) in accordance with particular embodiments of the disclosure.

| Component | | % By Weight of the Tablet | |
| --- | --- | --- | --- |
| Granules Comprising Dasatinib ASD (60% drug load) | | 50-90% | |
| Other Excipients in the Tablet | Microcrystalline Cellulose | 5-40% | 10-50% |
| | Croscarmellose Sodium | 1-10% | |
| | Hydrophobic Colloidal Silica | 0.5% | |
| | Magnesium stearate | 0.5% | |

TABLE 3

Components of an exemplary tablet formulation comprising granules of dasatinib ASD particles (80% drug load) in accordance with particular embodiments of the disclosure.

| Component | | % By Weight of the Tablet | |
|---|---|---|---|
| Granules Comprising Dasatinib ASD (80% drug load) | | 40-80% | |
| Other Excipients in the Tablet | Microcrystalline Cellulose | 10-50% | 20-60% |
| | Croscarmellose Sodium | 1-10% | |
| | Hydrophobic Colloidal Silica | 0.5% | |
| | Magnesium stearate | 0.5% | |

Pharmaceutical compositions of the disclosure in the form of a tablet may be prepared using methods known in the art. For example, the dasatinib ASD and the one or more pharmaceutically acceptable additives may be blended to provide a tableting blend by hand or bag blending, or using a suitable device. Examples of suitable blending devices may include, but are not limited to, a tumble blender, v-blender, acoustic blender, paddle mixer, screw mixer, and the like.

Suitable tableting blends may then be compressed into tablets weighing from 100 to 1000 mg using, for example, a manual tablet press or a conventional mechanical tablet press. Compression force is selected to achieve desired mechanical properties of the tablet without compromising performance.

In some embodiments, it may be desirable to form granules as an intermediate step to forming a tableting blend. Granules typically have improved flow, handling, blending, and compression properties relative to ungranulated materials. The granules may be prepared from the ASD particles by processes known in the art, including wet granulation and dry granulation. In some embodiments, a granule blend is formed by dry-blending granule components, and then the granule blend is densified using a roller compactor which typically forms ribbons of material. The ribbons are then reduced in size by milling to form granules.

Wet granulation techniques may also be employed to form granules, provided the solvents and process selected do not alter the properties of the ASD. Improved wetting, disintegrating, dispersing and dissolution properties may be obtained by the inclusion of suitable excipients, as described above.

The granule blend (and accordingly the resulting granules) can include some or all of the components of the tablet. In some embodiments, the granules may comprise one of more of the pharmaceutically acceptable excipients described above. After granulation, the granules can be included into a tableting blend and compressed into tablets, as described above.

The pharmaceutical compositions of the present disclosure may demonstrate a desirable level of physical and/or chemical stability over some suitable period of time, and optionally under accelerated conditions. The stability of the pharmaceutical compositions can be assessed by different measures. For instance, the pharmaceutical compositions may demonstrate chemical stability by having a particular assay value or a particular level of total related substances (e.g., impurities), measured after storage under accelerated conditions over a specified period of time. In some embodiments, the pharmaceutical compositions may be amorphous as assessed using XRD (i.e., no crystalline character detected) after storage under the specified conditions.

In some embodiments, the pharmaceutical compositions may be essentially amorphous as assessed using XRD, after storage under the specified conditions. The storage conditions may be one or more of 25° C./60% RH, or 30° C./65% RH, or 40° C./75% RH. The period of time may be one or more of 1 week, or 2 weeks, or 1 month, or 2 months, or 3 months, or 4 months, or 6 months, or 9 months, or 12 months, or 15 months, or 18 months, or 21 months, or 2 years, or any period of time therebetween.

In some embodiments, pharmaceutical compositions of the present disclosure are "gastric acid-insensitive compositions," as further described below. In some embodiments, pharmaceutical compositions of the present disclosure are "improved variability compositions," as further described below.

Treatment of Proliferative Disorders

Aspects of the present disclosure relate to uses of the dasatinib ASDs of the present disclosure, or pharmaceutical compositions comprising the ASDs. In the practice of such embodiments of the present disclosure, dasatinib ASDs and pharmaceutical compositions may be suitably administered to subjects or to patients.

In some embodiments, the dasatinib ASD or pharmaceutical composition is administered to a subject. The subject in the methods of the present disclosure may be a mammal, which includes, but is not limited to, a human, monkey, cow, hog, sheep, horse, dog, cat, rabbit, rat, and mouse. In certain embodiments, the subject is a human. As used herein, the phrase "healthy human subject" means a human that is generally healthy and is not being treated for the disease or condition for which the pharmaceutically active component (e.g., dasatinib) is generally used for therapy. Selection of suitable healthy human subjects for pharmacokinetic assessment is within the expertise of one skilled in the art of clinical trial design.

In other embodiments, the dasatinib ASD or pharmaceutical composition is administered to a human patient. The human patient may be adult or of a pediatric age, e.g., younger than 17 years old. In certain embodiments, the human patient is 1 year of age or older. As used herein, a "patient" is a subject, particularly a human, who is being treated for a disease or condition for which the pharmaceutically active component (e.g., dasatinib) is generally used for therapy.

An aspect of the present disclosure relates to the use of the dasatinib ASDs of the present disclosure or pharmaceutical compositions of the present disclosure to treat a proliferative disorder. Some embodiments relate to a method of treating a proliferative disorder, the method comprising administering an ASD of the present disclosure, or a pharmaceutical composition of the present disclosure, to a patient in need thereof. Some embodiments relate to a use of a dasatinib ASD or a pharmaceutical composition of the present disclosure for treating a proliferative disorder in a patient in need thereof, the use comprising administering the dasatinib ASD or pharmaceutical composition to the patient. Some embodiments relate to a dasatinib ASD or a pharmaceutical composition of the present disclosure for use in treating a proliferative disorder in a patient in need thereof, the use comprising administering the dasatinib ASD or the pharmaceutical composition to the patient. Some embodiments relate to a use of a dasatinib ASD or pharmaceutical composition of the present disclosure in the manufacture of a medicament for treating a proliferative disorder.

In one aspect, the present disclosure relates to a method of treating a proliferative disorder in a patient in need thereof, the method comprising administering a therapeutically effective amount of an ASD of the present disclosure or of a pharmaceutical composition of the present disclosure to the patient.

The proliferative disorder may be cancer. Examples of such proliferative disorders may include, but are not limited to, leukemias such as acute lymphocytic leukemia (or acute lymphoblastic leukemia), acute myeloid leukemia (or acute myelogenous leukemia), chronic lymphocytic leukemia (or chronic lymphoblastic leukemia), chronic myeloid leukemia (or chronic myelogenous leukemia); age-related macular degeneration and diabetic retinopathy, anal and oral cancers, angiosarcoma, basal cell carcinoma and squamous cell carcinoma, bladder cancer, brain cancer, breast cancer, cancer of the central nervous system, cervical, cervix uteri cancer, choriocarcinoma, colon cancer, gastrointestinal stromal tumor, corpus uteri cancer, esophageal cancer, Ewing's Sarcoma, eye or ocular cancer, head and neck cancer, hemangioendothelioma, hemangiomas and lymphangiogenesis, Kaposi's Sarcoma, larynx cancer, liver cancer, lung cancer, lymphoma, mouth/pharynx cancer, multiple myeloma; cardiac hypertrophy, neuroblastoma, neurofibromatosis, ovary cancer, pancreatic cancer, prostate cancer, rectal cancer, renal cancer, rhabdomyosarcoma, skin melanoma, small cell lung cancer, stomach cancer, testis cancer, throat cancer, tuberous sclerosis, and Wilms Tumor.

In certain embodiments, the proliferative disorder may be Philadelphia chromosome-positive ("Ph+") chronic myeloid leukemia ("CML") in chronic phase. In certain embodiments, the proliferative disorder may be chronic, accelerated, or myeloid or lymphoid blast phase Ph+ CML with resistance or intolerance to prior therapy including imatinib. In certain embodiments, the proliferative disorder may be Ph+ acute lymphoblastic leukemia ("ALL") with resistance or intolerance to prior therapy. In some embodiments, the proliferative disorder may be Ph+ ALL, and dasatinib may be administered in combination with chemotherapy.

In the methods and uses of the present disclosure, a therapeutically effective amount of the dasatinib ASD or the pharmaceutical composition of the present disclosure will be based on, among other factors, the route of administration, the age and size of the patient, and the proliferative disorder being treated. As used herein, the term "therapeutically effective amount" means that amount that is expected to elicit the biological or medical response that is being sought by a clinician.

In some embodiments, a therapeutically effective amount may be 0.01 to 10 mg/kg/day, or 0.05 to 7 mg/kg/day of dasatinib. In other embodiments, a therapeutically effective amount may be fixed dose. For instance, the fixed dose may be 5 mg to 400 mg, or 10 mg to 300 mg, or 10 mg to 200 mg, per day of dasatinib. In certain embodiments, the fixed dose may be 10 mg, or 20 mg, or 25 mg, or 30 mg, or 40 mg, or 50 mg, or 60 mg, or 70 mg, or 75 mg, or 80 mg, or 90 mg, or 100 mg, or 110 mg, or 120 mg, or 125 mg, or 130 mg, or 140 mg, or 150 mg, or 160 mg, or 170 mg, or 175 mg, or 180 mg, or 190 mg, or 200 mg, per day of dasatinib. Depending on the treatment regimen, the quantity of dasatinib dosed per day may be dosed all at once (once-daily dosing), or may be divided and dosed more frequently (such as twice-per-day dosing).

As described further below, pharmaceutical compositions of the present disclosure may provide enhanced or otherwise desirable bioavailability under a variety of administration conditions. The term "bioavailability" refers to the rate and extent to which an active ingredient is absorbed from a pharmaceutical composition and becomes available at the site of action. In the case of orally administered pharmaceuticals, bioavailability is generally assessed by monitoring a subject's blood plasma over time for the presence of an active ingredient (or suitable surrogate, such as a metabolite) after administration of a pharmaceutical composition, to evaluate the pharmacokinetic profile.

From the pharmacokinetic profile, certain relevant pharmacokinetic parameters can be established. Such pharmacokinetic parameters can include $C_{max}$, $T_{max}$, and/or AUC, for example. $C_{max}$ indicates the maximum observed plasma concentration over the observed time period. $T_{max}$ indicates the time point at which the maximum plasma concentration is observed.

AUC indicates the numerical area-under-the-curve ("AUC") for the concentration-time curve, and can be assessed for a specified time interval 0-t, denoted as $AUC_{0-t}$ (alternatively denoted as $AUC_t$). $AUC_{0-t}$ is generally obtained by numerical integration of the concentration-time curve over the period t=0 to the time "t" (e.g., $AUC_{0-24h}$ or $AUC_{24h}$ indicates the integral over the time period from t=0 to t=24 hours). $AUC_{0-last}$ (alternatively denoted as $AUC_{last}$) indicates the integral from t=0 to the last time point sampled in the observed time period. $AUC_{0-inf}$ (alternatively denoted as $AUC_{inf}$) indicates the integral from t=0 to t="infinity," which is determined by extrapolation of obtained data using commonly employed pharmacokinetic statistical modeling techniques.

Typically, plasma concentration data is log-transformed for analysis. For most pharmacokinetic analyses, data for a number of test subjects is pooled for analysis. When data is pooled, the relevant pharmacokinetic parameters may be expressed as a population geometric mean, in accordance with conventional pharmacokinetic statistical analyses and methods.

Administration of an ASD or pharmaceutical composition of the present disclosure can be characterized by the pharmacokinetic profile, or by the observed or calculated pharmacokinetic parameters resulting from the administration of the ASD or pharmaceutical composition at certain dosages to a subject or patient, under stated administration conditions.

By way of example only (and as further described below), administration of the ASD or pharmaceutical composition of the present disclosure under a fasted state or fasted conditions can be characterized by the pharmacokinetic profile resulting from the administration, or by observed pharmacokinetic parameters.

The phrase "fasted state" or "fasting conditions", as used herein for human subjects, refers to a subject being at least 2 hours, more suitably at least 4 hours, or more suitably at least 8 hours after the subject's previous meal. Preferably, the fasted state or fasting conditions follows an overnight fast of at least 10 hours. Similarly, "fasted state" or fasting conditions", as used herein, refers to the condition in which the subject has not eaten for at least two hours, more suitably at least 4 hours, or more suitably at least 8 hours; or the condition of the subject following an overnight fast of at least 10 hours. Moreover, the fasted state or fasting conditions may also require continued fasting for at least 1 hour, more suitably at least 2 hours, or more suitably at least 4 hours after the administration.

Likewise, reference to administration in a "fed state" or under "fed conditions" to a human subject, as used herein, refers to administration to the subject from 30 minutes after the subject starts ingesting a meal to 1 hour after complete ingestion of a meal. Similarly, "fed state" or "fed conditions"

refers to the condition of a subject 30 minutes after the subject starts ingesting a meal to 1 hour after complete ingestion of a meal.

Methods of Co-Administering with a Gastric Acid-Reducing Agent

In some embodiments, the dasatinib ASD or pharmaceutical composition according to the present disclosure can be co-administered with a gastric acid-reducing agent.

"Gastric acid-reducing agent" refers herein to any agent that acts to significantly reduce the amount of acid in a subject's or patient's stomach. Acid reduction can be due to suppression or blocking of acid secretion, or by neutralization of stomach acid. Examples of gastric acid-reducing agents include, but are not limited to, histamine-2 receptor antagonists (or $H_2$ antagonists) such as famotidine, cimetidine, nizatidine, and ranitidine; proton pump inhibitors (or PPIs) such as rabeprazole, esomeprazole, lansoprazole, omeprazole, pantoprazole, and dexlansoprazole; and antacids (which neutralize stomach acidity and thereby elevate gastric pH) such as aluminum hydroxide, magnesium hydroxide, sodium citrate, sodium carbonate, sodium bicarbonate, calcium carbonate, magnesium trisilicate, and the like.

The gastric acid-reducing agent may be administered in accordance with the dosing information that is known in the art for the agent, or according to a physician's instructions. A "standard dosage" as used herein indicates a dosage of the agent within a suitable range for the patient according to the dosing recommendation from the product's labeling, or according to the physician's instructions.

As used herein, "co-administration" (or "co-administered") refers to a situation in which a patient is being treated for two or more conditions simultaneously, by administration of two or more therapeutic agents. By way of example only, a patient may be treated for a proliferative disorder as described herein with dasatinib as a therapeutic agent, while also being treated for another condition, such as acid reflux or ulcers, with a second therapeutic agent such as a proton pump inhibitor. Since both therapeutic agents are dosed at least once daily, the two therapeutic agents are "co-administered," and consideration must be given to whether the administration of one of the therapeutic agents may affect the absorption or efficacy of the other.

In the context of the present disclosure, the phrase "can be co-administered" means that the two (or more) therapeutic agents of interest can be co-administered without a detrimental reduction in the exposure of dasatinib. "Without a detrimental reduction" indicates that the realized exposure would be similar to the exposure realized when the gastric acid-reducing agent is not co-administered. Any difference in the realized exposure would be insubstantial and/or therapeutically inconsequential. In contrast, when a detrimental reduction in exposure would be realized, then co-administration should be avoided. A "detrimental reduction" means a substantial and material reduction in the realized exposure. By way of example, if the realized exposure would be less than or equal to a level recognized as a sub-therapeutic exposure, then the co-administration would result in a detrimental reduction in exposure.

"Therapeutically relevant exposure" as used herein means an exposure that is comparable to the exposure that would be expected for a conventional commercially available immediate release formulation of dasatinib of corresponding strength, dosed according to its labeled instructions. By "comparable," it is meant that administration of the ASD or the pharmaceutical composition of the disclosure to the subject may provide $AUC_{0-t}$ (such as $AUC_{0-24h}$, $AUC_{last}$ or $AUC_{0-inf}$) and $C_{max}$, in the subject's plasma that produce a similar therapeutic effect. By way of example only, one way to determine a similar therapeutic effect is if the $AUC_{0-t}$ or $C_{max}$ is within the 80% to 125% bioequivalence criteria compared to administration of the conventional commercially available immediate release composition to the same subject, dosed according to its labeled instructions.

As used herein, the phrase "gastric acid-insensitive composition" indicates a pharmaceutical composition of the present disclosure that can be administered without regard to the patient or subject's gastric pH. A gastric acid-insensitive composition provides a therapeutically relevant exposure to the patient or subject across a range of gastric pH values. Accordingly, a gastric acid-insensitive composition can be administered whether or not the patient or subject has ingested a gastric acid-reducing agent, or whether or not the patient has a condition that causes elevated gastric pH (as further discussed below).

Embodiments of the disclosure relate to administering a gastric acid-reducing agent shortly before, concurrently with, or shortly after the dasatinib ASD or pharmaceutical composition of the disclosure. The term "shortly before" as used herein means that a gastric acid-reducing agent was administered to the subject 4 hours or less, or 3 hours or less, or 2 hours or less, or 1 hour or less, or 45 minutes or less, or 30 minutes or less, or 15 minutes or less, prior to the administration of the dasatinib ASD or pharmaceutical composition. The term "concurrently" or "concomitantly" as used herein means that a gastric acid-reducing agent was administered to the subject within 30 minutes or less, or within 20 minutes or less, or within 15 minutes or less, or within 10 minutes or less, or within 5 minutes or less, or within 4 minutes or less, or within 3 minutes or less, or within 2 minutes or less, or within 1 minute or less, or simultaneously, of the administration of the dasatinib ASD or pharmaceutical composition. The term "shortly after" as used herein means that a gastric acid-reducing agent was administered to the subject 4 hours or less, or 3 hours or less, or 2 hours or less, or 1 hour or less, or 45 minutes or less, or 30 minutes or less, or 15 minutes or less, after the administration of the dasatinib ASD or pharmaceutical composition.

In some embodiments, administration of an ASD or pharmaceutical composition of the present disclosure to a subject who was concurrently administered a gastric acid-reducing agent exhibits a pharmacokinetic profile of dasatinib that is similar to the pharmacokinetic profile resulting from administration of the ASD or pharmaceutical composition to a subject who was not concurrently administered a gastric acid-reducing agent. In certain embodiments, single administration to the subject of the ASD or pharmaceutical composition concurrently with a gastric-acid reducing agent results in an AUC of dasatinib that is within 50%, or within 40%, or within 30%, of the AUC of dasatinib that results from administration of the ASD without concurrent administration of the gastric acid-reducing agent. In certain embodiments, the AUC is $AUC_{0-24h}$. In other embodiments, the AUC is $AUC_{0-inf}$.

In some embodiments, single administration of an ASD or pharmaceutical composition of the present disclosure to a subject or patient who was concurrently, shortly before, or shortly after administered a gastric acid-reducing agent exhibits greater AUC and/or $C_{max}$ as compared to single administration of the standard commercial, immediate-release composition of dasatinib (e.g., SPRYCEL) to a subject or patient who was concurrently, shortly before, or shortly after administered a gastric acid-reducing agent. In certain embodiments, single administration of the ASD or pharmaceutical composition to a subject who was concurrently, shortly before, or shortly after administered a gastric-acid reducing agent results in an AUC and/or $C_{max}$ of dasatinib that is at least 80% greater, or at least 100% greater, or at least 150% greater, or at least 200% greater, than the AUC and/or $C_{max}$ of dasatinib that results from administration of the standard commercial, immediate-release composition of dasatinib concurrently, shortly before, or shortly after the gastric-acid reducing agent, where the ASD or pharmaceutical composition contains the same dosage as the standard commercial, immediate-release composition of dasatinib. In certain embodiments, the AUC is $AUC_{0-24h}$. In other embodiments, the AUC is $AUC_{0-inf}$.

In some embodiments, single administration of an ASD or pharmaceutical composition of the present disclosure to a subject or patient who was concurrently administered a gastric acid-reducing agent exhibits greater AUC and/or $C_{max}$ as compared to single administration of the standard commercial, immediate-release composition of dasatinib (e.g., SPRYCEL) to a subject or patient who was concurrently administered a gastric acid-reducing agent. In certain embodiments, single administration to the subject or patient of the amorphous solid dispersion or pharmaceutical composition concurrently with a gastric-acid reducing agent results in an AUC and/or $C_{max}$ of dasatinib that is at least 80% greater, or at least 100% greater, or at least 150% greater, or at least 200% greater, than the AUC and/or $C_{max}$ of dasatinib that results from administration of the standard commercial, immediate-release composition of dasatinib concurrently with the gastric-acid reducing agent, where the amorphous solid dispersion or pharmaceutical composition contains the same dosage as the standard commercial, immediate-release composition of dasatinib. In certain embodiments, the AUC is $AUC_{0-24h}$. In other embodiments, the AUC is $AUC_{0-inf}$.

In some embodiments, the dasatinib ASD or pharmaceutical composition of the present disclosure may be administered without regard to whether the subject is administered a gastric acid-reducing agent. Thus, the subject may be administered the dasatinib ASD or pharmaceutical composition no matter whether the subject was administered a gastric acid-reducing agent shortly before the dasatinib ASD or pharmaceutical composition; is being administered a gastric acid-reducing agent concurrently or shortly after the administration of the dasatinib ASD or pharmaceutical composition, or is not being administered a gastric acid-reducing agent at all.

Some embodiments relate to a method of delivering dasatinib to a subject without regard to whether the subject is administered a gastric acid-reducing agent, the method comprising administering the ASD or pharmaceutical composition of the disclosure to the subject. Some embodiments relate to a use of a dasatinib ASD or pharmaceutical composition of the present disclosure for delivering dasatinib to a subject without regard to whether the subject is administered a gastric acid-reducing agent, the use comprising administering the ASD or pharmaceutical composition to the subject. Some embodiments relate to a dasatinib ASD or pharmaceutical composition of the present disclosure for use in delivering dasatinib to a subject without regard to whether the subject is administered a gastric acid-reducing agent, the use comprising administering the ASD or pharmaceutical composition to the subject. Some embodiments relate to a use of a dasatinib ASD or pharmaceutical composition of the present disclosure in the manufacture of a medicament for delivering dasatinib to a subject without regard to whether the subject is administered a gastric acid-reducing agent, the delivery comprising administering the ASD or pharmaceutical composition to the subject. According to these embodiments, the subject may be administered the dasatinib ASD or pharmaceutical composition no matter whether the subject was administered a gastric acid-reducing agent shortly before the dasatinib ASD or pharmaceutical composition; is being administered a gastric acid-reducing agent concurrently or shortly after the administration of the dasatinib ASD or pharmaceutical composition; or is not being administered a gastric acid-reducing agent at all.

Embodiments of the disclosure relate to treatment regimens for treating a proliferative disorder in a patient in need thereof. In some embodiments, the regimen may comprise (a) administering to the patient a first dose, the first dose comprising a standard dosage of a proton pump inhibitor or $H_2$ antagonist; and (b) within 20 hours after the first dose, administering a second dose to the patient, the second dose comprising a therapeutically effective amount of a dasatinib ASD or pharmaceutical composition of the disclosure. In certain embodiments, the second dose is administered within 16 hours, or within 12 hours, or within 8 hours, or within 6 hours, or within 4 hours, or within 2 hours, after the first dose. In some embodiments, the regimen may comprise (a) administering to the patient a first dose, the first dose comprising a standard dosage of an antacid; and (b) within 2 hours before the first dose, administering a second dose to the patient, the second dose comprising a dasatinib ASD or pharmaceutical composition of the present disclosure. In some embodiments, the regimen may comprise (a) administering to the patient a first dose, the first dose comprising a standard dosage of an antacid; and (b) within 2 hours after the first dose, administering a second dose to the patient, the second dose comprising a dasatinib ASD or pharmaceutical composition of the present disclosure. In some embodiments, the regimen may comprise (a) administering to the patient a first dose, the first dose comprising a standard dosage of an antacid; and (b) within 2 hours before or within 2 hours after the first dose, administering a second dose to the patient, the second dose comprising a dasatinib ASD or pharmaceutical composition of the present disclosure.

Methods of Treating a Patient Having Elevated Gastric pH

The dasatinib ASDs or pharmaceutical compositions of the present disclosure may be suitably administered to subjects or patients with an elevated gastric pH. (In contrast, a conventional immediate-release composition of dasatinib would be unsuitable for therapeutic administration to a patient having elevated gastric pH.)

One aspect of the present disclosure relates to the use of the dasatinib ASDs or pharmaceutical compositions of the present disclosure to deliver dasatinib to a subject or patient with elevated gastric pH. Some embodiments relate to a method of delivering dasatinib to a subject with elevated gastric pH, the method comprising administering the ASD or pharmaceutical composition of the present disclosure to the subject or patient. Some embodiments relate to a use of a dasatinib ASD or pharmaceutical composition of the present disclosure for delivering dasatinib to a subject or patient with elevated gastric pH, the use comprising administering the ASD or pharmaceutical composition to the subject or patient. Some embodiments relate to a dasatinib ASD or pharmaceutical composition of the present disclosure for use in delivering dasatinib to a subject or patient with elevated gastric pH, the use comprising administering the ASD or pharmaceutical composition to the subject or patient. Some embodiments relate to a use of a dasatinib ASD or pharmaceutical composition of the present disclosure in the manufacture of a medicament for delivering dasatinib to a subject or patient with elevated gastric pH, the delivery comprising administering the ASD or pharmaceutical composition to the subject or patient.

As used herein, "gastric pH" refers to the pH inside a subject's or patient's stomach. Gastric pH may be considered as "elevated" when it is greater than 3.5, or greater than 4, or greater than 5, measured under fasting conditions. Gastric pH can be evaluated using standard methods, or an elevated gastric pH can be inferred from the known effects of, for example, treatment with gastric acid-reducing agents or an identified condition that regularly leads to a measurable elevated gastric pH.

In the practice of the present disclosure, subject or patient may have an elevated gastric pH due to different reasons, including, but not limited to, the subject or patient was administered a gastric acid-reducing agent, or the subject or patient may have a condition that leads to elevated gastric pH. Elevated gastric pH can result from conditions such as hypochlorhydria or achlorhydria, or infection by *Helicobacter pylori* (*H. pylori*) bacteria, for example.

As used herein, the phrase "chronically elevated" in reference to gastric pH means that the subject or patient experiences elevated gastric pH on a persistent or recurring basis. Chronically elevated gastric pH can result from, for example, conditions such as hypochlorhydria or achlorhydria, or infection by *Helicobacter pylori* bacteria. In particular, a conventional immediate-release composition of dasatinib would be unsuitable for therapeutic administration to a subject or patient having chronically elevated gastric pH, due to the likelihood of a detrimental reduction in the resulting exposure to dasatinib.

In some embodiments, the methods of the disclosure may contain a step of identifying a condition by which the patient's gastric pH is elevated (including conditions by which it is chronically elevated). Such a step may comprise diagnosing the underlying cause of the elevated gastric pH. It is known in medical practice how to diagnose hypochlorhydria or achlorhydria in patient, or how to test for a *Helicobacter pylori* bacteria infection. Hypochlorhydria or achlorhydria can be diagnosed, for example, by measuring stomach acid levels under different conditions. *Helicobacter pylori* bacterial infection can be diagnosed by an appropriate blood test, stool test, breath test, or scope test, for example.

In some embodiments, the dasatinib ASD or pharmaceutical composition may be administered to a subject or patient without regard to gastric pH. Thus, the subject or patient may be administered the dasatinib ASD or pharmaceutical composition no matter whether the subject or patient has normal gastric pH (i.e., gastric pH below 3.5, generally in the range 1.5 to 3) or has elevated gastric pH as described herein. This is beneficial when, for example, the subject or patient has gastric pH that fluctuates due to irregular or episodic use of gastric acid-reducing agents, or if the subject or patient has hypochlorhydria (resulting in a gastric pH that may fluctuate depending on factors such as whether the subject or patient has recently eaten).

In some embodiments, administration of an ASD or pharmaceutical composition of the present disclosure to a subject or patient who has elevated gastric pH exhibits a pharmacokinetic profile for dasatinib that is similar to the pharmacokinetic profile resulting from administration of the ASD or pharmaceutical composition to a subject or patient who has normal gastric pH. In certain embodiments, single administration of the ASD or pharmaceutical composition to a subject or patient with elevated gastric pH results in $AUC_{0-t}$ (such as $AUC_{0-24h}$, $AUC_{last}$ or $AUC_{0-inf}$) and/or $C_{max}$ of dasatinib that is within 50%, or within 40%, or within 30%, of the $AUC_{0-t}$ and/or $C_{max}$ of dasatinib that results from single administration of the ASD or pharmaceutical composition to a subject or patient with normal gastric pH. In certain embodiments, the $AUC_{0-t}$ is $AUC_{0-24h}$. In other embodiments, the $AUC_{0-t}$ is $AUC_{0-inf}$.

In certain embodiments, administration of the ASD or pharmaceutical composition of the present disclosure in a subject or patient with elevated gastric pH may provide $AUC_{0-t}$ (such as $AUC_{0-24h}$, $AUC_{last}$ or $AUC_{0-inf}$) and $C_{max}$ in the subject's or patient's plasma that are within the 80% to 125% bioequivalence criteria compared to administration of the conventional commercially available immediate-release composition dosed to subjects or patients with normal gastric pH. In certain embodiments, the $AUC_{0-t}$ is $AUC_{0-24h}$. In other embodiments, the $AUC_{0-t}$ is $AUC_{0-inf}$.

In the practice of the present disclosure, administration of an ASD or a pharmaceutical composition can provide enhanced exposure as compared to standard immediate-release compositions. In some embodiments, single administration of an ASD or pharmaceutical composition of the present disclosure to a subject or patient who has elevated gastric pH exhibits greater AUC and/or $C_{max}$ as compared to single administration of the standard commercial, immediate-release composition of dasatinib (e.g., SPRYCEL) to a subject or patient who has elevated gastric pH. (It should be understood that the same molar quantity or "label claim" of dasatinib is administered in each case.) In certain embodiments, the AUC is $AUC_{0-24h}$. In other embodiments, the AUC is $AUC_{0-inf}$. In certain embodiments, single administration of the ASD or pharmaceutical composition to a subject or patient with elevated gastric pH results in $AUC_{0-t}$ and/or $C_{max}$ of dasatinib that is at least 80% greater, or at least 100% greater, or at least 150% greater, or at least 200% greater, than the $AUC_{0-t}$ and/or $C_{max}$ of dasatinib that results from administration of the standard commercial, immediate-release composition of dasatinib to the subject or patient with elevated gastric pH. In certain embodiments, the $AUC_{0-t}$ is $AUC_{0-24h}$. In other embodiments, the $AUC_{0-t}$ is $AUC_{0-inf}$.

Further, one aspect of the present disclosure relates to the use of the dasatinib ASDs or pharmaceutical compositions of the present disclosure to deliver dasatinib to a subject without regard to the subject's gastric pH. Some embodiments relate to a method of delivering dasatinib to a subject without regard to the subject's gastric pH, the method comprising administering the ASD or pharmaceutical composition of the present disclosure to the subject. Some embodiments relate to a use of a dasatinib ASD or pharmaceutical composition of the present disclosure for delivering dasatinib to a subject without regard to the subject's gastric pH, the use comprising administering the ASD or pharmaceutical composition to the subject. Some embodiments relate to a dasatinib ASD or pharmaceutical composition of the present disclosure for use in delivering dasatinib to a subject without regard to the subject's gastric pH, the use comprising administering the ASD or pharmaceutical composition to the subject. Some embodiments relate to a use of a dasatinib ASD or pharmaceutical composition of the present disclosure in the manufacture of a medicament for delivering dasatinib to a subject without regard to the subject's gastric pH, the delivery comprising administering the ASD or pharmaceutical composition to the subject. According to these embodiments, the subject may be administered the dasatinib ASD or pharmaceutical composition no matter whether the subject has normal gastric pH or has elevated gastric pH as described herein.

Pharmaceutical Composition Having Improved Variability

The pharmaceutical compositions of the present disclosure may, in some embodiments, provide a less variable in vivo pharmacokinetic performance.

As used herein, the phrase "improved variability composition" refers to a composition of the present disclosure that exhibits a lower coefficient of variation with respect to one or more pharmacokinetic parameters when administered to healthy human subjects, as compared to the coefficient of variation observed for the standard commercial, immediate-release composition of dasatinib (e.g., SPRYCEL) when administered under similar conditions.

In some embodiments, the improved variability composition provides a coefficient of variation with respect to at least one pharmacokinetic parameter that is 30% lower, 25% lower, 20% lower, 15% lower, or 10% lower than the coefficient of variation observed for the standard commercial, immediate-release composition of dasatinib (e.g., SPRYCEL) when administered under similar conditions. The pharmacokinetic parameter can be any of $C_{max}$, $AUC_{last}$ and $AUC_{0-inf}$. In some embodiments, the improved variability composition provides an improvement with respect to $C_{max}$ and at least one of $AUC_{last}$ and $AUC_{0-inf}$. In other embodiments, the improved variability composition provides an improvement with respect to all of $C_{max}$, $AUC_{last}$ and $AUC_{0-inf}$.

In particular, it has been observed that a composition according to the present disclosure can provide a lower coefficient of variation for pharmacokinetic parameters when administered to healthy human subjects having normal gastric pH and in a fasted state. As shown in Example 8, a test composition exhibited a lower coefficient of variation with respect to $C_{max}$, $AUC_{last}$ and $AUC_{0-inf}$ under these conditions. The observed CV for the test composition was at least 30% lower for each of these parameters, as compared to the test composition.

Kit Comprising a Pharmaceutical Composition and a Package Insert

In some embodiments, the disclosure provides a kit containing a pharmaceutical composition according to any of the above-described aspects of the disclosure, as well as a package insert. As used herein, a "kit" is a commercial unit of sale, which may comprise a fixed number of doses of the pharmaceutical composition. By way of example only, a kit may provide a 30-day supply of dosage units of one or more fixed strengths, the kit comprising 30 dosage units, 60 dosage units, 90 dosage units, 120 dosage units, or other appropriate number according to a physician's instruction. As another example, a kit may provide a 90-day supply of dosage units.

As used herein, "package insert" means a document which provides information on the use of the pharmaceutical composition, safety information, and other information required by a regulatory agency. A package insert can be a physical printed document in some embodiments. Alternatively, a package insert can be made available electronically to the user, such as via the Daily Med service of the National Library of Medicines of the National Institute of Health, which provides up-to-date prescribing information. (See https://dailymed.nlm.nih.gov/dailymed/index.cfm.)

In some embodiments, the package insert informs a user of the kit that the pharmaceutical composition can be co-administered with a gastric acid-reducing agent. In some embodiments, the package insert does not comprise a warning that the pharmaceutical composition should not be co-administered with $H_2$ antagonists or proton pump inhibitors.

In some embodiments, the package insert may inform a user of the kit that an antacid can be co-administered with the pharmaceutical composition. In some embodiments, the package insert may not inform the user to use an antacid approximately 2 hours before or approximately 2 hours after administration of the pharmaceutical composition. In some embodiments, the package insert may inform the user that an antacid can be used within approximately 2 hours before or within approximately 2 hours after administration of the pharmaceutical composition.

In some embodiments, the package insert informs a user of the kit that the pharmaceutical composition can be suitably administered to a user having chronically elevated gastric pH. In some embodiments, the package insert informs a user of the kit that the pharmaceutical composition can be suitably administered to a patient diagnosed with or afflicted by achlorhydria or hypochlorhydria. In some embodiments, the package insert informs a user of the kit that the pharmaceutical composition can be suitably administered to a patient diagnosed with or afflicted by *Helicobacter pylori* infection.

The present disclosure will be further illustrated and/or demonstrated in the following Examples, which are given for illustration/demonstration purposes only and are not intended to limit the disclosure in any way.

EMBODIMENTS OF THE DISCLOSURE INCLUDE

Embodiment ASD1 is an amorphous solid dispersion comprising dasatinib and one or more polymers.

Embodiment ASD2 is an amorphous solid dispersion comprising dasatinib and one or more polymers; wherein the dasatinib and the one or more polymers are present in the amorphous solid dispersion in a w/w ratio of 30:70 to 95:5 (dasatinib:polymer). Embodiment ASD3 is an amorphous solid dispersion comprising dasatinib and one or more polymers, wherein the dasatinib and the one or more polymers are present in the amorphous solid dispersion in a w/w ratio of 40:60 to 90:10 (dasatinib:polymer). Embodiment ASD4 is an amorphous solid dispersion comprising dasatinib and one or more polymers, wherein the dasatinib and the one or more polymers are present in the amorphous solid dispersion in a w/w ratio of 40:60 to 70:30 (dasatinib:polymer). Embodiment ASD5 is an amorphous solid dispersion comprising dasatinib and one or more polymers, wherein the dasatinib and the one or more polymers are present in the amorphous solid dispersion in a w/w ratio of 70:30 to 95:5 (dasatinib:polymer).

Embodiment ASD6 is the amorphous solid dispersion according to any of Embodiments ASD1 to ASD5, wherein the one or more polymers exhibits pH-dependent solubility. Embodiment ASD7 is the amorphous solid dispersion according to any of Embodiments ASD1 to ASD6, wherein the one or more polymers comprises a methacrylic acid and ethyl acrylate copolymer. Embodiment ASD8 is the amorphous solid dispersion according to any of Embodiments ASD1 to ASD7, wherein the one or more polymers consists essentially of a methacrylic acid and ethyl acrylate copolymer. Embodiment ASD9 is the amorphous solid dispersion according to any of Embodiments ASD1 to ASD8, wherein the one or more polymers comprise a methacrylic acid and ethyl acrylate copolymer that is insoluble in an aqueous medium at pH of 5 or lower, and soluble in an aqueous medium at pH 5.5 or greater. Embodiment ASD10 is the amorphous solid dispersion according to any of Embodiments ASD1 to ASD9, wherein the one or more polymers comprises a copolymer of dimethylaminoethyl methacrylate, butyl methacrylate, and methyl methacrylate. Embodiment ASD11 is the amorphous solid dispersion according to any of Embodiments ASD1 to ASD10, wherein the one or more polymers consists essentially of a copolymer of dimethylaminoethyl methacrylate, butyl methacrylate, and methyl methacrylate.

Embodiment ASD12 is the amorphous solid dispersion according to any of Embodiments ASD1 to ASD11, wherein the one or more polymers comprises a hydroxypropyl methylcellulose. Embodiment ASD13 is the amorphous solid dispersion according to any of Embodiments ASD1 to ASD12, wherein the one or more polymers consists essentially of a hydroxypropyl methylcellulose. Embodiment ASD14 is the amorphous solid dispersion according to any of Embodiments ASD1 to ASD13, wherein the one or more polymers comprise a hydroxypropyl methylcellulose characterized by a methoxyl substitution of 28 to 30% and a hydroxypropoxyl substitution of 7 to 12%. Embodiment ASD15 is the amorphous solid dispersion according to any of Embodiments ASD1 to ASD14, wherein the one or more polymers comprise a hydroxypropyl methylcellulose characterized by a viscosity of about 2 to about 18 mPa·s, as determined at 20° C. for a 2% solution in water. Embodiment ASD16 is the amorphous solid dispersion according to any of Embodiments ASD1 to ASD15, wherein the one or more polymers comprise a hydroxypropyl methylcellulose characterized by a number average molecular weight ($M_n$) of about 20 kDa or lower.

Embodiment ASD17 is the amorphous solid dispersion according to any of Embodiments ASD1 to ASD16 wherein the amorphous solid dispersion consists essentially of dasatinib and the one or more polymers.

Embodiment ASD18 is the amorphous solid dispersion according to any of Embodiments ASD1 to ASD17, wherein the amorphous solid dispersion comprises one or more antioxidants. Embodiment ASD19 is the amorphous solid dispersion according to any of Embodiments ASD1 to ASD18, wherein the amorphous solid dispersion comprises one or more antioxidants that are present in an amount of about 0.001% to about 2.0% by weight of the amorphous solid dispersion. Embodiment ASD20 is the amorphous solid dispersion according to any of Embodiments ASD1 to ASD19, wherein the amorphous solid dispersion comprises one or more antioxidants that are present in an amount of about 0.05% to about 0.5% by weight of the amorphous solid dispersion. Embodiment ASD21 is the amorphous solid dispersion according to any of Embodiments ASD1 to ASD20, wherein the amorphous solid dispersion comprises one or more antioxidants selected from propyl gallate.

Embodiment ASD22 is the amorphous solid dispersion according to any of Embodiments ASD1 to ASD21, wherein the amorphous solid dispersion is prepared by a process comprising electrospraying. Embodiment ASD23 is the amorphous solid dispersion according to any of Embodiments ASD1 to ASD22, wherein the amorphous solid dispersion is an electrosprayed amorphous solid dispersion. Embodiment ASD24 is the amorphous solid dispersion according to any of Embodiments ASD1 to ASD23, wherein the amorphous solid dispersion is prepared by a process comprising spray drying. Embodiment ASD25 is the amorphous solid dispersion according to any of Embodiments ASD1 to ASD24, wherein the amorphous solid dispersion is a spray-dried amorphous solid dispersion.

Embodiment ASD26 is the amorphous solid dispersion according to any of Embodiments ASD1 to ASD25, wherein the amorphous solid dispersion remains amorphous or essentially amorphous as determined by powder X-ray diffraction (XRD) after storage at 40° C./75% relative humidity for 6 months. Embodiment ASD27 is the amorphous solid dispersion according to any of Embodiments ASD1 to ASD26, wherein the amorphous solid dispersion remains amorphous or essentially amorphous as determined by powder X-ray diffraction after storage at 25° C./60% relative humidity for 6 months.

Embodiment ASD28 is the amorphous solid dispersion according to any of Embodiments ASD1 to ASD27, wherein the amorphous solid dispersion comprises a water content as measured by coulometric Karl Fischer titration of less than about 8% after storage at 25° C./60% RH for 6 months. Embodiment ASD29 is the amorphous solid dispersion according to any of Embodiments ASD1 to ASD28, wherein the amorphous solid dispersion comprises a water content as measured by coulometric Karl Fischer titration of less than about 8% after storage at 40° C./75% RH for 6 months.

Embodiment ASD30 is the amorphous solid dispersion according to any of Embodiments ASD1 to ASD29, wherein the amorphous solid dispersion is characterized by an assay level of at least 95% as measured by high performance liquid chromatography (HPLC) after storage at 40° C./75% relative humidity for 6 months. Embodiment ASD31 is the amorphous solid dispersion according to any of Embodiments ASD1 to ASD30, wherein the assay level of the amorphous solid dispersion is at least 97% after storage at 40° C./75% relative humidity for 6 months.

Embodiment ASD32 is the amorphous solid dispersion according to any of Embodiments ASD1 to ASD31, wherein the amorphous solid dispersion comprises a total related substances as measured by HPLC of less than 1.5% after storage at 25° C./60% RH for 12 months. Embodiment ASD33 is the amorphous solid dispersion according to any of Embodiments ASD1 to ASD32, wherein the amorphous solid dispersion comprises a total related substances as measured by HPLC of less than 2% after storage at 40° C./75% RH for 6 months.

Embodiment ASD34 is the amorphous solid dispersion according to any of Embodiments ASD1 to ASD33, wherein the amorphous solid dispersion comprises a glass transition temperature as measured by modulated differential scanning calorimetry that changes by less than 5° C. after storage at 25° C./60% RH for 6 months. Embodiment ASD35 is the amorphous solid dispersion according to any of Embodiments ASD1 to ASD34, wherein the amorphous solid dispersion comprises a glass transition temperature as measured by modulated differential scanning calorimetry that does not change by more than 10° C. after storage at 40° C./75% RH for 6 months. Embodiment ASD36 is the amorphous solid dispersion according to any of Embodiments ASD1 to ASD35, wherein the amorphous solid dispersion comprises a glass transition temperature as measured by modulated differential scanning calorimetry that changes by less than about 6° C. after storage at 40° C./75% RH for up to 6 months.

Embodiment PC1 is a pharmaceutical composition comprising the amorphous solid dispersion according to any of Embodiments ASD1 to ASD36. Embodiment PC2 is a pharmaceutical composition comprising the amorphous solid dispersion according to any of Embodiments ASD1 to ASD36, and one or more pharmaceutically acceptable additives. Embodiment PC3 is the pharmaceutical composition of Embodiment PC2, wherein the one or more pharmaceutically acceptable additives comprises one or more solubilizers, one or more buffering agent, one or more pH-adjusting agents, one or more surfactants, one or more antioxidants, one or more carriers, or a combination thereof. Embodiment PC4 is the pharmaceutical composition of Embodiment PC2, wherein the one or more pharmaceutically acceptable additives comprises one or more filling agents, one or more binding agents, one or more lubricants, one or more disintegrants, one or more glidants, or a combination thereof. Embodiment PC5 is the pharmaceutical composition of Embodiment PC4, wherein the pharmaceutical composition is a solid dosage form suitable for oral administration.

Embodiment PC6 is the pharmaceutical composition of Embodiment PC1 to PC5, wherein the pharmaceutical composition is a gastric acid-insensitive composition.

Embodiment PC7 is the pharmaceutical composition of Embodiment PC1 to PC6, wherein the pharmaceutical composition is an improved variability composition.

Embodiment MT1 is a method of treating a proliferative disorder in a patient in need thereof, the method comprising administering to the patient a pharmaceutical composition according to any of Embodiments PC1 to PC7.

Embodiment MT2 is a method of treating a proliferative disorder in a patient in need thereof, the method comprising administering to the patient a pharmaceutical composition according to any of Embodiments PC1 to PC7, wherein the pharmaceutical composition is administered without regard to whether the patient is co-administered a gastric acid-reducing agent.

Embodiment MT3 is a method of treating a proliferative disorder in a patient in need thereof, the method comprising administering to the patient a pharmaceutical composition according to any of Embodiments PC1 to PC7, wherein the pharmaceutical composition is co-administered to the patient with a gastric acid-reducing agent. Embodiment MT4 is the method according to Embodiment MT3, wherein the gastric acid-reducing agent is administered to the patient shortly before the pharmaceutical composition is administered. Embodiment MT5 is the method according to Embodiment MT3, wherein the gastric acid-reducing agent is administered to the patient concurrently with the administration of the pharmaceutical composition. Embodiment MT6 is the method according to Embodiment MT3, wherein the gastric acid-reducing agent is administered to the patient shortly after the pharmaceutical composition is administered. Embodiment MT7 is the method according to any of Embodiments MT3 to MT6, wherein the gastric acid-reducing agent is selected from an $H_2$ antagonist, a proton pump inhibitor, and an antacid.

Embodiment MT8 is the method according to any of Embodiments MT3 to MT7, wherein a single administration to the patient of the pharmaceutical composition concurrently with or shortly after a gastric-acid reducing agent results in an area-under-the-curve (AUC) of dasatinib that is within 50% of the AUC of dasatinib that results from administration of the pharmaceutical composition without concurrent administration of the gastric acid-reducing agent. Embodiment MT9 is the method according to any of Embodiments MT3 to MT7, wherein single administration to the patient of the pharmaceutical composition concurrently with or shortly after a gastric-acid reducing agent results in a maximum plasma concentration ($C_{max}$) of dasatinib that is within 50% of the $C_{max}$ of dasatinib that results from administration of the pharmaceutical composition without concurrent administration of the gastric acid-reducing agent. Embodiment MT10 is the method according to any of Embodiments MT3 to MT7, wherein single administration to the patient of the pharmaceutical composition concurrently with or shortly after a gastric-acid reducing agent results in an area-under-the-curve (AUC) of dasatinib that is at least 100% greater than the AUC of dasatinib that results from administration of the standard commercial, immediate-release composition of dasatinib concurrently with the gastric-acid reducing agent, wherein the pharmaceutical composition contains the same dasatinib dosage as the standard commercial, immediate-release composition of dasatinib. Embodiment MT11 is the method according to any of Embodiments MT3 to MT7, wherein single administration to the patient of the pharmaceutical composition concurrently with a gastric-acid reducing agent results in a maximum plasma concentration ($C_{max}$) of dasatinib that is at least 200% greater than the $C_{max}$ of dasatinib that results from administration of the standard commercial, immediate-release composition of dasatinib concurrently with the gastric-acid reducing agent, wherein the pharmaceutical composition contains the same dasatinib dosage as the standard commercial, immediate-release composition of dasatinib.

Embodiment MT12 is a method of treating a proliferative disorder in a patient in need thereof, the method comprising administering to the patient a pharmaceutical composition according to any of Embodiments PC1 to PC7, wherein the pharmaceutical composition is administered without regard to whether the patient has elevated gastric pH.

Embodiment MT13 is a method of treating a proliferative disorder in a patient in need thereof, the method comprising administering to the patient a pharmaceutical composition according to any of Embodiments PC1 to PC7; wherein the patient has elevated gastric pH.

Embodiment MT14 is a method of treating a proliferative disorder in a patient in need thereof, the method comprising: (a) identifying a condition by which the patient's gastric pH is chronically elevated; and (b) administering to the patient a therapeutically effective amount of a pharmaceutical composition according to any of Embodiments PC1 to PC7; wherein the therapeutically effective amount comprises about 20 mg to about 140 mg of dasatinib. Embodiment MT15 is the method according to Embodiment MT14, wherein the condition by which the patient's gastric pH is elevated is achlorhydria or hypochlorhydria. Embodiment MT16 is the method according to Embodiment MT14, wherein the condition by which the patient's gastric pH is elevated is infection by *Helicobacter pylori*.

Embodiment MT17 is the method according to any of Embodiments MT13 to MT16, wherein single administration of the pharmaceutical composition when the patient has elevated gastric pH results in an area-under-the-curve (AUC) of dasatinib that is within 50% of the AUC of dasatinib that results from administration of the pharmaceutical composition when the patient does not have elevated gastric pH. Embodiment MT18 is the method according to any of Embodiments MT13 to MT16, wherein single administration of the pharmaceutical composition when the patient has elevated gastric pH results in a maximum plasma concentration ($C_{max}$) of dasatinib that is within 50% of the $C_{max}$ of dasatinib that results from administration of the pharmaceutical composition when the patient does not have elevated gastric pH. Embodiment MT19 is the method according to any of Embodiments MT13 to MT16, wherein single administration of the pharmaceutical composition when the patient has elevated gastric pH results in an area-under-the-curve (AUC) of dasatinib that is at least 100% greater than the AUC of dasatinib that results from administration of the standard commercial, immediate-release composition of dasatinib when the patient has elevated gastric pH. Embodiment MT20 is the method according to any of Embodiments MT13 to MT16, wherein single administration of the pharmaceutical composition when the patient has elevated gastric pH results in a maximum plasma concentration ($C_{max}$) of dasatinib that is at least 200% greater than the $C_{max}$ of dasatinib that results from administration of the standard commercial, immediate-release composition of dasatinib when the patient has elevated gastric pH.

Embodiment MT21 is the method according to any of Embodiments MT1 to MT20, wherein the proliferative disorder is cancer. Embodiment MT22 is the method according to any of Embodiments MT1 to MT20, wherein the proliferative disorder is Philadelphia chromosome-positive chronic myeloid leukemia. Embodiment MT23 is the method according to any of Embodiments MT1 to MT20, wherein the proliferative disorder is Philadelphia chromosome-positive acute lymphoblastic leukemia.

Embodiment MS1 is a method of delivering a therapeutically relevant exposure of dasatinib to a subject without regard to whether the subject is administered a gastric acid-reducing agent, the method comprising administering to the subject a pharmaceutical composition according to any of Embodiments PC1 to PC7.

Embodiment MS2 is a method of delivering a therapeutically relevant exposure of dasatinib to a subject, the method comprising administering to the subject a pharmaceutical composition according to any of Embodiments PC1 to PC7, wherein the pharmaceutical composition is co-administered to the subject with the gastric acid-reducing agent. Embodiment MS3 is the method according to Embodiment MS2, wherein the gastric acid-reducing agent is administered to the subject shortly before the pharmaceutical composition is administered. Embodiment MS4 is the method according to Embodiment MS2, wherein the gastric acid-reducing agent is administered to the subject concurrently with the administration of the pharmaceutical composition. Embodiment MS5 is the method according to Embodiment MS2, wherein the gastric acid-reducing agent is administered to the subject shortly after the pharmaceutical composition is administered. Embodiment MS6 is the method according to any of Embodiments MS2 to MS5, wherein the gastric acid-reducing agent is selected from an $H_2$ antagonist, a proton pump inhibitor, and an antacid.

Embodiment MS7 is the method according to any of Embodiments MS2 to MS6, wherein a single administration to the subject of the pharmaceutical composition concurrently with or shortly after a gastric-acid reducing agent results in an area-under-the-curve (AUC) of dasatinib that is within 50% of the AUC of dasatinib that results from administration of the pharmaceutical composition without concurrent administration of the gastric acid-reducing agent. Embodiment MS8 is the method according to any of Embodiments MS2 to MS6, wherein single administration to the subject of the pharmaceutical composition concurrently with or shortly after a gastric-acid reducing agent results in a maximum plasma concentration ($C_{max}$) of dasatinib that is within 50% of the $C_{max}$ of dasatinib that results from administration of the pharmaceutical composition without concurrent administration of the gastric acid-reducing agent. Embodiment MS9 is the method according to any of Embodiments MS2 to MS6, wherein single administration to the subject of the pharmaceutical composition concurrently with or shortly after a gastric-acid reducing agent results in an area-under-the-curve (AUC) of dasatinib that is at least 100% greater than the AUC of dasatinib that results from administration of the standard commercial, immediate-release composition of dasatinib concurrently with the gastric-acid reducing agent, wherein the pharmaceutical composition contains the same dasatinib dosage as the standard commercial, immediate-release composition of dasatinib. Embodiment MS10 is the method according to any of Embodiments MS2 to MS6, wherein single administration to the subject of the pharmaceutical composition concurrently with a gastric-acid reducing agent results in a maximum plasma concentration ($C_{max}$) of dasatinib that is at least 200% greater than the $C_{max}$ of dasatinib that results from administration of the standard commercial, immediate-release composition of dasatinib concurrently with the gastric-acid reducing agent, wherein the pharmaceutical composition contains the same dasatinib dosage as the standard commercial, immediate-release composition of dasatinib.

Embodiment MS11 is a method of delivering a therapeutically relevant exposure of dasatinib to a subject without regard to whether the subject has elevated gastric pH, the method comprising administering to the subject a pharmaceutical composition according to any of Embodiments PC1 to PC7.

Embodiment MS12 is a method of delivering a therapeutically relevant exposure of dasatinib to a subject who has elevated gastric pH, the method comprising administering to the subject a pharmaceutical composition according to any of Embodiments PC1 to PC7.

Embodiment MS13 is the method according to any of Embodiments MS11 to MS12, wherein single administration of the pharmaceutical composition when the subject has elevated gastric pH results in an area-under-the-curve (AUC) of dasatinib that is within 50% of the AUC of dasatinib that results from administration of the pharmaceutical composition when the subject does not have elevated gastric pH. Embodiment MS14 is the method according to any of Embodiments MT11 to MT12, wherein single administration of the pharmaceutical composition when the subject has elevated gastric pH results in a maximum plasma concentration ($C_{max}$) of dasatinib that is within 50% of the $C_{max}$ of dasatinib that results from administration of the pharmaceutical composition when the subject does not have elevated gastric pH. Embodiment MS15 is the method according to any of Embodiments MT11 to MT12, wherein single administration of the pharmaceutical composition when the subject has elevated gastric pH results in an area-under-the-curve (AUC) of dasatinib that is at least 100% greater than the AUC of dasatinib that results from administration of the standard commercial, immediate-release composition of dasatinib when the subject has elevated gastric pH. Embodiment MS16 is the method according to any of Embodiments MT11 to MT12, wherein single administration of the pharmaceutical composition when the subject has elevated gastric pH results in a maximum plasma concentration ($C_{max}$) of dasatinib that is at least 200% greater than the $C_{max}$ of dasatinib that results from administration of the standard commercial, immediate-release composition of dasatinib when the subject has elevated gastric pH.

Embodiment TR1 is a treatment regimen for treating a proliferative disorder in a patient in need thereof, the regimen comprising: (a) administering to the patient a first dose, the first dose comprising a standard dosage of a proton pump inhibitor or $H_2$ antagonist; and (b) within 20 hours after the first dose, administering a second dose to the patient, the second dose comprising a therapeutically effective amount of a pharmaceutical composition according to any of Embodiments PC1 to PC7, wherein the therapeutically effective amount comprises about 20 mg to about 140 mg dasatinib. Embodiment TR2 is the treatment regimen according to Embodiment TR1, wherein the second dose is administered within 16 hours after the first dose. Embodiment TR3 is the treatment regimen according to Embodiment TR1, wherein the second dose is administered within 12 hours after the first dose. Embodiment TR4 is the treatment regimen according to Embodiment TR1, wherein the second dose is administered within 8 hours after the first dose. Embodiment TR5 is the treatment regimen according to Embodiment TR1, wherein the second dose is administered within 6 hours after the first dose. Embodiment TR6 is the treatment regimen according to Embodiment TR1, wherein the second dose is administered within 4 hours after the first dose. Embodiment TR7 is the treatment regimen according to Embodiment TR1, wherein the second dose is administered within 2 hours after the first dose.

Embodiment TR8 is the treatment regimen according to any of Embodiments TR1 to TR7, wherein the first dose comprises a standard dosage of a proton pump inhibitor selected from rabeprazole, esomeprazole, lansoprazole, omeprazole, pantoprazole, dexlansoprazole, or a combination thereof. Embodiment TR9 is the treatment regimen according to any of Embodiments TR1 to TR7, wherein the first dose comprises a standard dosage of omeprazole. Embodiment TR10 is the treatment regimen according to any of Embodiments TR1 to TR7, wherein the first dose comprises a standard dosage of an $H_2$ antagonist selected from famotidine, cimetidine, nizatidine, ranitidine, or a combination thereof. Embodiment TR11 is the treatment regimen according to any of Embodiments TR1 to TR7, wherein the first dose comprises a standard dosage of famotidine.

Embodiment TR12 is a treatment regimen for treating a proliferative disorder in a patient in need thereof, the regimen comprising: (a) administering to the patient a first dose, the first dose comprising a standard dosage of an antacid; and (b) within 2 hours before or 2 hours after the first dose, administering a second dose to the patient, the second dose comprising a pharmaceutical composition according to any of Embodiments PC1 to PC7; wherein the administration of the second dose provides a therapeutically relevant exposure of dasatinib to the patient.

Embodiment TR13 is the treatment regimen according to any of Embodiments TR1 to TR12, wherein the proliferative disorder is cancer. Embodiment TR14 is the treatment regimen according to any of Embodiments TR1 to TR12, wherein the proliferative disorder is Philadelphia chromosome-positive chronic myeloid leukemia. Embodiment TR15 is the treatment regimen according to any of Embodiments TR1 to TR12, wherein the proliferative disorder is Philadelphia chromosome-positive acute lymphoblastic leukemia.

Embodiment KT1 is a kit for sale to a user, the kit comprising a pharmaceutical composition according to any of Embodiments PC1 to PC7 and a package insert, wherein the package insert informs the user that the pharmaceutical composition can be co-administered with a gastric acid-reducing agent.

Embodiment KT2 is a kit for sale to a user, the kit comprising a pharmaceutical composition according to any of Embodiments PC1 to PC7 and a package insert, wherein the package insert does not comprise a warning that the pharmaceutical composition should not be co-administered with $H_2$ antagonists or proton pump inhibitors.

Embodiment KT3 is a kit for sale to a user, the kit comprising a pharmaceutical composition according to any of Embodiments PC1 to PC7 and a package insert, wherein the package insert informs the user that the pharmaceutical composition can be suitably administered if the user has chronically elevated gastric pH.

Embodiment KT4 is a kit for sale to a user, the kit comprising a pharmaceutical composition according to any of Embodiments PC1 to PC7 and a package insert, wherein package insert informs the user that the pharmaceutical composition can be suitably administered if the user has been diagnosed with or is afflicted by achlorhydria or hypochlorhydria.

Embodiment KT5 is a kit for sale to a user, the kit comprising a pharmaceutical composition according to any of Embodiments PC1 to PC7 and a package insert, wherein the package insert informs the user that the pharmaceutical composition can be suitably administered if the user has been diagnosed with or is afflicted by *Helicobacter pylori* infection.

EXAMPLES

Objects and advantages of this disclosure are further illustrated by the following examples, but the particular materials and amounts thereof recited in these examples, as well as other conditions and details, should not be construed to unduly limit this disclosure.

Example 1. Amorphicity and Stability of Dasatinib ASDs

A study was performed to investigate the impact of drug load on the chemical and physical stability of six different ASDs comprising dasatinib and either EUDRAGIT L100-55 or EUDRAGIT E100 as the polymer. The drug:polymer ratio in the ASDs were 50:50, 60:40, or 70:30 (w/w).

To prepare the ASDs, appropriate quantities of dasatinib monohydrate and polymer were dissolved in a 50:50 (v/v) solvent mixture of ethanol and methanol to provide a liquid feedstock having a drug concentration of 4 mg/mL. The ASDs were formed by electrospraying the liquid feedstock using the Nanocopoeia spray machine ENS-P. The ENS-P machine utilized six nozzle slots, which were arranged in a circular array. Each nozzle had twenty-four tips (D24). For each spray run, the spray process parameters, such as extractor voltage and flow rate, were adjusted to achieve an acceptable spray plume.

Each of the resulting ASDs was placed on stability under accelerated conditions at 40° C./75% RH. The ASDs were assessed at t=0, 2 weeks, 1 month, 2 months, and 3 months for appearance, amorphicity, loss on drying, glass transition temperature, assay/impurities, and particle morphology.

Appearance

Each ASD was assessed for physical appearance post-spray (t=0) and at each time point on stability. All six ASDs were white to off-white powders at t=0 and showed no visible change on stability.

Amorphicity

Amorphicity (i.e., the lack of crystallinity) for the ASDs was assessed by XRD. Diffraction patterns were obtained using a Rigaku MiniFlex 600. The X-ray source was a long anode Cu Kα. Samples were prepared by placing a small amount of ASD powder on a Rigaku zero-background sample holder with a 0.1 mm indent. A glass slide was then used to firmly pack the powder and ensure the surface of the sample was level with the edge of the sample holder.

Rigaku Data Analysis Software PDXL 2.4.2.0 was used to determine percent crystallinity. Briefly, a linear background was obtained by connecting the beginning and end of each diffractogram. Peaks were then fitted to split pseudo-Voigt shape by the Lorentzian function. Generally, narrow peaks with full width at half maximum (FWHM) less than 1° were assigned as crystalline phase. Amorphous halos had FWHM greater than 1°, typically greater than 5°. The percent of crystallinity was calculated as follows:

% crystallinity=area of crystalline peaks/(area of crystalline peaks+amorphous peaks)

The analysis found that all ASDs remained completely amorphous for three months at 40° C./75% RH, regardless of the drug load or the polymer.

Loss on Drying

Loss on drying (LOD) was assessed using thermogravimetric analysis (TGA), using a TA Instruments Model Q500. In general, about 5-10 mg of ASD material was loaded in a platinum sample pan.

Each of the ASDs was assessed for LOD post-spray (t=0) and at each time point on stability. Because TGA simply measures sample weight loss as a function of temperature, the technique provides a measure of the total residual solvent present but is not capable of distinguishing between organic solvents and water. LOD results for the six ASDs are listed in Table 4.

TABLE 4

LOD (TGA) data summary for the compositions of Example 1.

| | LOD (% weight loss) | | | | | |
|---|---|---|---|---|---|---|
| Time | Dasatinib:EUDRAGIT L100-55 | | | Dasatinib:EUDRAGIT E100 | | |
| Point | 50:50 | 60:40 | 70:30 | 50:50 | 60:40 | 70:30 |
| 0 | 5.4 | 5.7 | 5.5 | 2.2 | 2.7 | 3.1 |
| 2 weeks | 7.0 | 7.3 | 7.3 | 3.2 | 3.5 | 3.9 |
| 1 month | 6.6 | 7.1 | 7.3 | 3.2 | 3.5 | 4.2 |
| 2 months | 6.0 | 6.1 | 6.1 | 2.6 | 2.5 | 3.1 |
| 3 months | 5.5 | 5.7 | 5.9 | 2.0 | 2.3 | 2.3 |

As demonstrated in Table 4, the EUDRAGIT L100-55 ASDs had higher levels of residual solvent and/or moisture compared to EUDRAGIT E100 ASDs for all drug:polymer ratios. Despite some variability in the data, all ASDs demonstrated consistent loss on drying throughout the stability study.

Glass Transition Temperature

Glass transition temperature ($T_g$) of the ASDs was analyzed using modulated differential scanning calorimetry (mDSC), which was run on a TA Instruments Model Q200 equipped with a RCS90 refrigerated cooling system. In general, about 5-10 mg of ASD powder was loaded in a TA $T_{zero}$ low-mass aluminum pan and sealed with a $T_{zero}$ lid. Instrument details and measurement conditions are provided in Table 5. The results of the mDSC analysis are provided in Table 6.

TABLE 5

TA Q200 DSC instrument and measurement conditions.

| Parameter | Conditions |
|---|---|
| DSC Mode | Modulated |
| Test | MDSC heat only |
| Method | Modulate + 0.447° C. every 60 sec, Temperature ramp 3.00° C./min from 0.00° C. to 200.00° C. |
| Data Sampling Interval | 0.20 sec |

TABLE 6

Glass transition temperature data for the ASDs of Example 1.

| | Tg (° C.) | | | | | |
|---|---|---|---|---|---|---|
| Time | Dasatinib:EUDRAGIT L100-55 | | | Dasatinib: EUDRAGIT E100 | | |
| Point | 50:50 | 60:40 | 70:30 | 50:50 | 60:40 | 70:30 |
| 0 | 148.3 | 148.3 | 142.5 | 67.0 | 78.25 | Not detected |
| 2 weeks | 147.2 | 147.5 | 144.2 | 61.5 | Not detected | Not detected |
| 1 month | 148.8 | 147.7 | 143.3 | Not detected | Not detected | Not detected |
| 2 months | >140 | 147.1 | 143.6 | Not detected | Not detected | Not detected |
| 3 months | 146.6 | 146.3 | 143.1 | 64.6 | Not detected | Not detected |

For all three EUDRAGIT L100-55 ASDs, there was essentially no change in $T_g$ on stability. In the case of EUDRAGIT E100 ASDs, thermal events consistent with a glass transition temperature were identified in only a few samples. Despite the lack of a measurable $T_g$ for many of the samples, the EUDRAGIT E100 ASDs remained amorphous and showed no signs of change based on visual appearance over the entire three months on stability.

Assay/Impurities

Assay/impurities of the ASDs were assessed using both an Agilent 1200 HPLC and a Waters Alliance e2695 HPLC. The instrument and measurement conditions are specified in Table 7, while the gradient profile is listed in Table 8.

TABLE 7

HPLC instrument and measurement conditions used for the assay/impurity analysis of Example 1.

| Parameter | Condition |
|---|---|
| Mobile Phase A | 0.1% Formic acid in water |
| Mobile Phase B | 0.1% Formic acid in acetonitrile |
| Flow | 0.7 mL/min, gradient |
| Injection Volume | 10 µL |
| Column Temperature | 55° C. |
| Wavelength | 324 nm |
| Run Time | 40 min |

TABLE 8

HPLC instrument gradient profile used for the assay/impurity analysis of Example 1.

| Time (min) | % Mobile Phase A | % Mobile Phase B |
|---|---|---|
| 1.00 | 85.0 | 15.0 |
| 15.00 | 50.0 | 50.0 |

TABLE 8-continued

HPLC instrument gradient profile used for the assay/impurity analysis of Example 1.

| Time (min) | % Mobile Phase A | % Mobile Phase B |
|---|---|---|
| 25.00 | 40.0 | 60.0 |
| 32.00 | 10.0 | 90.0 |
| 35.00 | 10.0 | 90.0 |
| 35.10 | 85.0 | 15.0 |
| 40.00 | 85.0 | 15.0 |

Assay values are listed in Table 9 and total impurities are listed in Table 10 for each ASD at t=0 and at the 3-month stability time point.

TABLE 9

Assay (HPLC) data summary for the compositions in Example 1.

| | Assay (% Label Claim) | | | | | |
|---|---|---|---|---|---|---|
| | Dasatinib:EUDRAGIT L100-55 | | | Dasatinib:EUDRAGIT E100 | | |
| Time Point | 50:50 | 60:40 | 70:30 | 50:50 | 60:40 | 70:30 |
| 0 | 102.5 | 96.3 | 102.0 | 87.6 | 92.7 | 92.9 |
| 3 months | 100.9 | 93.8 | 98.4 | 86.7 | 87.1 | 91.6 |

TABLE 10

Total impurities (HPLC) data summary for the compositions in Example 1.

| | Total Impurities (%) | | | | | |
|---|---|---|---|---|---|---|
| | Dasatinib:EUDRAGIT L100-55 | | | Dasatinib:EUDRAGIT E100 | | |
| Time Point | 50:50 | 60:40 | 70:30 | 50:50 | 60:40 | 70:30 |
| 0 | 0.362 | 0.389 | 0.358 | 0.861 | 0.943 | 1.051 |
| 3 months | 0.446 | 0.576 | 0.601 | 0.841 | 0.810 | 0.769 |

Table 10 shows that the EUDRAGIT L100-55 ASDs had slightly lower total impurity levels than the EUDRAGIT E100 ASDs at the 3-month time point. Total impurities levels did increase slightly with increasing drug load for the EUDRAGIT L100-55 ASDs; however, the differences were small. Conversely, there was no apparent impact of drug load on total impurities for the EUDRAGIT E100 ASDs.

Particle Morphology

Particle morphology of each ASD was analyzed using scanning electron microscopy (SEM) at t=0 and at all stability time points using a JEOL JSM-6010Plus/LV. A small amount of each ENS powder was coated with a thin layer of platinum using a JEOL Sputter Coater prior to analysis.

Based on SEM images, the EUDRAGIT L100-55 ASD particles ranged in size from approximately 200 nm-2 µm while the EUDRAGIT E100 ASD particles ranged in size from 500 nm-4 µm.

All ASDs appeared to maintain their morphology after open dish exposure for several months under accelerated conditions. There were not any clear changes to the ASD particles and no signs of particle fusion were evident, suggesting that the ASDs remained physically stable. This data was in good agreement with the physical appearance and XRD assessments, which indicated neither observable change in the powders nor any conversion from the amorphous to the crystalline state on stability.

In a separate experiment, an ASD was prepared comprising dasatinib and polyvinylpyrrolidone (PVP K25) as the polymer, using a similar technique as above, at a 50:50 drug:polymer ratio. This ASD was maintained under harsh 50° C./80% RH (open dish) conditions. After 2 weeks, the ASD exhibited some crystalline character; after 4 weeks, a significant portion of the material had converted to crystalline.

Example 2. Long-Term Stability of Dasatinib ASDs Under Accelerated Conditions

A study was performed to assess long-term physical and chemical stability of ASDs containing dasatinib and EUDRAGIT L100-55 as the stabilizing polymer in w/w ratio of 60:40 (drug:polymer). To prepare the ASDs, suitable quantities of dasatinib (anhydrous) and polymer were dissolved in a 40:10:50 (v/v/v) solvent mixture of methanol:ethanol:ethyl acetate to prepare a liquid feedstock at a drug concentration of 12.83 mg/mL, which was electrosprayed similar to Example 1.

The resulting ASDs were evaluated under storage conditions of 25° C./60% RH, 25° C./protected, 40° C./75% RH, and 40° C./protected, at time points of 1 month, 3 months, and 6 months. ASDs stored at 25° C./60% RH and 25° C./protected were additionally evaluated at 9 months and 12 months.

Aliquots of approximately 300 mg of ASD powder were manually filled into 7 mL vials for each time point and condition. Vials exposed to the humidity conditions were loosely capped (open dish) and maintained in an upright position inside the chamber. Protected conditions were achieved by sealing closed vials in aluminum pouches, which were also maintained in an upright position.

Amorphicity, glass transition temperature, water content, LOD, and assay/impurities were evaluated for each sample. Amorphicity and glass transition temperature were assessed using the methodology described in Example 1.

Water content was determined using a coulometric Karl Fischer Titration. Approximately 40-50 mg of ASD powder was weighed into a glass Stromboli sample vial and the vial was immediately sealed with a foil coated vial cover, and a rubber vial cap cover was placed on top of the sample vial. LOD was evaluated using the Computrac Max 4000, in which approximately 0.5 g of material was spread evenly across the sample pan. Assay/impurities of the ASDs were assessed using the instrument parameters, measurement conditions, and gradient profile specified in Table 11.

TABLE 11

HPLC instrument and measurement conditions.

| Parameter | Condition | | |
|---|---|---|---|
| Column | Waters XBridge C18, 3.0 × 150 mm, 3.5 µm particle size | | |
| Flow rate | 0.7 mL/min | | |
| Mobile Phase A | 20 mM Ammonium Bicarbonate pH 9.0 | | |
| Mobile Phase B | 100% Acetonitrile (ACN) | | |
| Impurities Program | Time (min) | % A | % B |
| | 0.00 | 95 | 5 |
| | 6.00 | 80 | 20 |

TABLE 11-continued

HPLC instrument and measurement conditions.

| Parameter | Condition | | |
|---|---|---|---|
| | 28.00 | 60 | 40 |
| | 35.00 | 0 | 100 |
| | 35.01 | 95 | 5 |
| | 40.00 | 95 | 5 |
| Injection Volume | 10.0 µL | | |
| Column Temperature | 45° C. | | |

TABLE 11-continued

HPLC instrument and measurement conditions.

| Parameter | Condition |
|---|---|
| Detector Wavelength | 324 nm |
| Scan Range | 190-400 nm |

The results of this study are presented in Tables 12-15. LOD, which was only measured at t=0, was determined to be 2.14%.

Under each of the storage conditions, the ASDs demonstrated chemical and physical stability for the entire length of the study.

TABLE 12

Evaluation of Dasatinib:EUDRAGIT L100-55 (60:40) ASD under 25° C./60% RH storage conditions.

| Test | Initial | 1 Month | 3 Month | 6 Month |
|---|---|---|---|---|
| Appearance | Off-white powder | Off-white powder | Off-white powder | Off-white powder |
| XRD Crystallinity | Amorphous | Amorphous | Amorphous | Amorphous |
| $T_g$ (° C.) | 146.36 | 146.57 | 147.06 | 144.19 |
| Water Content (%) | 1.64 | 5.94 | 6.36 | 6.15 |
| Assay (%) | 100.1 | 96.2 | 93.4 | 93.0 |
| Total Impurities (%) | 0.26 | 0.36 | 0.24 | 0.26 |

TABLE 13

Evaluation of Dasatinib:EUDRAGIT L100-55 (60:40) ASD under 25° C./protected storage conditions.

| Test | Initial | 1 Month | 3 Month | 6 Month |
|---|---|---|---|---|
| Appearance | Off-white powder | Off-white powder | Off-white powder | Off-white powder |
| XRD Crystallinity | Amorphous | Amorphous | Amorphous | Amorphous |
| $T_g$ (° C.) | 146.36 | 146.87 | 146.51 | 146.38 |
| Water Content (%) | 1.64 | 2.27 | 3.52 | 2.58 |
| Assay (%) | 100.1 | 101.3 | 96.4 | 97.3 |
| Total Impurities (%) | 0.26 | 0.30 | 0.24 | 0.25 |

TABLE 14

Evaluation of Dasatinib:EUDRAGIT L100-55 (60:40) ASD under 40° C./75% RH storage conditions.

| Test | Initial | 1 Month | 3 Month | 6 Month |
|---|---|---|---|---|
| Appearance | Off-white powder | Off-white powder | Off-white powder | Off-white powder |
| XRD Crystallinity | Amorphous | Amorphous | Amorphous | Amorphous |
| $T_g$ (° C.) | 146.36 | 145.69 | 147.24 | 148.09 |
| Water Content (%) | 1.64 | 8.03 | 7.65 | 7.21 |
| Assay (%) | 100.1 | 93.6 | 91.9 | 94.0 |
| Total Impurities (%) | 0.26 | 0.21 | 0.21 | 0.28 |

TABLE 15

Evaluation of Dasatinib:EUDRAGIT L100-55 (60:40) ASD under 40° C./protected storage conditions.

| Test | Initial | 1 Month | 3 Month | 6 Month |
|---|---|---|---|---|
| Appearance | Off-white powder | Off-white powder | Off-white powder | Off-white powder |
| XRD Crystallinity | Amorphous | Amorphous | Amorphous | Amorphous |
| $T_g$ (° C.) | 146.36 | 146.23 | 146.03 | 146.59 |
| Water Content (%) | 1.64 | 3.00 | 4.06 | 3.50 |
| Assay (%) | 100.1 | 101.8 | 95.8 | 96.2 |
| Total Impurities (%) | 0.26 | 0.32 | 0.25 | 0.28 |

Example 3. In Vitro Dissolution of Dasatinib ASDs

A study was performed to investigate the in vitro dissolution performance of ASDs comprising dasatinib with EUDRAGIT L100-55 at a ratio of 60:40 (w/w), and comprising dasatinib with EUDRAGIT E100 at a ratio of 50:50 (w/w). SPRYCEL, the reference listed drug, was also included in the study as a benchmark, in the form of powder prepared by manually crushing a suitable number of tablets.

To prepare the EUDRAGIT L100-55 ASD, a liquid feedstock was prepared by dissolving appropriate quantities of dasatinib (anhydrous) and polymer in a 65:20:15 (v/v/v) solvent mixture of methanol:ethanol:MEK to provide a drug concentration of 15 mg/mL. To prepare the EUDRAGIT E100 ASD, a liquid feedstock was prepared by dissolving appropriate quantities of dasatinib (anhydrous) and polymer in a 65:35 (v/v) solvent mixture of methanol:MEK to provide a drug concentration of 7.5 mg/mL. ASDs were then formed by electrospraying the respective liquid feedstocks using the Nanocopoeia spray machine ENS-P. The ENS-P machine utilized six nozzle slots, which were arranged in a circular array. Each nozzle had twenty-four tips (D24). For each spray run, the spray process parameters, such as extractor voltage and flow rate, were adjusted to achieve an acceptable spray plume.

For the in vitro study, a two-stage dissolution method was developed to mimic conditions in the stomach and upper intestine, and to mimic a transition between the two regions of the gastrointestinal tract. The first-stage dissolution was conducted in Fasted State Simulated Gastric Fluid (FaSSGF) using three media that differed only in pH: Medium A (pH 1.6), Medium B (pH 4.0), and Medium C (pH 6.0). Three Transition Media (D, E, and F) were developed to convert the three FaSSGF media to the second stage dissolution medium, Fasted State Simulated Intestinal Fluid (FaSSIF).

For the two-stage dissolution, a Vankel model VK7000 dissolution bath was fitted with a USP Apparatus II system equipped with mini-vessels and mini-paddles. A Rainbow Dynamic Dissolution Monitor System (Delphian Technology Inc., Woburn, Mass.) was used to monitor the solution concentration of dasatinib in situ. The Rainbow system contains a Cathodeon Type J75 Deuterium (D2) lamp that transmits its signal via furcation cable to supply the primary signals to six stainless steel probes (20 mm path). A probe was positioned in each dissolution vessel. Samples were quantified against a 7-point standard curve that was developed for each ASD at each dissolution stage.

The compositions of the three FaSSGF Media (A, B, and C) used for the first-stage dissolution are listed in Table 16.

TABLE 16

Compositions of first-stage dissolution FaSSGF Media A, B, and C.

| Component | FaSSGF A (pH 1.6) | FaSSGF B (pH 4.0) | FaSSGF C (pH 6.0) |
| --- | --- | --- | --- |
| FaSSGF Instant Powder | 60.0 mg | 60.0 mg | 60.0 mg |
| NaCl | 2.00 g | 2.00 g | 2.00 g |
| HCl/NaOH Solution | q.s. to pH 1.6 | q.s. to pH 4.0 | q.s. to pH 6.0 |
| Deionized H$_2$O | q.s. to 1 L | q.s. to 1 L | q.s. to 1 L |

For the dissolution procedure, 75 mL of one FaSSGF Medium (A, B, or C) was filled into a dissolution vessel, and then a sample (ASD or SPRYCEL powder) was accurately weighed to provide 42 mg dasatinib (sample weight varied with sample composition drug load) for each vessel. Dasatinib concentrations were measured at 10, 20, and 30 minutes after introduction of the sample to the vessel.

The compositions of the three Transition Media (D, E, and F) used to convert the three FaSSGF media to the second stage dissolution medium (FaSSIF) are listed in Table 17.

TABLE 17

Composition of Transition Media D, E, and F.

| Component | Transition Medium D | Transition Medium E | Transition Medium F |
| --- | --- | --- | --- |
| FaSSGF-V2 Instant Powder | 6.98 g | 6.98 g | 6.98 g |
| NaCl | 10.0 g | 10.0 g | 10.0 g |
| Maleic Acid | 8.88 g | 8.88 g | 8.88 g |
| NaOH | 9.45 g | 5.77 g | 5.80 g |
| Deionized H$_2$O | q.s. to 1 L | q.s. to 1 L | q.s. to 1 L |

The second-stage dissolution medium, FaSSIF, was prepared by adding 25 mL of the appropriate Transition Medium to 75 mL of the corresponding first-stage FaSSGF Medium, as summarized in Table 18. The resulting composition of FaSSIF was the same for all three combinations (A+D, B+E, and C+F) and the pH of the FaSSIF media in each case was 6.4.

TABLE 18

Composition of second-stage dissolution medium (FaSSIF).

| Component | Quantity |
| --- | --- |
| FaSSGF-V2 Instant Powder | 174.5 mg |
| FaSSGF Instant Powder | 4.50 mg |
| NaCl | 400 mg |
| Maleic Acid | 222 mg |
| NaOH | 236.25 mg |
| HCl/NaOH Solution | q.s. pH 6.4 |
| Deionized H$_2$O | q.s. to 100 mL |

For the second-stage dissolution procedure, 25 mL of the appropriate Transition Medium (D, E, or F) was added to the respective vessel 30 minutes after the addition of the ASD sample. Dasatinib concentrations were measured at 45, 60, and 90 minutes (elapsed time from introduction of the sample to the vessel). The data reported in the figures as described below is expressed as a percentage of dasatinib measured in solution relative to the total dasatinib introduced into the vessel.

Transition of FaSSGF (pH 1.6) to FaSSIF (pH 6.4)

The dissolved drug-time profiles for dasatinib in FaSSGF (pH 1.6) transitioned to FaSSIF (pH 6.4) are presented in FIG. 1. Each of the ASDs and SPRYCEL released nearly all of the dasatinib into solution in the first 10 minutes and maintained relatively steady concentrations until the transition to FaSSIF at t=30 min. For SPRYCEL, this result was expected based upon the known moderate solubility of dasatinib in acidic environments. That the ASDs also released nearly all of the dasatinib in the first 10 minutes at pH 1.6 was unexpected, in light of the poor solubility of EUDRAGIT L100-55 in acidic environments.

However, following the transition from FaSSGF to FaSSIF at t=30 min, the result was different for SPRYCEL compared to the ASDs. In the case of SPRYCEL, only approximately 10% of the dasatinib remained in solution after 90 minutes, presumably as a result of the known poor solubility of dasatinib at neutral pH. In contrast, the ASDs were able to maintain much higher dasatinib concentrations in solution, ranging from 70%-80% for EUDRAGIT L100-55 ASD and 90%-100% for EUDRAGIT E100 ASD.

Transition of FaSSGF (pH 4.0) to FaSSIF (pH 6.4)

Figure 2:
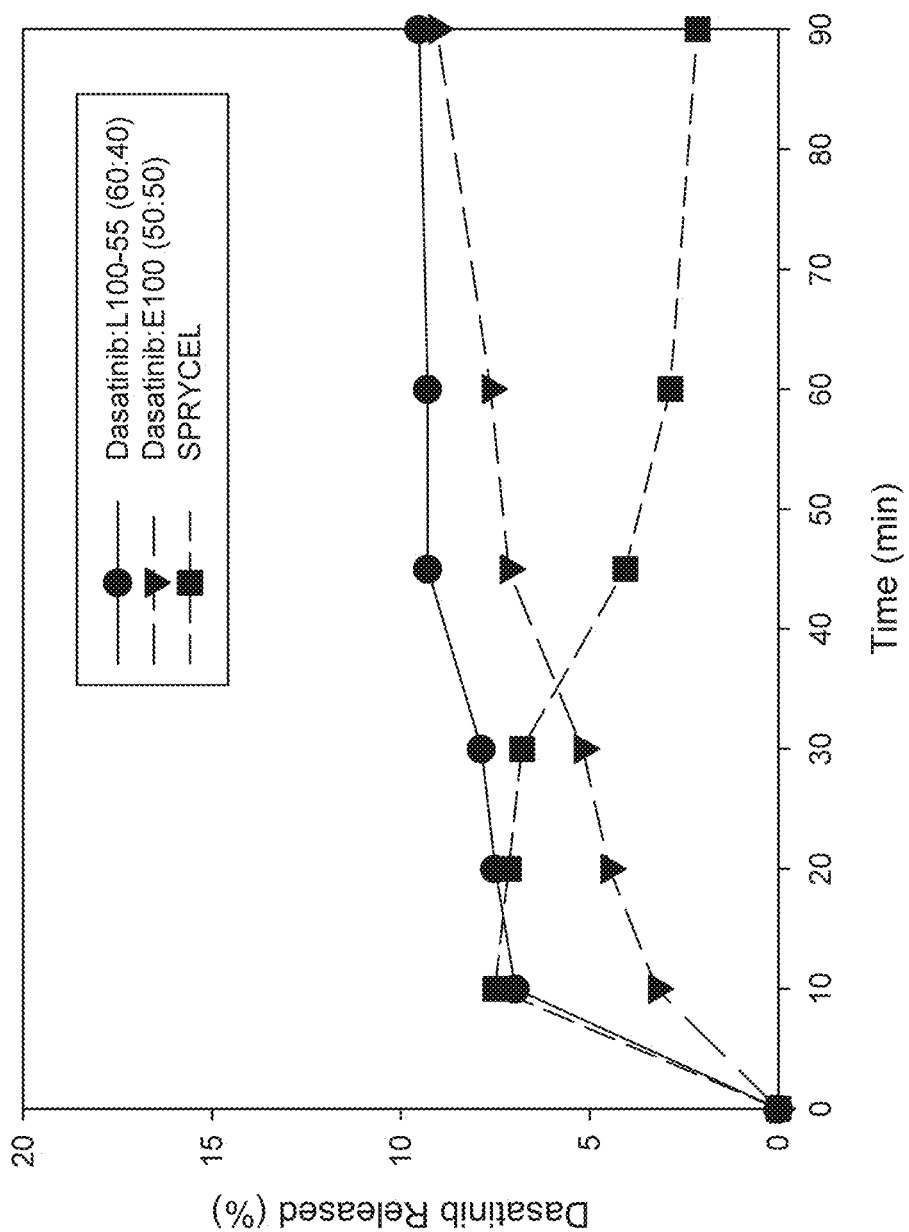
FIG. 2 shows in vitro dissolution profiles of dasatinib dissolved in FaSSGF (pH 4.0) transitioned to FaSSIF (pH 6.4) at t=30 min, for an ASD of dasatinib and EUDRAGIT L100-55 at a w/w ratio (Dasatinib:EUDRAGIT L100-55) of 60:40, for an ASD of dasatinib and EUDRAGIT E100 at a w/w ratio (Dasatinib:EUDRAGIT E100) of 50:50, and for SPRYCEL, as described in Example 3. Each data point represents the mean of three replicates.

The dissolved drug-time profiles for dasatinib in FaSSGF (pH 4.0) to FaSSIF (pH 6.4) are presented in FIG. 2. Each of the ASDs and SPRYCEL released dasatinib into solution to a much lower extent in FaSSGF with the pH adjusted to 4.0 as compared to the same medium at pH 1.6 (FIG. 1). SPRYCEL and EUDRAGIT L100-55 ASD achieved very similar concentrations after 10 minutes (approximately 7%), which was maintained until the transition to FaSSIF at t=30 min. The EUDRAGIT E100 ASD released dasatinib to a lesser extent and achieved a slightly lower dasatinib concentration by 30 minutes (approximately 5%).

Upon addition of the transition media at t=30 min, the solution concentration of dasatinib quickly dropped for SPRYCEL, ultimately reducing to approximately 2% after 90 minutes. In contrast, the solution concentration of dasatinib increased for the ASDs following transition to FaSSIF. Although the increases were modest, the ASDs were able to maintain solution concentrations of 9%-10% after 90 minutes.

Transition of FaSSGF (pH 6.0) to FaSSIF (pH 6.4)

Figure 3:
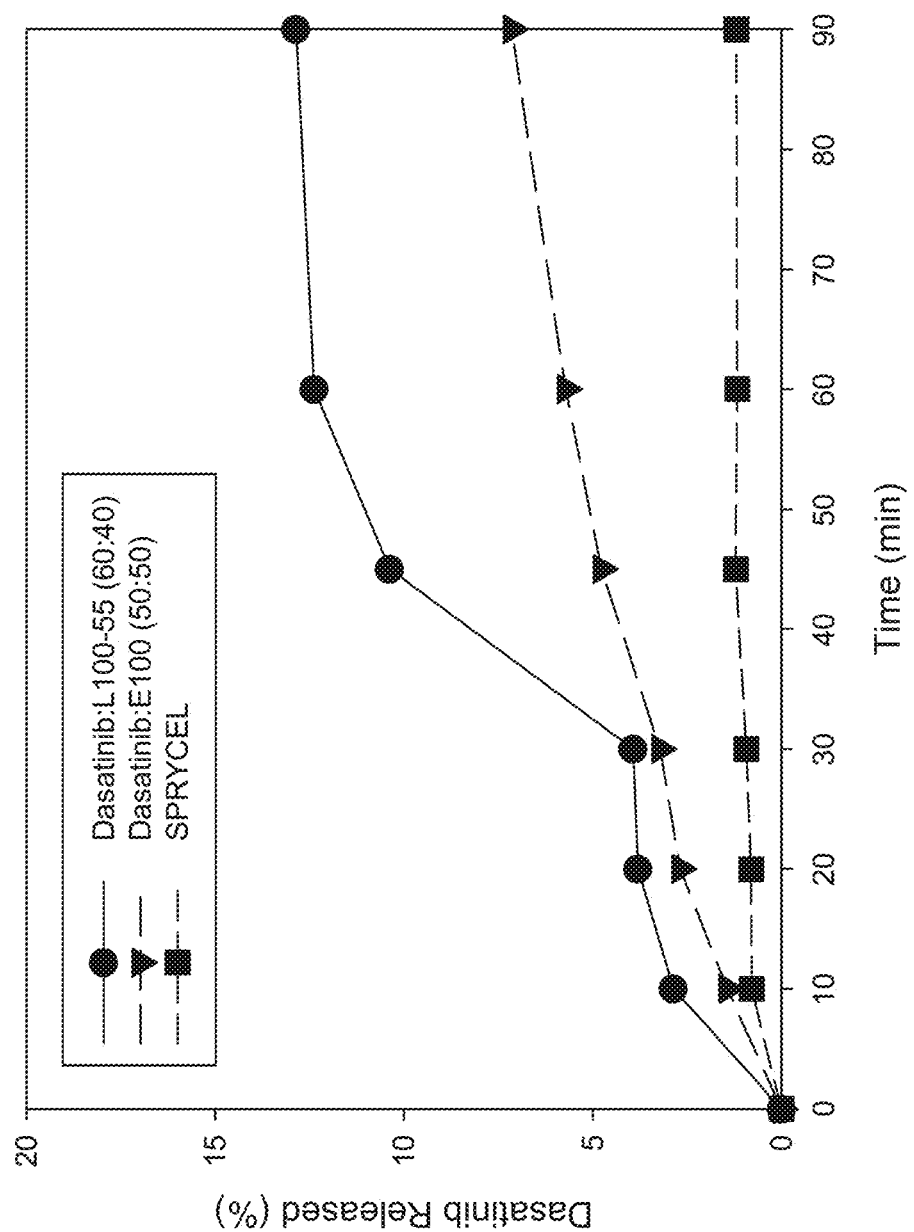
FIG. 3 shows in vitro dissolution profiles of dasatinib dissolved in FaSSGF (pH 6.0) transitioned to FaSSIF (pH 6.4) at t=30 min, for an ASD of dasatinib and EUDRAGIT L100-55 at a w/w ratio (Dasatinib:EUDRAGIT L100-55) of 60:40, for an ASD of dasatinib and EUDRAGIT E100 at a w/w ratio (Dasatinib:EUDRAGIT E100) of 50:50, and for SPRYCEL, as described in Example 3. Each data point represents the mean of three replicates.

The dissolved drug-time profiles for dasatinib in FaSSGF (pH 6.0) to FaSSIF (pH 6.4) are presented in FIG. 3. Release of dasatinib into solution in FaSSGF at pH 6.0 was even lower than that observed in the pH 4.0 medium. As shown in FIG. 3, SPRYCEL released almost no dasatinib into solution in either the first or second stage of dissolution. This result was not unexpected based on the similar pH conditions for FaSSGF and FaSSIF in this experiment and the known low dasatinib solubility at near-neutral pH conditions.

Each of the ASDs and SPRYCEL achieved concentrations of approximately 3%-4% in neutral FaSSGF. However, significantly higher dasatinib solution concentrations were achieved for the ASDs upon transition to FaSSIF when compared to SPRYCEL. The dasatinib solution concentration slowly increased for the EUDRAGIT E100 ASD, ultimately achieving approximately 7% after 90 minutes, while the EUDRAGIT L100-55 ASD achieved approximately 13% in solution after 90 minutes.

Taken together, these results demonstrate that, at low pH, each of the ASDs and SPRYCEL were shown to have good dissolution in FaSSGF, achieving dasatinib concentration above 80%. However, following the transition to FaSSIF, the two ASDs significantly outperformed SPRYCEL. At the intermediate and high pH FaSSGF conditions, each of the ASDs and SPRYCEL performed similarly initially; however, the ASDs outperformed SPRYCEL upon transition to the neutral pH FaSSIF.

Example 4. Canine In Vivo Studies

An in vivo study was performed on canine subjects to investigate the impact of stomach pH on the pharmacokinetics observed upon administration of dasatinib ASDs. The study included an ASDs comprising dasatinib with EUDRAGIT L100-55 at a ratio of 60:40 (w/w), an ASD comprising dasatinib with EUDRAGIT E100 at a ratio of 50:50 (w/w), and SPRYCEL (prepared as described below). ASDs were generated using electrospray techniques similar to prior Examples.

The pharmacokinetics of the three test compositions (two ASDs and SPRYCEL) was evaluated in male beagle dogs. The study incorporated pentagastrin and famotidine pretreatments to adjust the stomach pH of the dogs prior to dosing. Based on published protocols, the pentagastrin pretreatment was expected to control the pH to a range between 1 and 2, while the famotidine pretreatment was expected to control the pH to a range between 6 and 8. Thus, in all, there were six legs to the study—each of the three compositions administered with each of the two pretreatments.

A summary of the study design is provided in Table 19. The study employed a cross-over study design, with the same dogs receiving each dose following a one-week wash-out period between each leg of the study.

Dogs were fasted for a minimum of twelve hours prior to dose administration. Dogs were supplied with water ad libitum, and were housed one per cage. Each study leg had five dogs. In study legs 1, 2, and 5, dogs were pretreated with famotidine (40 mg oral tablet) administered three hours prior to dosing of the test composition. In study legs, 3, 4, and 6 dogs were pretreated with pentagastrin (6 µg/kg dose, intramuscular injection) 30 minutes prior to dosing of the test composition. Each dog then received an appropriate oral dose of one of the test compositions at time zero. Following dosing, blood samples were collected at 5, 15, 30, 45 minutes, 1, 2, 4, 6, 10, 16, 24, 36 hours.

TABLE 19

Study design for Example 4.

| Study Leg | Composition | Pre-treatment | Dose (mg/kg) | Dose Concentration (mg/mL) | Dosing Volume (mL/g) | Blood Sampling Time Points |
|---|---|---|---|---|---|---|
| 1 | SPRYCEL | Famotidine | 5 | 9.644 | 0.5 | Pre-dose, 5 min, |
| 2 | Dasatinib:EUDRAGIT L100-55 60:40 ASD | Famotidine | | | | 15 min, 30 min, |
| 3 | SPRYCEL | Pentagastrin | | | | 45 min, 1 hour, |
| 4 | Dasatinib:EUDRAGIT L100-55 60:40 ASD | Pentagastrin | | | | 2 hours, 4 hours, |
| 5 | Dasatinib:EUDRAGIT E100 50:50 ASD | Famotidine | | | | 6 hours, 10 hours, |

TABLE 19-continued

Study design for Example 4.

| Study Leg | Composition | Pre-treatment | Dose (mg/kg) | Dose Concentration (mg/mL) | Dosing Volume (mL/g) | Blood Sampling Time Points |
|---|---|---|---|---|---|---|
| 6 | Dasatinib:EUDRAGIT E100 50:50 ASD | Pentagastrin | | | | 16 hours, 24 hours, 36 hours |

Test compositions were orally dosed as suspensions comprising a buffered aqueous vehicle. Vehicles used for each composition are provided in Table 20. For the SPRYCEL test composition, the SPRYCEL tablets were crushed and mixed with the vehicle. All test composition suspensions were prepared at a final dasatinib concentration of 9.64 mg/mL and were prepared fresh on the day of dosing.

TABLE 20

Dosing vehicles for study legs 1-6 for Example 4.

| Study Leg | Composition | Pre-treatment | Vehicle |
|---|---|---|---|
| 1 | SPRYCEL (crushed) | Famotidine | 0.5% methylcellulose in 1 mM phosphate buffer |
| 2 | ASD (EUDRAGIT L100-55) | Famotidine | 0.5% methylcellulose in 0.5 mM citric acid buffer |
| 3 | SPRYCEL (crushed) | Pentagastrin | 0.5% methylcellulose in 1 mM phosphate buffer |
| 4 | ASD (EUDRAGIT L100-55) | Pentagastrin | 0.5% methylcellulose in 0.5 mM citric acid buffer |
| 5 | ASD (EUDRAGIT E100) | Famotidine | 0.5% methylcellulose in 1 mM phosphate buffer |
| 6 | ASD (EUDRAGIT E100) | Pentagastrin | 0.5% methylcellulose in 1 mM phosphate buffer |

Pharmacokinetics

Pharmacokinetic parameters were calculated from the time course of the plasma concentrations. The maximum plasma concentration ($C_{max}$) and the time to reach maximum plasma drug concentration ($T_{max}$) after oral dosing were determined from the data. Any samples for which the plasma concentration was below the limit of quantitation (0.5 ng/mL) were treated as zero for pharmacokinetic data analysis.

The original study protocol called for approximately 1 mL of gastric fluid to be aspirated for pH measurement. However, following leg 1, it was apparent that there was very little fluid in the stomach of the dogs and that the procedure was traumatic to the animals. For this reason, it was decided that gastric fluid samples would not be acquired for study legs 2 through 6.

Calculated pharmacokinetic parameters are given in Tables 21 through 26. The tables below include the following abbreviations and notations:

$C_{max}$: maximum plasma concentration;
$t_{max}$: time of maximum plasma concentration;
$t_{1/2}$: half-life;
$MRT_{last}$: mean residence time, calculated to the last observable time point;
$AUC_{last}$: area under the curve, calculated to the last observable time point;
$AUC_{0-inf}$: area under the curve, extrapolated to infinity;
ND: not determined.

TABLE 21

Individual and average pharmacokinetic parameters for Leg 1 of Example 4.
Famotidine Pretreatment—SPRYCEL

| Parameters | Dog 1 | Dog 2 | Dog 3 | Dog 4 | Dog 5 | Mean | SD |
|---|---|---|---|---|---|---|---|
| Animal Weight (kg) | 10.3 | 11.5 | 13.4 | 14.0 | 11.5 | 12.1 | 1.5 |
| Volume Dose (mL) | 5.2 | 5.8 | 6.7 | 7.0 | 5.8 | 6.1 | 0.7 |
| $C_{max}$ (ng/mL) | 1.92 | 1.84 | 2.20 | 3.95 | 5.94 | 3.17 | 1.77 |
| $t_{max}$ (hr) | 1.0 | 16 | 10 | 2.0 | 24 | 11 | 9.7 |
| $t_{1/2}$ (hr) | 5.86 | ND[b] | ND[b] | 12.4 | ND[b] | 9.16 | ND |
| $MRT_{last}$ (hr) | 7.47 | 12.6 | 8.53 | 6.30 | 21.3 | 11.2 | 6.08 |
| $AUC_{last}$ (hr · ng/mL) | 19.1 | 27.9 | 25.3 | 27.3 | 98.9 | 39.7 | 33.3 |
| $AUC_{0-inf}$ (hr · ng/mL) | 23.4 | ND[b] | ND[b] | ND[c] | ND[b] | ND | ND |
| Dose-normalized values[a] | | | | | | | |
| $AUC_{last}$ (hr · kg · ng/mL/mg) | 3.82 | 5.58 | 5.06 | 5.46 | 19.8 | 7.94 | 6.66 |
| $AUC_{0-inf}$ (hr · kg · ng/mL/mg) | 4.67 | ND[b] | ND[b] | ND[c] | ND[b] | ND | ND |

[a]Dose-normalized by dividing the parameter by the nominal dose in mg/kg;
[b]not determined because the terminal elimination phase was not observed;
[c]not determined because the $AUC_{0-inf}$ was a greater than 25% extrapolation above the $AUC_{last}$.

TABLE 22

Individual and average pharmacokinetic parameters for Leg 2 of Example 4.
Famotidine Pretreatment—ASD (EUDRAGIT L100-55)

| Parameters | Dog 1 | Dog 2 | Dog 3 | Dog 4 | Dog 5 | Mean | SD |
|---|---|---|---|---|---|---|---|
| Animal Weight (kg) | 9.6 | 10.7 | 12.6 | 13.3 | 10.6 | 11.4 | 1.5 |
| Volume Dose (mL) | 4.8 | 5.4 | 6.3 | 6.7 | 5.3 | 5.7 | 0.8 |
| $C_{max}$ (ng/mL) | 31.8 | 69.4 | 107 | 722 | 765 | 339 | 370 |
| $t_{max}$ (hr) | 4.0 | 4.0 | 0.75 | 0.25 | 0.25 | 1.9 | 2.0 |
| $t_{1/2}$ (hr) | 3.32 | 3.91 | 3.02 | 4.39 | 4.06 | 3.74 | 0.559 |
| $MRT_{last}$ (hr) | 5.79 | 7.22 | 5.53 | 5.94 | 5.62 | 6.02 | 0.688 |
| $AUC_{last}$ (hr · ng/mL) | 229 | 602 | 648 | 1411 | 941 | 766 | 441 |
| $AUC_{0-inf}$ (hr · ng/mL) | 232 | 615 | 653 | 1417 | 944 | 772 | 441 |
| Dose-normalized values[a] | | | | | | | |
| $AUC_{last}$ (hr · kg · ng/mL/mg) | 45.8 | 120 | 130 | 282 | 188 | 153 | 88.1 |
| $AUC_{0-inf}$ (hr · kg · ng/mL/mg) | 46.3 | 123 | 131 | 283 | 189 | 154 | 88.1 |

[a]Dose-normalized by dividing the parameter by the nominal dose in mg/kg.

TABLE 23

Individual and average pharmacokinetic parameters for Leg 3 of Example 4.
Pentagastrin Pretreatment—SPRYCEL

| Parameters | Dog 1 | Dog 2 | Dog 3 | Dog 4 | Dog 5 | Mean | SD |
|---|---|---|---|---|---|---|---|
| Animal Weight (kg) | 10.0 | 10.7 | 13.2 | 13.1 | 10.6 | 11.5 | 1.5 |
| Volume Dose (mL) | 5.0 | 5.4 | 6.6 | 6.6 | 5.3 | 5.8 | 0.8 |
| $C_{max}$ (ng/mL) | 63.2 | 208 | 55.8 | 166 | 66.4 | 112 | 70.3 |
| $t_{max}$ (hr) | 4.0 | 0.25 | 2.0 | 0.50 | 0.083 | 1.4 | 1.7 |
| $t_{1/2}$ (hr) | 3.10 | 5.29 | 2.97 | 3.02 | 5.14 | 3.91 | 1.20 |
| $MRT_{last}$ (hr) | 5.61 | 3.67 | 6.42 | 4.96 | 6.41 | 5.42 | 1.15 |
| $AUC_{last}$ (hr · ng/mL) | 390 | 452 | 344 | 550 | 442 | 436 | 77.0 |
| $AUC_{0-inf}$ (hr · ng/mL) | 406 | 490 | 347 | 553 | 459 | 451 | 78.8 |
| Dose-normalized values[a] | | | | | | | |
| $AUC_{last}$ (hr · kg · ng/mL/mg) | 78.0 | 90.4 | 68.8 | 110 | 88.4 | 87.1 | 15.4 |
| $AUC_{0-inf}$ (hr · kg · ng/mL/mg) | 81.3 | 98.0 | 69.3 | 111 | 91.7 | 90.2 | 15.8 |

[a]Dose-normalized by dividing the parameter by the nominal dose in mg/kg.

TABLE 24

Individual and average pharmacokinetic parameters for Leg 4 of Example 4.
Pentagastrin Pretreatment—ASD (EUDRAGIT L100-55)

| Parameters | Dog 1 | Dog 2 | Dog 3 | Dog 4 | Dog 5 | Mean | SD |
|---|---|---|---|---|---|---|---|
| Animal Weight (kg) | 10.2 | 10.9 | 13.0 | 13.1 | 10.5 | 11.5 | 1.4 |
| Volume Dose (mL) | 5.1 | 5.5 | 6.5 | 6.6 | 5.3 | 5.8 | 0.7 |
| $C_{max}$ (ng/mL) | 88.8 | 72.5 | 11.5 | 101 | 144 | 83.6 | 48.2 |
| $t_{max}$ (hr) | 4.0 | 2.0 | 2.0 | 2.0 | 0.25 | 2.1 | 1.3 |
| $t_{1/2}$ (hr) | 3.62 | 4.49 | 3.33 | 2.93 | 4.07 | 3.69 | 0.614 |
| $MRT_{last}$ (hr) | 6.95 | 7.07 | 4.95 | 5.32 | 3.96 | 5.65 | 1.34 |
| $AUC_{last}$ (hr · ng/mL) | 620 | 678 | 81.8 | 662 | 236 | 456 | 277 |
| $AUC_{0-inf}$ (hr · ng/mL) | 630 | 699 | 84.8 | 665 | 248 | 465 | 280 |
| Dose-normalized values[a] | | | | | | | |
| $AUC_{last}$ (hr · kg · ng/mL/mg) | 124 | 136 | 16.4 | 132 | 47.3 | 91.1 | 55.4 |
| $AUC_{0-inf}$ (hr · kg · ng/mL/mg) | 126 | 140 | 17.0 | 133 | 49.7 | 93.1 | 56.0 |

[a]Dose-normalized by dividing the parameter by the nominal dose in mg/kg.

TABLE 25

Individual and average pharmacokinetic parameters for Leg 5 of Example 4.
Famotidine Pretreatment—ASD (EUDRAGIT E100)

| Parameters | Dog 1 | Dog 2 | Dog 3 | Dog 4 | Dog 5 | Mean | SD |
|---|---|---|---|---|---|---|---|
| Animal Weight (kg) | 10.2 | 10.6 | 12.9 | 13.0 | 10.5 | 11.4 | 1.4 |
| Volume Dose (mL) | 5.1 | 5.3 | 6.5 | 6.5 | 5.3 | 5.7 | 0.7 |
| $C_{max}$ (ng/mL) | 153 | 178 | 71.1 | 305 | 19.5 | 145 | 110 |
| $t_{max}$ (hr) | 0.5 | 0.25 | 2.0 | 0.5 | 1.0 | 0.9 | 0.7 |
| $t_{1/2}$ (hr) | 4.58 | 3.97 | 3.48 | 5.30 | 2.19 | 3.90 | 1.18 |
| $MRT_{last}$ (hr) | 5.97 | 5.81 | 6.49 | 7.18 | 2.92 | 5.67 | 1.63 |
| $AUC_{last}$ (hr · ng/mL) | 734 | 601 | 603 | 1180 | 77.2 | 639 | 394 |
| $AUC_{0-inf}$ (hr · ng/mL) | 752 | 607 | 611 | 1187 | 81.0 | 648 | 395 |
| Dose-normalized values[a] | | | | | | | |
| $AUC_{last}$ (hr · kg · ng/mL/mg) | 147 | 120 | 121 | 236 | 15.4 | 128 | 78.8 |
| $AUC_{0-inf}$ (hr · kg · ng/mL/mg) | 150 | 121 | 122 | 237 | 16.2 | 130 | 79.1 |

[a]Dose-normalized by dividing the parameter by the nominal dose in mg/kg.

TABLE 26

Individual and average pharmacokinetic parameters for Leg 6 of Example 4.
Pentagastrin Pretreatment—ASD (EUDRAGIT E100)

| Parameters | Dog 1 | Dog 2 | Dog 3 | Dog 4 | Dog 5 | Mean | SD |
|---|---|---|---|---|---|---|---|
| Animal Weight (kg) | 10.1 | 10.6 | 13.0 | 13.6 | 10.7 | 11.6 | 1.58 |
| Volume Dose (mL) | 5.1 | 5.3 | 6.5 | 6.8 | 5.4 | 5.82 | 0.773 |
| $C_{max}$ (ng/mL) | 29.4 | 120 | 23.9 | 165 | 80.1 | 83.7 | 60.1 |
| $t_{max}$ (hr) | 0.25 | 6.0 | 2.0 | 1.0 | 0.25 | 1.9 | 2.4 |
| $t_{1/2}$ (hr) | 2.24 | 6.37 | 3.25 | 3.99 | 3.55 | 3.88 | 1.53 |
| $MRT_{last}$ (hr) | 2.80 | 9.29 | 5.43 | 5.31 | 3.70 | 5.30 | 2.49 |
| $AUC_{last}$ (hr · ng/mL) | 77.2 | 1262 | 146 | 680 | 193 | 472 | 502 |
| $AUC_{0-inf}$ (hr · ng/mL) | 80.8 | 1288 | 152 | 691 | 200 | 482 | 510 |
| Dose-normalized values[a] | | | | | | | |
| $AUC_{last}$ (hr · kg · ng/mL/mg) | 15.4 | 252 | 29.2 | 136 | 38.7 | 94.3 | 100 |
| $AUC_{0-inf}$ (hr · kg · ng/mL/mg) | 16.2 | 258 | 30.4 | 138 | 40.1 | 96.5 | 102 |

[a]Dose-normalized by dividing the parameter by the nominal dose in mg/kg.

Figure 4:
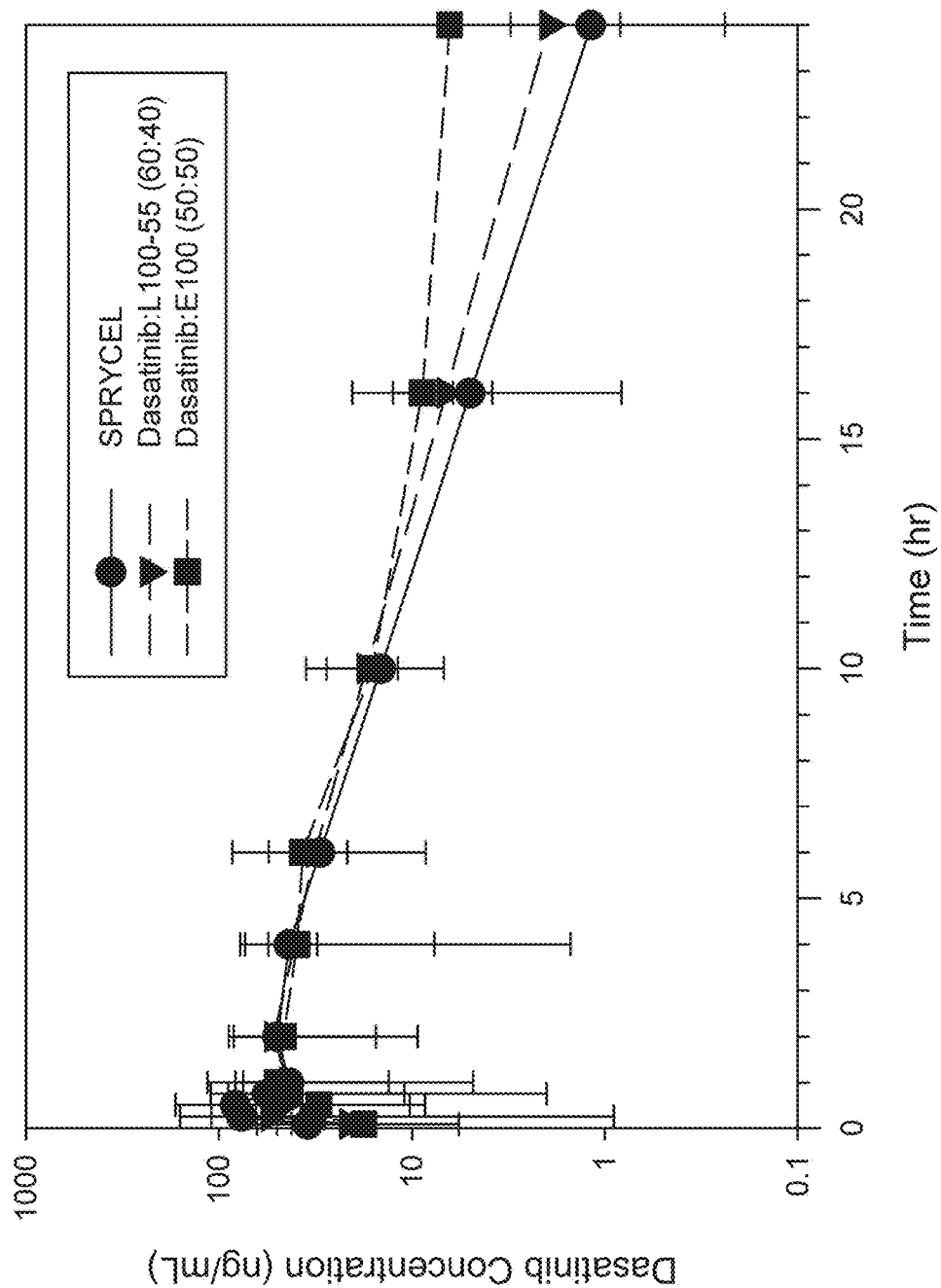
FIG. 4 shows canine in vivo pharmacokinetic profiles resulting from administration of an ASD of dasatinib and EUDRAGIT L100-55 at a w/w ratio (Dasatinib:EUDRAGIT L100-55) of 60:40, an ASD of dasatinib and EUDRAGIT E100 at a w/w ratio (Dasatinib:EUDRAGIT E100) of 50:50, and SPRYCEL, administered following pentagastrin pretreatment (pH 1-2), as described in Example 4.
Figure 5:
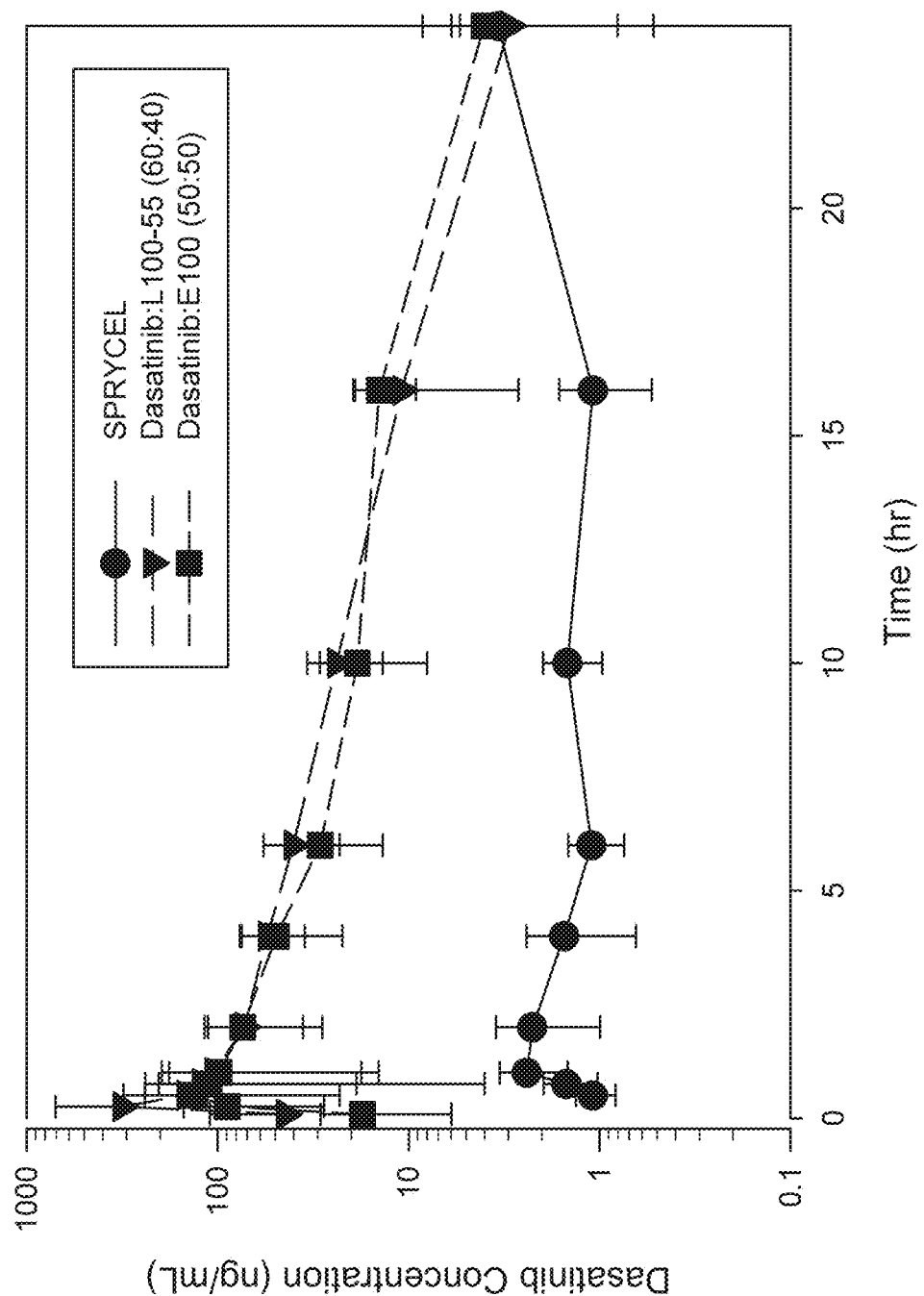
FIG. 5 shows canine in vivo pharmacokinetic profiles resulting from administration of an ASD of dasatinib and EUDRAGIT L100-55 at a w/w ratio (Dasatinib:EUDRAGIT L100-55) of 60:40, an ASD of dasatinib and EUDRAGIT E100 at a w/w ratio (Dasatinib:EUDRAGIT E100) of 50:50, and SPRYCEL, following famotidine pretreatment (pH 6-8), as described in Example 4.

The pharmacokinetic profiles obtained from administration of the test compositions and SPRYCEL are shown following pentagastrin pretreatment in FIG. 4 and famotidine pretreatment in FIG. 5.

As shown in FIG. 4, all three compositions performed essentially the same following pentagastrin pretreatment (i.e., at acidic pH). Average $C_{max}$ values were nearly identical for the two ASD compositions (83.6 and 83.7 ng/mL) and just slightly lower than SPRYCEL (112 ng/mL). Similarly, dose normalized $AUC_{last}$ values were in good agreement across all three test compositions (observed range of 87.1 to 94.3 hr·kg·ng/mL/mg), despite significant variability in the dog data. The data demonstrate that the absorption of dasatinib at conditions of low pH was consistent for the three test compositions.

Surprisingly, the two ASD compositions performed similarly despite EUDRAGIT L100-55 and EUDRAGIT E100 have very different polymer chemistry. EUDRAGIT E100 is known to be soluble in gastric fluid up to pH 5.0, while EUDRAGIT L100-55 is known to be insoluble in gastric fluid up to pH 5.5. Based on this information, it was unexpected that the EUDRAGIT L100-55 ASD composition would release drug at the same rate or to the same extent as the EUDRAGIT E100 ASD composition under low pH conditions.

Pretreatment with famotidine led to much different results, as shown in FIG. 5. The performance of SPRYCEL was markedly different at neutral pH than acidic pH. The $C_{max}$ for SPRYCEL at neutral pH following famotidine pretreatment (3.2 ng/mL) was nearly two orders-of-magnitude lower than what was observed at acidic pH (112 ng/mL). Similarly, the dose normalized $AUC_{last}$ for SPRYCEL was also dramatically lower following famotidine (7.94 hr·kg·ng/mL/mg) compared to pentagastrin (87.1 hr·kg·ng/mL/mg). These results were somewhat expected based upon published literature and the known poor solubility of dasatinib at elevated pH values.

In contrast, the two ASD compositions demonstrated significantly higher $C_{max}$ and AUC values compared to SPRYCEL following famotidine pretreatment. $C_{max}$ values for the two ASDs were highly variable but dramatically higher than SPRYCEL. Surprisingly, these peak concentrations were also higher than what was observed following pentagastrin pretreatment, despite the higher solubility of dasatinib at low pH. Both ASD compositions achieved similar dose normalized $AUC_{last}$ values (153 ng/mL for EUDRAGIT L100-55 ASD and 128 ng/mL for EUDRAGIT E100 ASD) under neutral pH conditions, which were again dramatically higher than what was observed for SPRYCEL (7.94 hr·kg·ng/mL/mg). The AUC values for the ASD compositions following famotidine pretreatment were also relatively consistent with the values obtained following pentagastrin pretreatment, which indicated that the preparation of dasatinib in an ASD was capable of significantly diminishing the effect of pH on dasatinib absorption kinetics.

Example 5. Human In Vivo Studies

A study was performed on human subjects to investigate the impact of elevated gastric pH on the pharmacokinetics observed upon administration of an ASD comprising dasatinib with EUDRAGIT L100-55 at a ratio of 60:40 (w/w) as compared to SPRYCEL (100 mg tablet) in the fasted state.

The ASD was dosed by way of an immediate-release tablet comprising the ASD. To prepare the ASD, appropriate quantities of dasatinib (anhydrous) and polymer were dissolved in a 1:1:1 (v/v/v) solvent mixture of methanol:ethanol:isopropyl acetate to provide a drug concentration of 1 wt.-%. The ASD was prepared by an electrospray technique similar to that used in prior Examples.

The resulting ASD was formulated into tablets containing 100 mg dasatinib. Granules were first formed by dry granulation of the ASD (50% w/w) with FUJICALIN, AVICEL PH-105, VIVASOL, AEROSIL R972, and magnesium stearate. Suitable quantities of the dry components were bag-blended and then roller-compacted to provide ribbons. Ribbons were processed through an oscillating granulator and sieved to provide suitably sized granules (20-24 mesh). Then, a tableting formulation was prepared using approximately 80% (w/w) granules along with additional quantities of AVICEL PH-105, VIVASOL, AEROSIL R972, and magnesium stearate. The formulation components were thoroughly v-blended, and then tableted using a tablet press to provide tablets containing 100 mg dasatinib ("Dasatinib ASD Tablet").

The human study employed a balanced, two-treatment, two period, two sequence, single dose, crossover design. Subjects were randomly divided as to whether they would receive the Dasatinib ASD Tablet in the first study period and the SPRYCEL tablet in the second study period, or vice versa. In each study period, subjects under fasting conditions received a single oral 20-mg dose of famotidine approximately three hours prior to dosing with either Dasatinib ASD Tablet (100 mg) or with SPRYCEL (100 mg) tablet. There was a washout period of 12 days between the two periods.

Plasma samples were taken within one hour prior to dosing with either the Dasatinib ASD Tablet or SPRYCEL tablet. Post-dose plasma samples were taken at suitable timepoints for evaluating the pharmacokinetic profile, up to 24 hours. In all, 24 subjects participated in the study.

Figure 6:
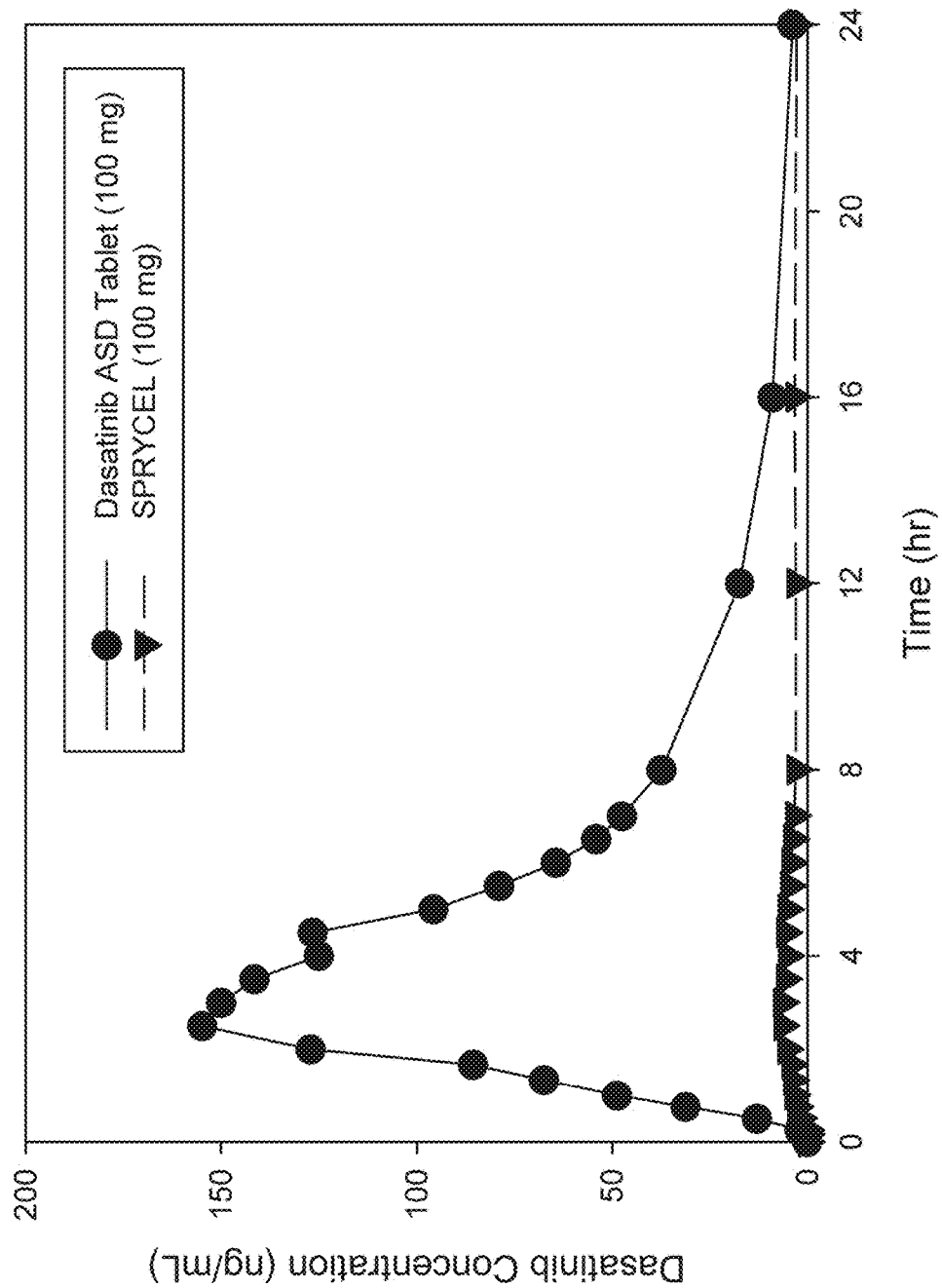
FIG. 6 shows human in vivo pharmacokinetic profiles resulting from administration of Dasatinib ASD Tablet and from administration of SPRYCEL tablet following famotidine pretreatment (pH 5+), as described in Example 5.

Plasma samples were analyzed for dasatinib content. Pharmacokinetic parameters were calculated from the data. FIG. 6, which presents the pharmacokinetic profiles based on untransformed data, shows that there was a substantial difference in the plasma concentrations of dasatinib after administration of the Dasatinib ASD Tablet as compared to after administration of the SPRYCEL tablet. Calculated pharmacokinetic parameters are presented in Table 27. These results show that subjects who were pretreated with famotidine and therefore had elevated gastric pH experienced substantially greater AUC and $C_{max}$ after administration of the Dasatinib ASD Tablet as compared to after administration of the SPRYCEL tablet, which resulted in very little dasatinib absorption.

TABLE 27

Calculated pharmacokinetic parameters at elevated gastric pH for Example 5.

| | Mean (untransformed) ± SD (CV %) | | % Ratio Dasatinib ASD Tablet/ SPRYCEL tablet |
|---|---|---|---|
| Parameters | Dasatinib ASD Tablet | SPRYCEL tablet | |
| $AUC_{0-inf}$ (ng × hr/mL) | 920.7 ± 220.3 (23.9) | 157.6 ± 81.3 (51.7) | 584 |
| $AUC_{last}$ (ng × hr/mL) | 889.1 ± 215.4 (24.2) | 80.8 ± 32.9 (40.7) | 1100 |
| $C_{max}$ (ng/mL) | 227.9 ± 69.6 (30.5) | 7.97 ± 4.11 (51.6) | 2860 |
| $t_{max}$ (hr) | 2.9 ± 0.9 | 5.6 ± 7.2 | n/a |
| $K_{el}$ (1/h) | 0.153 ± 0.037 | 0.088 ± 0.123 | n/a |
| $t_{1/2}$ (hr) | 4.9 ± 1.5 | 18.9 ± 15.0 | n/a |

$K_{el}$ = elimination rate constant
n/a = not applicable

A separate study was performed similarly, except that subjects were not provided a famotidine pretreatment, and accordingly did not have artificially modified gastric pH. (It should be noted that the two studies were done using different sets of subjects. Absorption of dasatinib is observed to have a high degree of inter-subject variability.) Calculated pharmacokinetic parameters for this study are presented in Table 28. Administration of Dasatinib ASD Tablet performed similarly to SPRYCEL tablet under these study conditions.

TABLE 28

Calculated pharmacokinetic parameters at unmodified gastric pH for Example 5.

| | Mean (untransformed) ± SD (CV %) | | % Ratio Dasatinib ASD Tablet/ SPRYCEL tablet |
|---|---|---|---|
| Parameters | Dasatinib ASD Tablet | SPRYCEL tablet | |
| $AUC_{0-inf}$ (ng × hr/mL) | 718.8 ± 152.0 (21.1) | 657.9 ± 222.1 (33.8) | 109 |
| $AUC_{last}$ (ng × hr/mL) | 697.9 ± 149.9 (21.4) | 602.4 ± 252.3 (41.8) | 116 |
| $C_{max}$ (ng/mL) | 168.6 ± 50.4 (29.9) | 154.8 ± 66.2 (42.8) | 109 |
| $t_{max}$ (hr) | 2.2 ± 1.1 | 1.7 ± 1.1 | n/a |
| $K_{el}$ (1/h) | 0.155 ± 0.030 | 0.150 ± 0.041 | n/a |
| $t_{1/2}$ (hr) | 4.6 ± 0.9 | 5.0 ± 1.5 | n/a |

$K_{el}$ = elimination rate constant
n/a = not applicable

Figure 7:
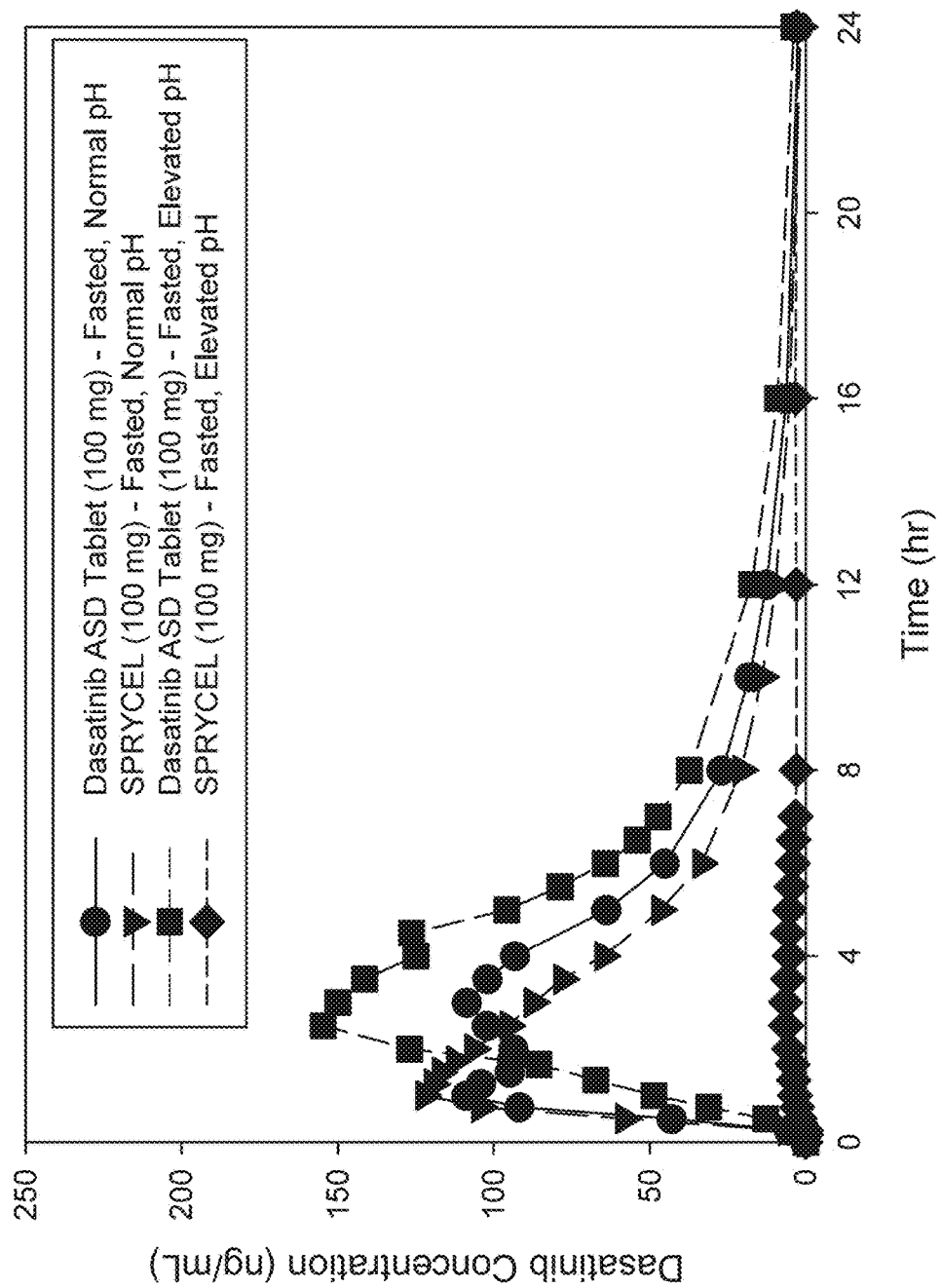
FIG. 7 shows human in vivo pharmacokinetic profiles resulting from administration of dasatinib ASD tablet and from administration of SPRYCEL tablet under fasting conditions, and resulting from administration of Dasatinib ASD Tablet and from administration of SPRYCEL tablet following famotidine pretreatment (pH 5+), as described in Example 5.

FIG. 7 shows pharmacokinetic profiles for this study, as well as for the elevated-pH study, and demonstrates that the pharmacokinetic profile resulting from administration of the Dasatinib ASD Tablet is similar regardless of whether the subject had artificially elevated gastric pH or not. In other words, elevated gastric pH had little effect on the absorption of dasatinib delivered via the Dasatinib ASD Tablet. This contrasts with SPRYCEL tablet, for which a dramatic decrease in exposure was observed after pretreatment with famotidine.

Notably, the pharmacokinetic profile and plasma concentration levels resulting from administration of the Dasatinib ASD Tablet with famotidine pretreatment resembled those resulting from administration of SPRYCEL tablet without famotidine pretreatment.

Figure 8:
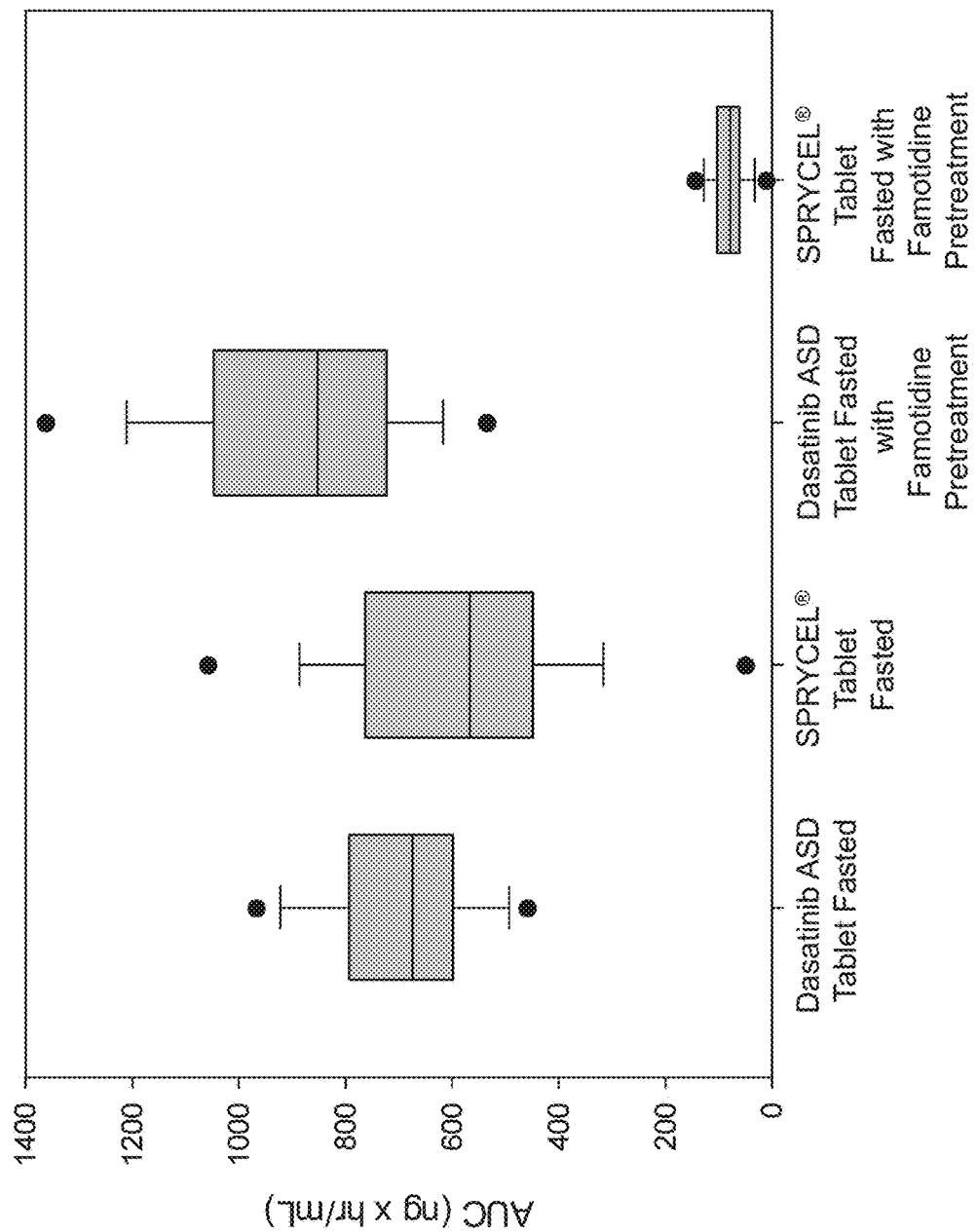
FIG. 8 shows a box plot graphically representing the AUC data and certain calculated statistical parameters from the studies described in Example 5.
Figure 9:
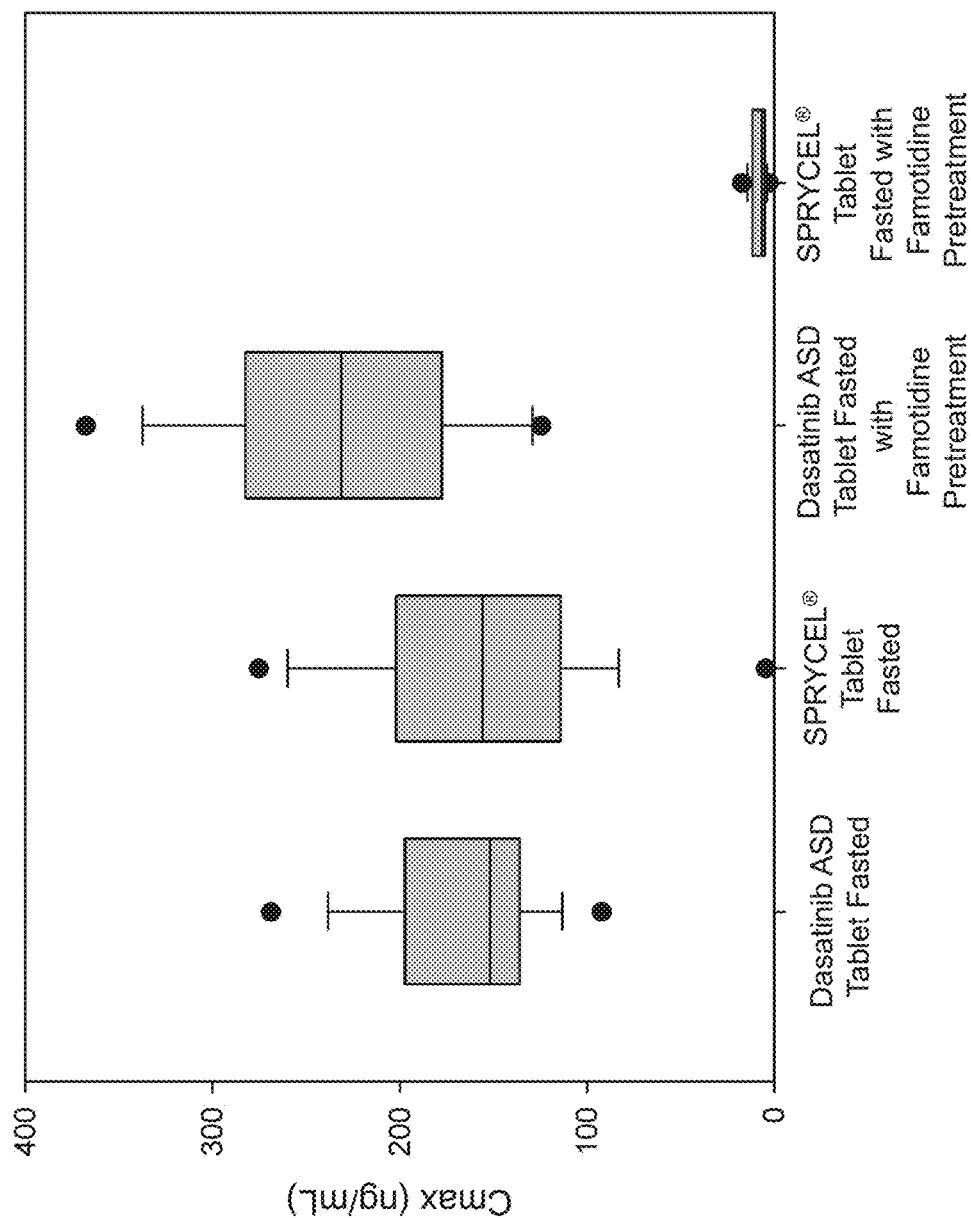
FIG. 9 shows a box plot graphically representing the $C_{max}$ data and certain calculated statistical parameters from the studies described in Example 5.

FIGS. 8 and 9 are box plots graphically representing the respective AUC (FIG. 8) and $C_{max}$ (FIG. 9) data and calculated statistical parameters from the two studies. These plots visually demonstrate that (i) Dasatinib ASD Tablet performed similarly regardless of whether the subject had artificially elevated gastric pH or not; (ii) the Dasatinib ASD Tablet performed similarly to SPRYCEL tablet when gastric pH was unmodified; and (iii) Dasatinib ASD Tablet outperformed SPRYCEL tablet when gastric pH was artificially elevated.

As can also be seen from FIGS. 8 and 9, at least one subject received almost no exposure to SPRYCEL, even without famotidine pretreatment. (This data point is graphically represented by the black dot near the bottom of the scale for both AUC in FIG. 8 and $C_{max}$ in FIG. 9.) Although not wishing to be bound, it is thought that this subject suffered from a condition that caused elevated gastric pH (such as hypochlorhydria or infection by *H. pylori*). If such a person were prescribed dasatinib therapy using SPRYCEL, the person would not be experiencing a therapeutic exposure of dasatinib. However, the same subject did experience a significant exposure of dasatinib when administered the Dasatinib ASD Tablet, as that subject's exposure is included in the graphical representation to the far left of the box plot.

Therefore, as a surprising and unexpected benefit, embodiments of the present disclosure can provide therapy to certain patients who might otherwise not be receiving the benefit of dasatinib therapy if using the conventional commercially available immediate release formulation of dasatinib.

Comparative Example

As a control, a spray-dried material of 100% dasatinib (i.e., no polymer) was prepared. A feedstock comprising 8 mg/mL of anhydrous dasatinib dissolved in a 60:40 (v/v) solvent mixture of methanol:MEK was prepared and spray-dried as with the amorphous solid dispersions in Example 6, below. After spray drying, the collected material was dried at 60° C. under vacuum for about 18 hours to remove residual solvents.

This spray-dried material was then promptly assessed by XRD, and exhibited crystalline character. The glass transition temperature ($T_g$) of the material was assessed, and a transition event was detected at 125.61° C. Water content was measured as 0.81% and the measured assay value was 97.4%.

Because this material reverted to crystalline character essentially immediately, it was not subjected to stability testing or further characterization.

Example 6. Preparation and Stability of High Drug Load Dasatinib ASDs

A study was performed to investigate the impact of drug load on the chemical and physical stability of several different ASDs comprising dasatinib and either EUDRAGIT L100-55 or METHOCEL E5 as the polymer. For this study, the drug:polymer ratio (w/w) in the ASDs were 70:30, 75:25, 80:20, 85:15, 90:10.

To prepare the ASDs, appropriate quantities of anhydrous dasatinib and polymer were dissolved in a 60:40 (v/v) solvent mixture of methanol:MEK to provide a liquid feedstock having a drug concentration of about 6 to about 10 mg/mL and a total solids concentration of about 8 to about 15 mg/mL. The ASDs were formed by spray drying the liquid feedstock using a Buchi B-290 spray dryer equipped with a two-fluid nozzle and a Buchi B-295 inert loop. For each spray run, the spray process parameters, such as inlet temperature, pump rate, outlet temperature, etc. were adjusted to achieve an acceptable outcome. Inlet temperature was set at 115-125° C., pump rate was set at 20%, and outlet temperature was 70-85° C. The resulting ASD was collected using a cyclone separator. After spray drying, each ASD was dried at 60° C. under vacuum for about 18 hours to remove residual solvents.

Each of the resulting ASDs was placed on stability under accelerated conditions at 40° C./75% RH. The ASDs were assessed at t=0 (i.e., after the secondary drying step), 2 weeks, 1 month, 2 months, 3 months, and 6 months for appearance, amorphicity, glass transition temperature, water content, and assay/total impurities.

Appearance

Each ASD was assessed for physical appearance at the initiation of the stability study (t=0) and at each time point on stability. All ASDs were white to off-white powders at t=0 and showed no visible change after storage under accelerated conditions for 6 months.

Amorphicity

Amorphicity (i.e., the lack of crystallinity) for the ASDs was assessed by XRD. Diffraction patterns were obtained using a Rigaku MiniFlex 600. The X-ray source was a long anode Cu Kα. Samples were prepared by placing a small amount of ASD powder on a Rigaku zero-background sample holder with a 0.1 mm indent. A glass slide was then used to firmly pack the powder and ensure the surface of the sample was level with the edge of the sample holder.

Rigaku Data Analysis Software PDXL 2.4.2.0 was used to determine crystallinity. Briefly, a linear background was obtained by connecting the beginning and end of each diffractogram. Peaks were then fitted to split pseudo-Voigt shape by the Lorentzian function. Generally, narrow peaks with full width at half maximum (FWHM) less than 1° were assigned as crystalline phase. If no crystalline phase was detected, the sample was deemed to be amorphous.

All Dasatinib:EUDRAGIT L100-55 ASDs remained completely amorphous after storage for six months at 40° C./75% RH, regardless of the drug load.

For Dasatinib:METHOCEL E5 ASDs, the 70:30 ASD showed some crystalline character after storage for two months at 40° C./75% RH, and the 75:25 and 80:20 ASDs showed some crystalline character after storage for six months at 40° C./75% RH. However, the 85:15 and 90:10 ASDs remained completely amorphous after storage for six months at 40° C./75% RH.

These results demonstrate that the higher drug load was beneficial for providing physical stability under accelerated conditions for these dasatinib ASDs, and indicate a promising approach for stability under real-world storage conditions.

Glass Transition Temperature

Glass transition temperature ($T_g$) of the ASDs was analyzed using modulated differential scanning calorimetry (mDSC), which was run on a TA Instruments Model Q200 equipped with a RCS90 refrigerated cooling system. In general, about 5-10 mg of ASD powder was loaded in a TA $T_{zero}$ low-mass aluminum pan and sealed with a $T_{zero}$ lid. Instrument details and measurement conditions are provided in Table 29. The results of the mDSC analysis are provided in Tables 30 and 31.

TABLE 29

TA Q200 DSC instrument and measurement conditions.

| Parameter | Conditions |
|---|---|
| DSC Mode | Modulated |
| Test | MDSC heat only |
| Method | Modulate + 0.48° C. every 60 sec, Temperature ramp 3.00° C./min from 0.00° C. to 200.00° C. |
| Data Sampling Interval | 0.20 sec |

TABLE 30

Glass transition temperature data for the Dasatinib:EUDRAGIT L100-55 ASDs of Example 6, stored at 40° C./75% RH through 6 months.

| | $T_g$ (° C.) Dasatinib:EUDRAGIT L100-55 | | | | |
|---|---|---|---|---|---|
| Time Point | 70:30 | 75:25 | 80:20 | 85:15 | 90:10 |
| 0 | 136.55 | 132.83 | 128.93 | 134.14 | 133.03 |
| 2 weeks | 138.61 | 137.73 | 132.82 | 135.38 | 133.85 |
| 1 month | 137.49 | 135.33 | 133.19 | 135.49 | 133.18 |
| 2 months | 138.74 | 134.33 | 134.01 | 134.96 | 132.63 |
| 3 months | 140.38 | 137.87 | 134.33 | 135.76 | 134.47 |
| 6 months | 139.59 | 138.01 | 135.04 | 137.13 | 134.35 |

TABLE 31

Glass transition temperature data for the Dasatinib:METHOCEL E5 ASDs of Example 6, stored at 40° C./75% RH through 6 months.

| | $T_g$ (° C.) Dasatinib:METHOCEL E5 | | | | |
|---|---|---|---|---|---|
| Time Point | 70:30 | 75:25 | 80:20 | 85:15 | 90:10 |
| 0 | 119.62 | 119.61 | 119.77 | 127.58 | 128.42 |
| 2 weeks | 124.39 | 123.79 | 123.58 | 127.92 | 128.24 |
| 1 month | 125.19 | 125.44 | 124.37 | 128.39 | 129.13 |
| 2 months | 125.81 | 126.05 | 125.91 | 128.86 | 129.51 |
| 3 months | 126.91 | 125.62 | 125.88 | 129.46 | 129.63 |
| 6 months | 127.72 | 128.10 | 127.01 | 129.94 | 130.47 |

For all the ASDs, there was a slight change in $T_g$ on stability, but each sample did demonstrate a thermal event consistent with a glass transition temperature.

Water Content

Water content was determined using a coulometric Karl Fischer Titration. Approximately 40-50 mg of ASD powder was weighed into a glass Stromboli sample vial and the vial was immediately sealed with a foil coated vial cover, and a rubber vial cap cover was placed on top of the sample vial.

The results, presented in Tables 32 and 33, show that the water content rose between t=0 and 2 weeks due to moisture absorption from the controlled environment. The water content then generally remained steady from 2 weeks through 6 months, which indicates that the moisture in the amorphous solid dispersions had reached equilibrium with the environment.

TABLE 32

Water content data for the Dasatinib:EUDRAGIT L100-55 ASDs of Example 6, stored at 40° C./75% RH through 6 months.

| | Water Content (% by weight) Dasatinib:EUDRAGIT L100-55 | | | | |
|---|---|---|---|---|---|
| Time Point | 70:30 | 75:25 | 80:20 | 85:15 | 90:10 |
| 0 | 0.47 | 0.44 | 0.39 | 1.08 | 1.26 |
| 2 weeks | 7.16 | 7.18 | 6.94 | 7.11 | 6.72 |
| 1 month | 7.48 | 7.28 | 7.04 | 6.40 | 7.12 |
| 2 months | 7.17 | 6.62 | 6.91 | 7.12 | 6.74 |
| 3 months | 7.29 | 7.26 | 7.03 | 7.06 | 6.71 |
| 6 months | 7.65 | 7.69 | 7.43 | 5.27 | 5.33 |

TABLE 33

Water content data for the Dasatinib:METHOCEL E5 ASDs of Example 6, stored at 40° C./75% RH through 6 months.

| | Water Content (% by weight) Dasatinib:METHOCEL E5 | | | | |
|---|---|---|---|---|---|
| Time Point | 70:30 | 75:25 | 80:20 | 85:15 | 90:10 |
| 0 | 0.42 | 0.42 | 0.43 | 1.10 | 1.18 |
| 2 weeks | 6.94 | 6.67 | 6.44 | 6.77 | 6.33 |
| 1 month | 6.98 | 6.88 | 6.56 | 6.69 | 6.00 |
| 2 months | 6.64 | 6.59 | 6.39 | 6.45 | 6.10 |
| 3 months | 6.66 | 6.58 | 6.28 | 6.41 | 6.18 |
| 6 months | 6.41 | 6.64 | 6.52 | 3.17 | 2.77 |

Assay and Total Impurities

Assay and total impurities of the ASDs were assessed using either an Agilent 1200 HPLC or a Waters Alliance e2695 HPLC. The instrument and measurement conditions are specified in Table 34 and the gradient profile in Table 35.

TABLE 34

HPLC instrument and measurement conditions used for the assay/impurity analysis of Example 6.

| Parameter | Condition |
|---|---|
| Column | Waters XBridge C18, 3.0 × 150 mm, 3.5 μm particle size |
| Flow rate | 0.7 mL/min |
| Mobile Phase A | 20 mM Ammonium Bicarbonate, pH 9.0 |
| Mobile Phase B | Acetonitrile |
| Elution Program | Gradient (see Table 35) |
| Injection Volume | 10 μL |
| Column Temperature | 45° C. |
| Detector Wavelength | 324 nm |

TABLE 35

HPLC instrument gradient profile used for the assay/impurity analysis of Example 6.

| Time (min) | % Mobile Phase A | % Mobile Phase B |
|---|---|---|
| 0.00 | 95 | 5 |
| 6.00 | 80 | 20 |
| 28.00 | 60 | 40 |
| 35.00 | 0 | 100 |
| 35.10 | 95 | 5 |
| 38.00 | 95 | 5 |
| 40.00 | 85.0 | 15.0 |

Assay values are listed in Table 36 for Dasatinib:EU-DRAGIT L100-55 ASDs and in Table 37 for Dasatinib:

METHOCEL E5 ASDs at t=0 and at each stability time point. These reported assay values are corrected for the measured water content of the sample.

TABLE 36

Assay data for the Dasatinib:EUDRAGIT L100-55 ASDs of Example 6, stored at 40° C./75% RH through 6 months.

| | Assay Value (% label claim, corrected for water content) Dasatinib:EUDRAGIT L100-55 | | | | |
|---|---|---|---|---|---|
| Time Point | 70:30 | 75:25 | 80:20 | 85:15 | 90:10 |
| 0 | 99.3 | 97.6 | 97.6 | 98.6 | 98.4 |
| 2 weeks | 99.6 | 98.5 | 98.8 | 100.5 | 99.8 |
| 1 month | 100.7 | 99.0 | 99.0 | 101.4 | 95.9 |
| 2 months | 100.6 | 98.1 | 98.5 | 100.9 | 99.4 |
| 3 months | 103.0 | 101.4 | 100.0 | NA[a] | NA[a] |
| 6 months | 99.6 | 98.1 | 98.3 | 97.9 | 99.2 |

[a]data is not available due to method error

TABLE 37

Assay data for the Dasatinib:METHOCEL E5 ASDs of Example 6, stored at 40° C./75% RH through 6 months.

| | Assay Value (% label claim, corrected for water content) Dasatinib:METHOCEL E5 | | | | |
|---|---|---|---|---|---|
| Time Point | 70:30 | 75:25 | 80:20 | 85:15 | 90:10 |
| 0 | 100.7 | 100.3 | 100.8 | 97.8 | 98.0 |
| 2 weeks | 100.3 | 99.9 | 99.0 | 100.7 | 100.5 |
| 1 month | 102.0 | 100.8 | 100.7 | 106.6 | 101.0 |
| 2 months | 101.8 | 100.9 | 100.1 | 100.1 | 99.5 |
| 3 months | 99.3 | 97.5 | 97.4 | NA[a] | NA[a] |
| 6 months | 100.8 | 100.0 | 99.2 | 97.9 | 97.8 |

[a]data is not available due to method error

Measured total impurities are reported in Table 38 for Dasatinib:EUDRAGIT L100-55 ASDs and in Table 39 for Dasatinib:METHOCEL E5 ASDs.

TABLE 38

Total impurities data for the Dasatinib:EUDRAGIT L100-55 ASDs of Example 6, stored at 40° C./75% RH through 6 months.

| | Total Impurities (% Area) Dasatinib:EUDRAGIT L100-55 | | | | |
|---|---|---|---|---|---|
| Time Point | 70:30 | 75:25 | 80:20 | 85:15 | 90:10 |
| 0 | 0.17 | 0.17 | 0.16 | 0.17 | 0.17 |
| 2 weeks | 0.23 | 0.22 | 0.21 | 0.22 | 0.22 |
| 1 month | 0.31 | 0.29 | 0.34 | 0.34 | 0.28 |
| 2 months | 0.44 | 0.43 | 0.39 | 0.36 | 0.36 |
| 3 months | 0.59 | 0.53 | 0.52 | NA[a] | NA[a] |
| 6 months | 0.79 | 0.77 | 0.66 | 0.51 | 0.52 |

[a]data is not available due to method error

TABLE 39

Total impurities data for the Dasatinib:METHOCEL E5 ASDs of Example 6, stored at 40° C./75% RH through 6 months.

| | Total Impurities (% Area) Dasatinib:METHOCEL E5 | | | | |
|---|---|---|---|---|---|
| Time Point | 70:30 | 75:25 | 80:20 | 85:15 | 90:10 |
| 0 | 0.17 | 0.17 | 0.14 | 0.17 | 0.17 |
| 2 weeks | 0.21 | 0.20 | 0.20 | 0.24 | 0.24 |
| 1 month | 0.28 | 0.36 | 0.36 | 0.28 | 0.33 |
| 2 months | 0.41 | 0.42 | 0.40 | 0.40 | 0.41 |
| 3 months | 0.58 | 0.54 | 0.50 | NA[a] | NA[a] |
| 6 months | 0.72 | 0.74 | 0.75 | 0.47 | 0.51 |

[a]data is not available due to method error

Based on the assay and total impurities data, it can be concluded that the ASDs exhibited acceptable chemical stability under accelerated conditions throughout the stability study.

Example 7. In Vitro Dissolution of Tablets Comprising Dasatinib ASDs

A study was performed to investigate the in vitro dissolution performance of tablets comprising ASDs of the disclosure, in a variety of biorelevant dissolution media. SPRYCEL, the reference listed drug, was also included in the study as a benchmark, in the form of 100 mg immediate-release tablets.

Test tablets containing 100 mg dasatinib (in the form of Dasatinib:EUDRAGIT L100-55 ASD or Dasatinib: METHOCEL E5 ASD) were prepared using appropriate ASDs, as follows. ASDs were first prepared according to the method given in Example 1, at various drug loads (drug:polymer ratios of 60:40, 70:30, and 80:20). Granules were then formed by dry granulation of the ASD with FUJICALIN, AVICEL PH-105, VIVASOL, AEROSIL R972, and magnesium stearate. Suitable quantities of the dry components were bag-blended and then roller-compacted to provide ribbons. Ribbons were processed through an oscillating granulator and sieved to provide suitably sized granules (20-24 mesh).

Then, a tableting formulation was prepared using approximately 80% (w/w) granules along with suitable quantities of AVICEL PH-102, VIVASOL, AEROSIL R972, and magnesium stearate. The formulation components were thoroughly v-blended, and then tableted using a tablet press to provide test tablets containing 100 mg dasatinib ("Dasatinib ASD Tablet").

For the dissolution testing, the biorelevant dissolution media included the following:
Medium A: pH 4 Acetate buffer (50 mM) with 1% Triton X-100;
Medium B: pH 5.8 Fed-State Simulated Intestinal Fluid ("FeSSIF");
Medium C: pH 5.5 Acetate buffer (50 mM).
The composition of Medium B is given in Table 40.

TABLE 40

Composition of Medium B: pH 5.8 FeSSIF.

| Component | Concentration |
|---|---|
| Taurocholate | 10 mM |
| Phospholipids | 2 mM |
| Oleate | 0.8 mM |
| Glycerol monooleate | 5 mM |
| Sodium | 218 mM |

TABLE 40-continued

Composition of Medium B: pH 5.8 FeSSIF.

| Component | Concentration |
|---|---|
| Chloride | 125 mM |
| Maleic acid | 55 mM |

For the dissolution tests, a Vankel model VK7000 dissolution bath was fitted with a USP Apparatus II system equipped with 1000-mL vessels and paddles (60 rpm). The vessels were charged with one of the dissolution media (A, B, or C), and the media equilibrated to 37° C. A sample (Dasatinib ASD Tablet or SPRYCEL) was introduced into each vessel at t=0. Sampling timepoints were at t=10 min, 15 min, 30 min, and 45 min. At sampling timepoints, a sample was pulled from each vessel using a syringe and stainless steel cannula fitted with 10 μm full flow filter. Samples were immediately filtered through 0.2 μm nylon filter and then diluted 1:1 (v/v) with a 50:50 ethanol:methanol (v/v) mixture.

Samples were subsequently analyzed by HPLC using either an Agilent 1200 HPLC or a Waters Alliance e2695 HPLC. The instrument and measurement conditions are specified in Table 41 and the gradient profile in Table 42.

TABLE 41

HPLC instrument and measurement conditions used for the dissolution concentration analysis of Example 7.

| Parameter | Condition |
|---|---|
| Column | Waters XBridge C18, 3.0 × 150 mm, 3.5 μm particle size |
| Flow rate | 0.8 mL/min |
| Mobile Phase A | 20 mM Ammonium Bicarbonate, pH 9.0 |
| Mobile Phase B | Acetonitrile |
| Elution Program | Gradient (see Table 42) |
| Injection Volume | 10 μL |
| Column Temperature | 45° C. |
| Detector Wavelength | 324 nm |

TABLE 42

HPLC instrument gradient profile used for the dissolution concentration analysis of Example 7.

| Time (min) | % Mobile Phase A | % Mobile Phase B |
|---|---|---|
| 0.00 | 71 | 29 |
| 10.00 | 71 | 29 |
| 11.00 | 0 | 100 |
| 12.00 | 0 | 100 |
| 12.01 | 71 | 29 |
| 14.00 | 71 | 29 |

Figure 10:
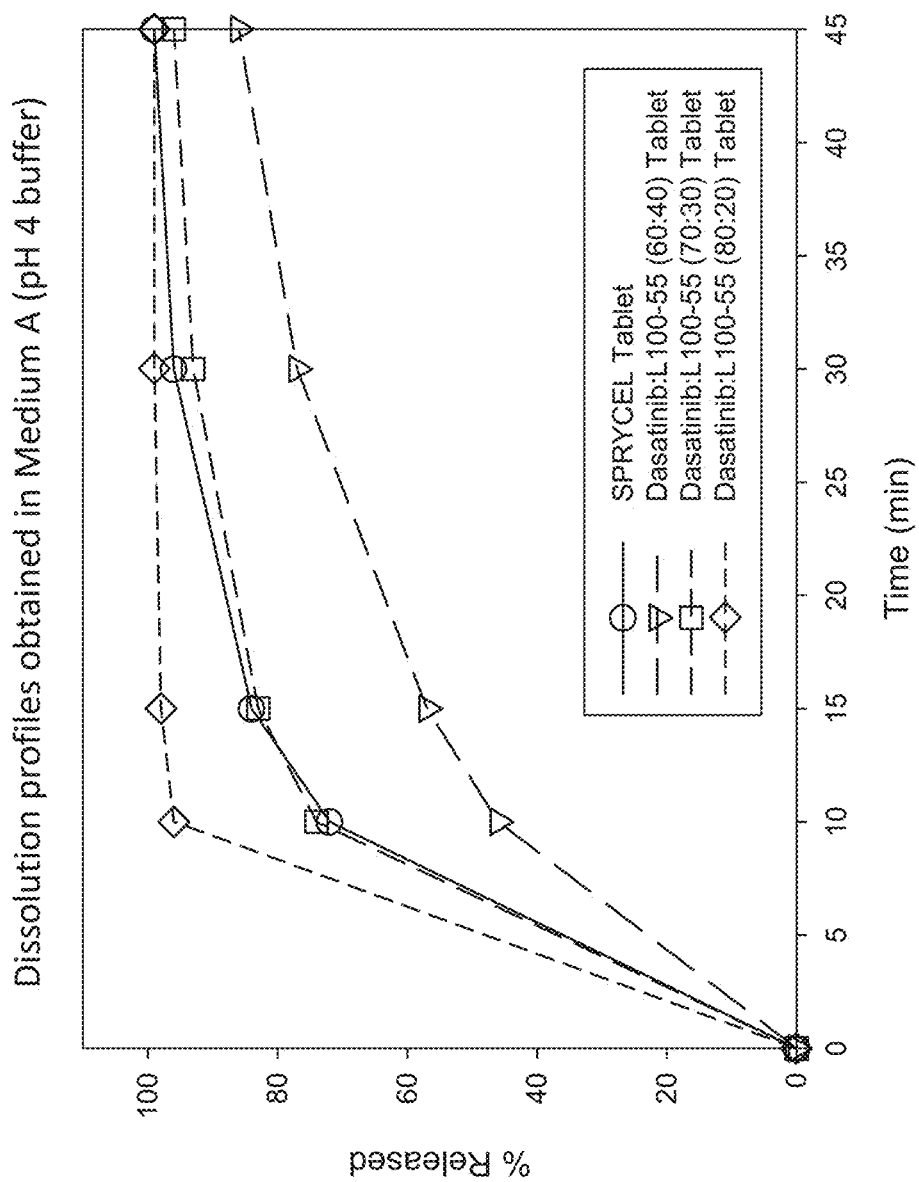
FIG. 10 shows in vitro dissolution profiles obtained using a pH 4 buffer (Medium A) for tablets comprising Dasatinib:EUDRAGIT L100-55 ASDs and for the SPRYCEL reference product, as detailed in Example 7.
Figure 11:
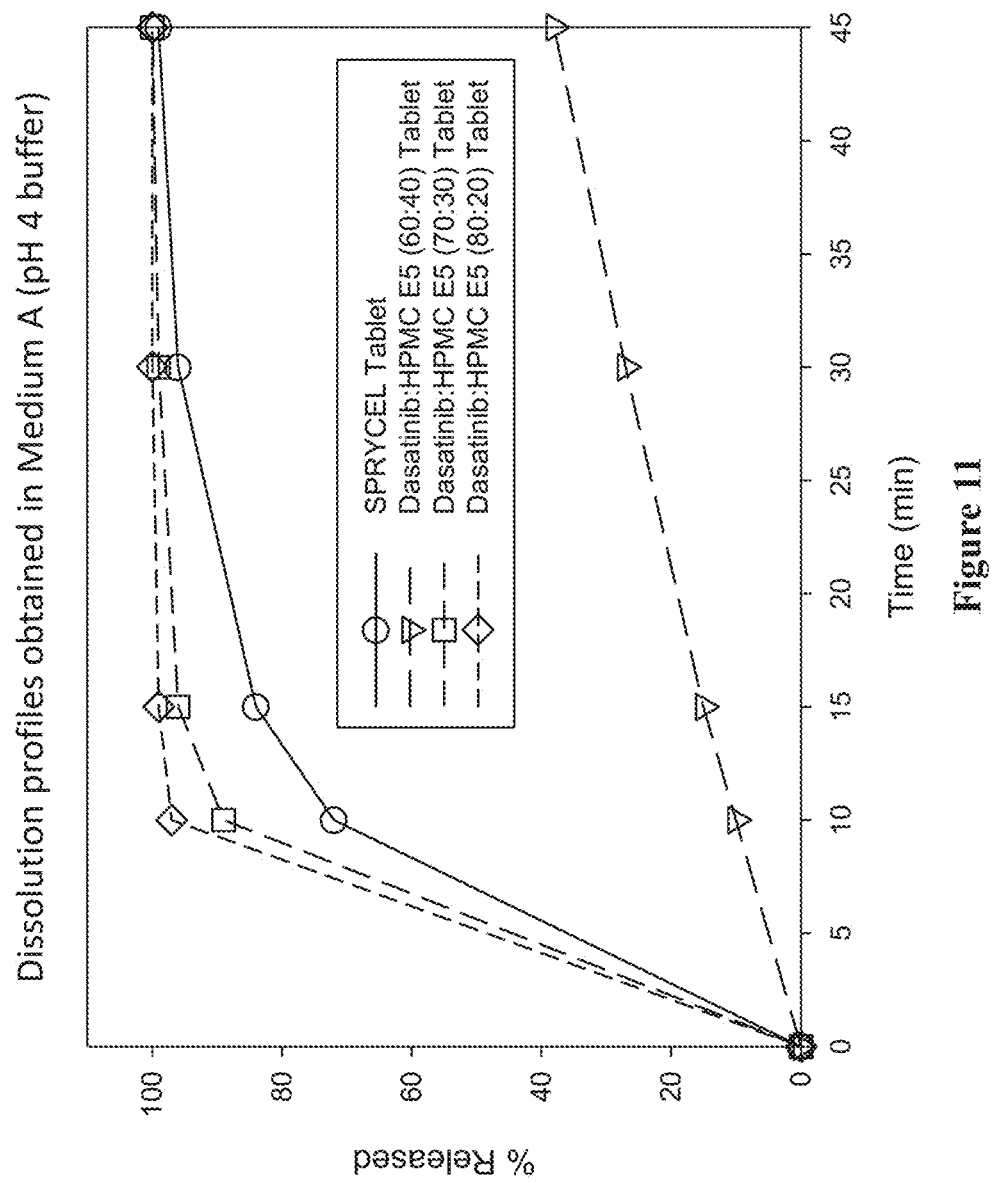
FIG. 11 shows in vitro dissolution profiles obtained using a pH 4 buffer (Medium A) for tablets comprising Dasatinib:METHOCEL E5 ASDs and for the SPRYCEL reference product, as detailed in Example 7.

The resulting dissolution curves are shown in FIGS. 10-13. FIG. 10 shows the dissolution curves obtained at pH 4 (Medium A) for tablets comprising Dasatinib:EUDRAGIT L100-55 ASDs. FIG. 11 shows dissolution curves obtained at pH 4 (Medium A) for tablets comprising Dasatinib: METHOCEL E5 ASDs. For both ASD systems, the ASDs having a drug load of 70% or greater performed as well or better (i.e., faster and/or more complete dissolution) than the SPRYCEL reference. In contrast, an ASD having a drug load of 60% did not perform as well as the SPRYCEL reference.

Figure 12:
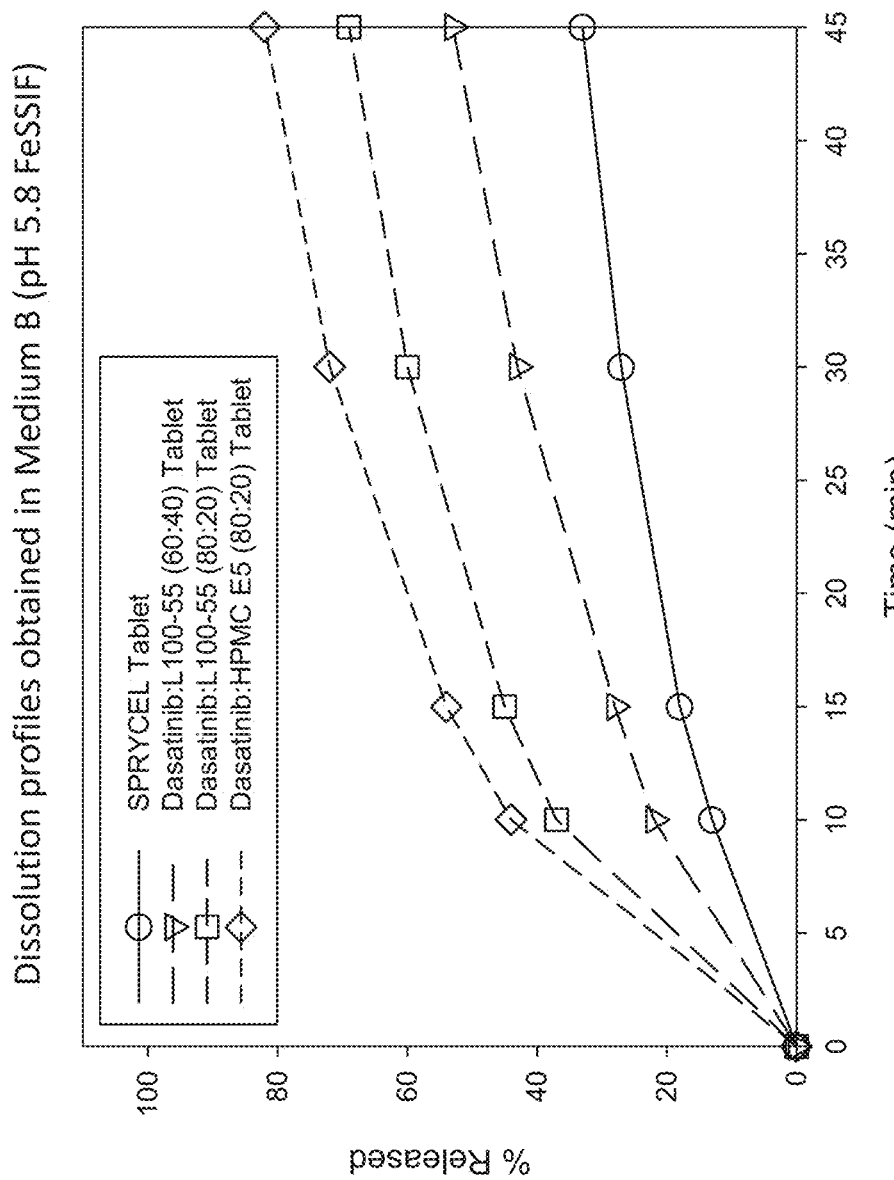
FIG. 12 shows in vitro dissolution profiles obtained using FeSSIF (Medium B) at pH 5.8 for tablets comprising Dasatinib:EUDRAGIT L100-55 ASD at 60% and 80% drug load, for tablets comprising Dasatinib:METHOCEL E5 ASD at 80% drug load, and for the SPRYCEL reference product, as detailed in Example 7.

FIG. 12 shows dissolution curves obtained with the pH 5.8 FeSSIF (Medium B) for tablets comprising Dasatinib: EUDRAGIT L100-55 ASD at 60% and 80% drug load, and for tablets comprising Dasatinib:METHOCEL E5 ASD at 80% drug load. Each of the ASD tablets performed better than the SPRYCEL reference under this condition.

Figure 13:
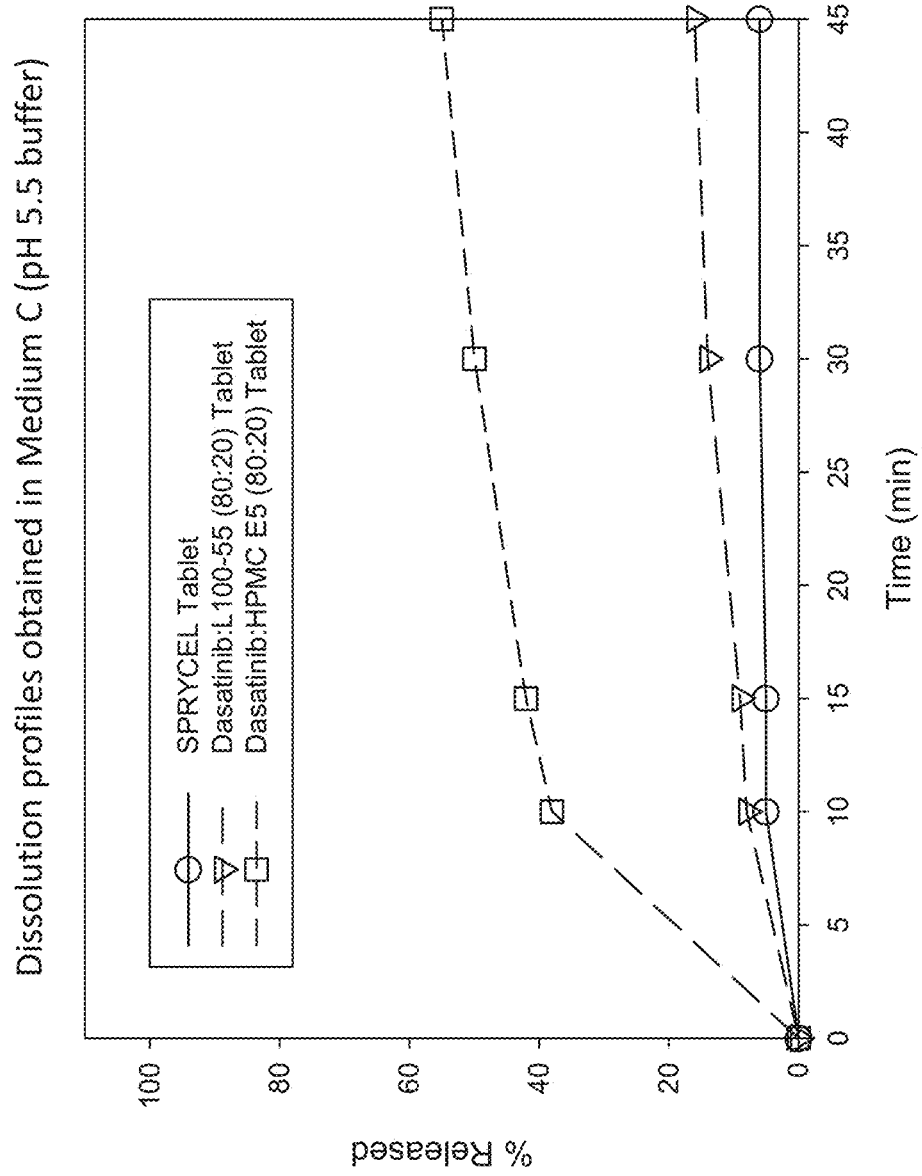
FIG. 13 shows in vitro dissolution profiles obtained using a pH 5.5 buffer (Medium C) for tablets comprising Dasatinib:EUDRAGIT L100-55 ASD at 60% and 80% drug load, for tablets comprising Dasatinib:METHOCEL E5 ASD at 80% drug load, and for the SPRYCEL reference product, as detailed in Example 7.

FIG. 13 shows dissolution curves obtained at pH 5.5 (Medium C) for tablets comprising Dasatinib:EUDRAGIT L100-55 ASD at 80% drug load, and for tablets comprising Dasatinib:METHOCEL E5 ASD at 80% drug load. Each of the ASD tablets performed better than the SPRYCEL reference under this condition.

Taken as a whole, these data support the conclusion that the ASDs of the disclosure provide enhanced solubility in biorelevant media under conditions of elevated pH relative to normal fasted gastric pH. This indicates that the ASDs are likely to provide enhanced in vivo bioavailability at elevated pH as compared to a formulation comprising crystalline dasatinib.

Example 8. In Vivo Pharmacokinetic Study of Tablets Comprising Dasatinib ASD A study was performed to evaluate the in vivo pharmacokinetic performance of tablets comprising ASDs of the disclosure. SPRYCEL, the reference listed drug, was also included in the study as a benchmark, in the form of 100 mg immediate-release tablets.

The test tablet was the Dasatinib ASD Tablet from Example 5. SPRYCEL was included in the study as the reference product, in the form of 100 mg immediate-release tablets.

The human study employed a balanced, two-treatment, four period, two sequence, single dose, fully replicated crossover design. Separate studies were done under fasted and fed conditions. (It should be noted that the two studies were done using different sets of subjects. Absorption of dasatinib is observed to have a high degree of inter-subject variability.)

Subjects were randomly divided as to the order in which they would receive the test product (Dasatinib ASD Tablet) and the reference product (SPRYCEL tablet) in the study periods. There was a washout period of at least 7 days between the periods.

In the fasted study, subjects were fasted overnight for at least 10 hours before administration and for at least 4 hours after administration in each study period. Doses were administered with a 240-mL portion of water.

In the fed study, subjects were fasted overnight for at least 10 hours, and then were fed a high-fat, high-calorie breakfast starting 30 minutes prior to administration. Subjects then did not eat again for at least 4 hours after administration in each study period. Doses were administered with a 240-mL portion of water.

Plasma samples were taken within one hour prior to dosing. Post-dose plasma samples were taken at suitable timepoints for evaluating the pharmacokinetic profile, up to 24 hours. At least 18 subjects completed each period of each study.

Plasma samples were analyzed for dasatinib content. Pharmacokinetic parameters were calculated from the data. Calculated pharmacokinetic parameters are presented in Table 43 for the fasted study (n=19) and Table 44 for the fed study (n=18).

TABLE 43

Calculated pharmacokinetic parameters under fasted conditions for Example 8.

| Parameters | Mean (untransformed) ± SD (CV %) | | Within-Subject Variability ($S_{WR}$) SPRYCEL tablet |
|---|---|---|---|
| | Dasatinib ASD Tablet | SPRYCEL tablet | |
| $AUC_{0\_inf}$ (ng × hr/mL) | 718.8 ± 152.0 (21.1) | 657.9 ± 222.1 (33.8) | 0.2359 |
| $AUC_{last}$ (ng × hr/mL) | 697.9 ± 149.9 (21.4) | 602.4 ± 252.3 (41.8) | 0.2442 |
| $C_{max}$ (ng/mL) | 168.6 ± 50.4 (29.9) | 154.8 ± 66.2 (42.8) | 0.3814 |
| $t_{max}$ (hr) | 2.2 ± 1.1 | 1.7 ± 1.1 | n/a |
| $K_{el}$ (1/h) | 0.155 ± 0.030 | 0.150 ± 0.041 | n/a |
| $t_{1/2}$ (hr) | 4.6 ± 0.9 | 5.0 ± 1.5 | n/a |

$K_{el}$ = elimination rate constant
n/a = not applicable

TABLE 44

Calculated pharmacokinetic parameters under fed conditions for Example 8.

| Parameters | Mean (untransformed) ± SD (CV %) | | Within-Subject Variability ($S_{WR}$) SPRYCEL tablet |
|---|---|---|---|
| | Dasatinib ASD Tablet | SPRYCEL tablet | |
| $AUC_{0\_inf}$ (ng × hr/mL) | 444.8 ± 99.1 (22.3) | 454.1 ± 99.3 (21.9) | 0.0962 |
| $AUC_{last}$ (ng × hr/mL) | 419.5 ± 95.1 (22.7) | 426.5 ± 94.9 (22.3) | 0.0991 |
| $C_{max}$ (ng/mL) | 75.4 ± 25.0 (33.1) | 79.6 ± 20.2 (25.4) | 0.1418 |
| $t_{max}$ (hr) | 2.979 ± 1.524 | 2.665 ± 1.552 | n/a |
| $K_{el}$ (1/h) | 0.144 ± 0.040 | 0.137 ± 0.036 | n/a |
| $t_{1/2}$ (hr) | 5.200 ± 1.452 | 5.408 ± 1.364 | n/a |

$K_{el}$ = elimination rate constant
n/a = not applicable

For any log-transformed parameter where the within-subject SD for the reference product ($S_{WR}$)≥0.294, the Scaled Average Bioequivalence (SABE) method was used. The upper 95% confidence bound on the linearized SABE statistic was calculated. For those log-transformed parameters where the within-subject SD for the reference product ($S_{WR}$)≤0.294, the Average Bioequivalence (ABE) method was used.

Based on the statistical analysis for the fasted study, the estimated 90% confidence interval for log transformed pharmacokinetic parameters $AUC_{last}$ was not within the acceptance criteria of 80-125%. Thus, it was concluded that the test product (Dasatinib ASD Tablet) was not bioequivalent to the reference product (SPRYCEL tablet) under fasted conditions. With respect to $C_{max}$, the within-subject variability for the reference product was significant, which indicated the use of Scaled Average Bioequivalence (SABE) method for this parameter rather than the Average Bioequivalence (ABE) method.

Based on the statistical analysis for the fed study, the estimated 90% confidence interval for the ratio of geometric means of test and reference products for $C_{max}$, $AUC_{last}$ and $AUC_{0\text{-}inf}$ fall within the bioequivalence limit of 80-125% under fed conditions. Thus, it was concluded that the test product (Dasatinib ASD Tablet) was bioequivalent to the reference product (SPRYCEL tablet) under fed conditions.

It can further be seen that the test product (Dasatinib ASD Tablet) exhibited a variability, designated by the coefficient of variation (CV, expressed in percent), that was as good or better than the reference product (SPRYCEL tablet) under all conditions for most parameters. Under fed conditions, the variability was quite comparable for test and reference products for all relevant parameters $C_{max}$, $AUC_{last}$, and $AUC_{0\text{-}inf}$. Under fasted conditions, the variability was significantly improved for the test product for all relevant parameters $C_{max}$, $AUC_{last}$, and $AUC_{0\text{-}inf}$ as compared to the reference product.

Furthermore, the test product (Dasatinib ASD Tablet) exhibited a similar variability for both the fasted and fed state, which is in contrast to the reference product, which exhibited a significantly higher variability under fasted conditions.

The foregoing description is given for clearness of understanding only, and no unnecessary limitations should be understood therefrom. Various modifications and alterations to this disclosure will become apparent to those skilled in the art without departing from the scope and spirit of this disclosure. It should be understood that this disclosure is not intended to be unduly limited by the illustrative embodiments and examples set forth herein, and such examples and embodiments are presented by way of example only.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

The term "comprises" and variations such as "comprises" and "comprising" do not have a limiting meaning where these terms appear in the description and claims. Such terms will be understood to imply the inclusion of a stated step or element or group of steps or elements but not the exclusion of any other step or element or group of steps or elements.

By "consists of" (or similarly "consisting of") is meant including, and limited to, whatever follows the phrase "consists of." Thus, the phrase "consists of" in dictates that the listed elements are required or mandatory, and that no other elements may be present. By "consists essentially of" (or similarly "consisting essentially of") is meant including any elements listed after the phrase, and limited to other elements that do not interfere with or contribute to the activity or action specified in the disclosure for the listed elements. Thus, the phrase "consists essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refer to any one of the items in the list and any combination of two or more items in the list.

As used herein, the term "or" is generally employed in its usual sense including "and/or" unless the content clearly dictates otherwise. The term "and/or" means one or all of the listed elements or a combination of any two or more of the listed elements (e.g., preventing and/or treating an affliction means preventing, treating, or both treating and preventing further afflictions).

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50). Also herein, the recitations of numerical ranges by endpoints include all numbers subsumed within that range as well as the endpoints (e.g., 1 to 5 includes 1, 1.5, 2, 2.75, 3, 3.80, 4, 5, etc.) and any sub-ranges (e.g., 1 to 5 includes 1 to 4, 1 to 3, 2 to 4, etc.).

The complete disclosures of the patents, patent documents, and publications cited herein are incorporated by reference in their entirety as if each were individually incorporated. To the extent that there is any conflict or discrepancy between the present disclosure and the disclosure in any document that is incorporated by reference, this disclosure as written will control.

What is claimed is:

1. A method of treating a proliferative disorder in a patient in need thereof, the method comprising:
   (a) administering to the patient a pharmaceutical composition comprising an amorphous solid dispersion, the amorphous solid dispersion consisting essentially of dasatinib, a methacrylic acid and ethyl acrylate copolymer that exhibits pH-dependent solubility, and optionally one or more functional components selected from the group consisting of antioxidants, wetting agents, and solubilizers; and
   (b) co-administering to the patient a gastric acid-reducing agent;
   wherein the dasatinib and the copolymer are present in the amorphous solid dispersion in a w/w ratio of 30:70 to 95:5 (dasatinib:copolymer).

2. The method of claim 1, wherein the gastric acid-reducing agent is administered to the patient shortly before the pharmaceutical composition is administered.

3. The method of claim 1, wherein the gastric acid-reducing agent is administered to the patient concurrently with the administration of the pharmaceutical composition.

4. The method of claim 1, wherein the gastric acid-reducing agent is administered to the patient shortly after the pharmaceutical composition is administered.

5. The method of claim 1, wherein the amorphous solid dispersion includes one or more functional components selected from the group consisting of antioxidants, wetting agents, and solubilizers.

6. The method of claim 1, wherein the amorphous solid dispersion consists of dasatinib and the copolymer.

7. A treatment regimen for treating a proliferative disorder in a patient in need thereof, the regimen comprising:
   (a) administering to the patient a first dose, the first dose comprising a standard dosage of a proton pump inhibitor or an $H_2$ antagonist; and
   (b) within 12 hours after the first dose, administering a second dose to the patient, the second dose comprising a therapeutically effective amount of a pharmaceutical composition comprising an amorphous solid dispersion, the amorphous solid dispersion consisting essentially of dasatinib, a methacrylic acid and ethyl acrylate copolymer that exhibits pH-dependent solubility, and optionally one or more functional components selected from the group consisting of antioxidants, wetting agents, and solubilizers;
   wherein the dasatinib and the copolymer are present in the amorphous solid dispersion in a w/w ratio of 30:70 to 95:5 (dasatinib:copolymer); and
   wherein the therapeutically effective amount comprises 20 mg to 140 mg dasatinib.

8. The treatment regimen of claim 7, wherein the first dose comprises a standard dosage of a proton pump inhibitor.

9. The treatment regimen of claim 7, wherein the first dose comprises a standard dosage of a proton pump inhibitor selected from rabeprazole, esomeprazole, lansoprazole, omeprazole, pantoprazole, dexlansoprazole, or a combination thereof.

10. The treatment regimen of claim 7, wherein the first dose comprises a standard dosage of an $H_2$ antagonist.

11. The treatment regimen of claim 7, wherein the first dose comprises a standard dosage of an $H_2$ antagonist selected from famotidine, cimetidine, nizatidine, ranitidine, or a combination thereof.

12. The treatment regimen of claim 7, wherein the second dose is administered within 8 hours after the first dose.

13. The treatment regimen of claim 7, wherein the second dose is administered within 6 hours after the first dose.

14. The treatment regimen of claim 7, wherein the second dose is administered within 4 hours after the first dose.

15. The treatment regimen of claim 7, wherein the amorphous solid dispersion includes one or more functional components selected from the group consisting of antioxidants, wetting agents, and solubilizers.

16. The treatment regimen of claim 7, wherein the amorphous solid dispersion consists of dasatinib and the copolymer.

17. The treatment regimen of claim 7, wherein the copolymer is insoluble in an aqueous medium at pH of 5 or lower, and soluble in an aqueous medium at pH 5.5 or greater.

18. The treatment regimen of claim 15, wherein the one or more functional components is selected from one or more antioxidants that are present in an amount of 0.001% to 2% by weight of the amorphous solid dispersion.

19. The treatment regimen of claim 18, wherein the one or more antioxidants comprises propyl gallate.

20. The treatment regimen of claim 7, wherein the dasatinib and the copolymer are present in the amorphous solid dispersion in a w/w ratio of 40:60 to 70:30 (dasatinib:copolymer).

21. The treatment regimen of claim 7, wherein the pharmaceutical composition comprises the amorphous solid dispersion and one or more pharmaceutically acceptable additives.

22. The treatment regimen of claim 7, wherein the pharmaceutical composition is a solid dosage form suitable for oral administration.

23. The treatment regimen of claim 7, wherein the pharmaceutical composition is a gastric acid-insensitive composition.

24. The method of claim 1, wherein the copolymer is insoluble in an aqueous medium at pH of 5 or lower, and soluble in an aqueous medium at pH 5.5 or greater.

25. The method of claim 5, wherein the one or more functional components is selected from one or more antioxidants that are present in an amount of 0.001% to 2% by weight of the amorphous solid dispersion.

26. The method of claim 25, wherein the one or more antioxidants comprises propyl gallate.

27. The method of claim 1, wherein the dasatinib and the copolymer are present in the amorphous solid dispersion in a w/w ratio of 40:60 to 70:30 (dasatinib:copolymer).

28. The method of claim 1, wherein the pharmaceutical composition comprises the amorphous solid dispersion and one or more pharmaceutically acceptable additives.

29. The method of claim 1, wherein the pharmaceutical composition is a solid dosage form suitable for oral administration.

30. The method of claim 1, wherein the pharmaceutical composition is a gastric acid-insensitive composition.

* * * * *